(12) United States Patent  
Hsieh et al.

(10) Patent No.: US 7,449,478 B2
(45) Date of Patent: Nov. 11, 2008

(54) INDOLE COMPOUNDS

(75) Inventors: Hsing-Pang Hsieh, Taipei (TW); Neeraj Mahindroo, Himachal Pradesh (IN); Tsu-An Hsu, Taipei (TW); Chien-Fu Huang, Kaohsiung (TW); Xin Chen, Sijhih (TW); Yu-Sheng Chao, Warren, NJ (US)

(73) Assignee: National Health Research Institutes, Miaoli County (TW)

( * ) Notice: Subject to any disclaimer, the term of this patent is extended or adjusted under 35 U.S.C. 154(b) by 408 days.

(21) Appl. No.: 11/003,181

(22) Filed: Dec. 3, 2004

(65) Prior Publication Data

US 2005/0124675 A1    Jun. 9, 2005

Related U.S. Application Data

(60) Provisional application No. 60/526,872, filed on Dec. 4, 2003.

(51) Int. Cl.
*A61K 31/422* (2006.01)
*A61K 31/4709* (2006.01)
*C07D 263/62* (2006.01)
*C07D 453/04* (2006.01)

(52) U.S. Cl. .................. 514/312; 514/375; 546/135; 548/219

(58) Field of Classification Search ................ 514/312, 514/375; 546/135; 548/219
See application file for complete search history.

(56) References Cited

U.S. PATENT DOCUMENTS

| 5,496,844 | A | 3/1996 | Inai et al. ............ 514/415 |
| 6,525,083 | B2 | 2/2003 | Acton, III et al. ........ 514/415 |
| 6,630,496 | B1 | 10/2003 | Seehra et al. ............ 514/369 |

FOREIGN PATENT DOCUMENTS

| WO | WO 97/28137 | 8/1997 |
| WO | WO 98/27974 | 7/1998 |
| WO | WO 02/08188 A1 | 1/2002 |
| WO | WO 02/18377 A1 | 3/2002 |
| WO | WO 02/30895 A1 | 4/2002 |
| WO | WO 02/060438 A1 | 8/2002 |
| WO | WO 03/018553 A1 | 3/2003 |

OTHER PUBLICATIONS

King, Med Chem: Principle and Practice (1994), p. 206-209.*
Adams et al., "Amphipathic 3-Phenyl-7-propylbenzisoxazoles; Human PPaR γ, δ and α Agonists", Biorganic & Medicinal Chemistry Letters 13:931-935, 2003.
Jones, "Peroxisome Proliferator-Activated Receptor (PPAR) Modulators: Diabetes and Beyond", Medicinal Research Reviews 21:540-552, 2001.
Santini et al., "Phenylacetic Acid Derivatives as hPPAR Agonists", Bioorganic & Medicinal Chemistry Letters 13:1277-1280, 2003.
Shearer et al., "Recent Advances in Peroxisome Proliferator-Activated Receptor Science", Current Medicinal Chemistry 10:267-280, 2003.
Willson et al., "The PPARs: From Orphan Receptors to Drug Discovery", Journal of Medicinal Chemistry 43:527-550, 2000.

* cited by examiner

*Primary Examiner*—Taofiq A Solola
(74) *Attorney, Agent, or Firm*—Occhiuti Rohlicek & Tsao LLP

(57) ABSTRACT

This invention relates to treating peroxisome proliferator-activated receptors related diseases with certain indole compounds. The indole compounds are of formula (I) below. Each variable is defined in the specification.

(I)

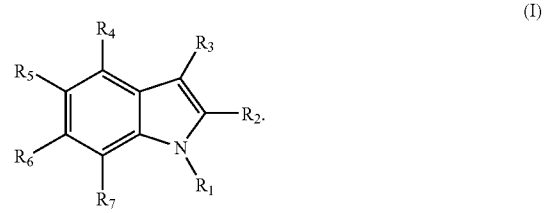

23 Claims, No Drawings

INDOLE COMPOUNDS

CROSS REFERENCE TO RELATED APPLICATION

Pursuant to 35 U.S.C. § 119 (e), this application claims priority to U.S. Provisional Application Ser. No. 60/526,872, filed Dec. 4, 2003.

BACKGROUND

Diabetes is one of the major threats to human health in the 21st century. The number of patients is predicted to rise from 150-220 million in 2010 to 300 million in 2025. A majority of the patients have type II diabetes, which is characterized by insulin resistance. At present, therapy for type II diabetes relies mostly on reducing hyperglycaemia. It has limited efficacy and significant side effects. Thus, there is a need to develop more effective drugs for treating type II diabetes.

Evidence has shown that lipid accumulation in muscle and liver would lead to the development of insulin resistance. It has also been shown that reducing obesity or lowering lipids generally improves insulin sensitivity. Peroxisome proliferator-activated receptors (PPARs) belong to a family of nuclear receptors that regulate lipid metabolism. For example, PPARγ is highly expressed in adipocytes and mediates their differentiation. Thiazolidinediones (TZDs), a group of PPARγ agonists, have been demonstrated to be effective in treating type II diabetes. Studies suggest that TZDs may improve muscle insulin action and increase insulin sensitivity by sequestering lipids in adipocytes and reducing lipid accumulation in muscle.

SUMMARY

This invention is based on the discovery that certain indole compounds can be used to treat type II diabetes through their binding to PPARs (e.g., PPARα, PPARγ, or PPARδ).

In one aspect, this invention features a method for treating a PPAR-related disease. The method includes administering to a subject in need thereof an effective amount of a compound of formula (I):

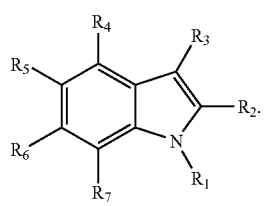

(I)

In the above formula, $R_1$ is $(CR_bR_c)_n$—X—$R_a$, in which n is 2-5; X is $N(R_d)$, O, or S, or X and $R_a$, taken together, is heteroaryl; $R_a$ is H, $C_1$-$C_6$ alkyl, $C_3$-$C_{15}$ cycloalkyl, $C_3$-$C_{15}$ heterocycloalkyl, heteroaryl, or aryl, or $R_a$ and X, taken together, is heteroaryl; each $R_b$, independently, is H, $C_1$-$C_6$ alkyl, aryl, or heteroaryl; and each $R_c$, independently, is H, $C_1$-$C_6$ alkyl, aryl, or heteroaryl; $R_d$ being H, $C_1$-$C_6$ alkyl, aryl, or heteroaryl; and one of $R_2$, $R_3$, $R_4$, $R_5$, $R_6$, and $R_7$ is OH, halogen, $C_1$-$C_6$ alkyl, $C_3$-$C_{15}$ cycloalkyl, $C_3$-$C_{15}$ heterocycloalkyl, aryl, heteroaryl, $C_1$-$C_6$ alkoxy, aryloxy, heteroaryloxy, $C_1$-$C_6$ alkylthio, arylthio, $NH_2$, $C_1$-$C_6$ alkylamino, $C_1$-$C_{12}$ dialkylamino, arylamino, diarylamino, $NO_2$, CN, $SO_3H$, $SO_2N(R_eR_f)$, $SO_2R_e$, $COOR_e$, or $C(O)R_e$; each of the others, independently, is H, OH, halogen, $C_1$-$C_6$ alkyl, $C_3$-$C_{15}$ cycloalkyl, $C_3$-$C_{15}$ heterocycloalkyl, aryl, heteroaryl, $C_1$-$C_6$ alkoxy, aryloxy, heteroaryloxy, $C_1$-$C_6$ alkylthio, arylthio, $NH_2$, $C_1$-$C_6$ alkylamino, $C_1$-$C_{12}$ dialkylamino, arylamino, diarylamino, $NO_2$, CN, $SO_3H$, $SO_2N(R_eR_f)$, $SO_2R_e$, $COOR_e$, or $C(O)R_e$; each of $R_e$ and $R_f$, independently, being H, $C_1$-$C_6$ alkyl, aryl, or heteroaryl.

For example, one can administer to a subject infected with a PPAR-related disease a compound of formula (I), in which $R_a$ is heteroaryl or aryl, or $R_a$ and X, taken together, is heteroaryl; and one of $R_2$, $R_3$, $R_4$, $R_5$, $R_6$, and $R_7$ is OH, $C_1$-$C_6$ alkyl, $C_1$-$C_6$ alkoxy, or $COOR_e$, each of the others, independently, is H, $C_1$-$C_6$ alkyl, $C_1$-$C_6$ alkoxy, or $C(O)R_e$. In this compound, $R_a$ can be

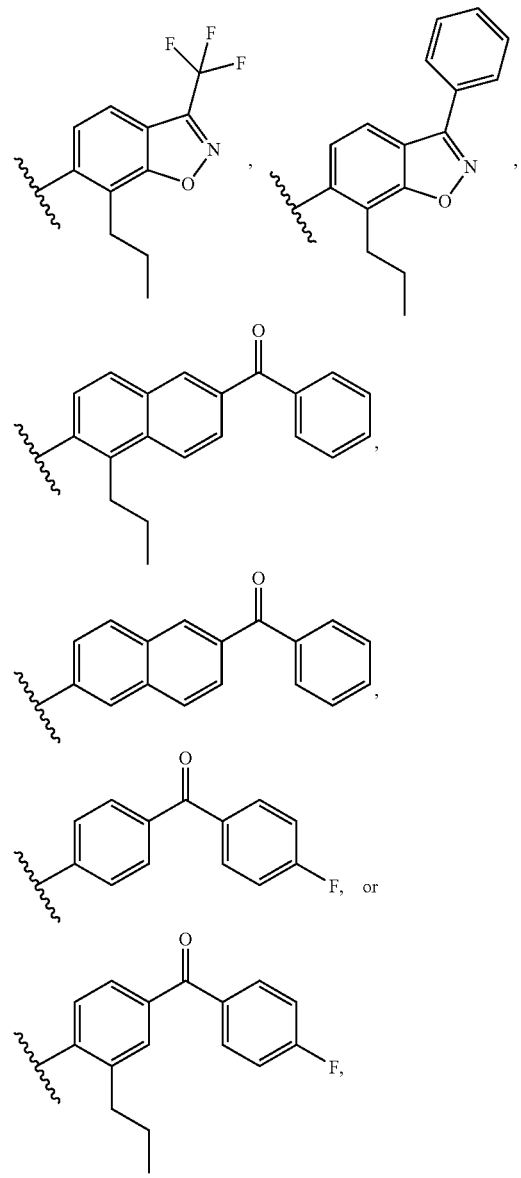

and one of $R_2$, $R_3$, $R_4$, $R_5$, $R_6$, and $R_7$ can be OH, $OCH_2COOR$, $OC(CH_3)_2COOR$, $OCH(CH_3)COOR$, $O(CH_2)_2COOR$, $O(CH_2)_3COOR$, $CH_2COOR$, COOR,

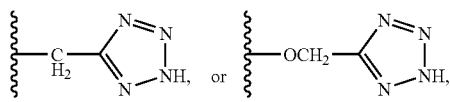

in which R is H, $C_1$-$C_6$ alkyl, aryl, or heteroaryl.

"Treating" refers to administering one or more indole compounds to a subject, who has a PPAR-related disease, a symptom of such a disease, or a predisposition toward such a disease, with the purpose to confer a therapeutic effect, e.g., to cure, relieve, alter, affect, ameliorate, or prevent the PPAR-related disease, the symptom of it, or the predisposition toward it. "An effective amount" refers to the amount of one or more active indole compounds that is required to confer a therapeutic effect on a treated subject.

Examples of PPAR-related diseases (or disorders or conditions) include diabetes mellitus (e.g., type I diabetes or type II diabetes), hyperglycemia, low glucose tolerance, Syndrome X, insulin resistance, obesity (e.g., abdominal obesity), lipid disorders, dyslipidemia, hyperlipidemia, hyperglycaemia, hypertriglyceridemia, hypercholesterolemia, low HDL levels, high LDL levels, atherosclerosis (and its sequelae such as angina, claudication, heart attack, or stroke), vascular restenosis, irritable bowel syndrome, inflammatory diseases (e.g., inflammatory bowel disease, rheumatoid arthritis, Crohn's disease, ulcerative colitis, osteoarthritis, multiple sclerosis, asthma, vasculitis, gout, pancreatitis, ischemia/reperfusion injury, frostbite, or adult respiratory distress syndrome), neurodegenerative disease, retinopathy, neoplastic conditions, cancers (e.g., prostate, gastric, breast, bladder, lung, or colon cancer, or adipose cell cancer such as liposarcoma), angiogenesis, Alzheimer's disease, skin disorders (e.g., acne, psoriasis, dermatitis, eczema, or keratosis), high blood pressure, ovarian hyperandrogenism, osteoporosis, and osteopenia.

The term "alkyl" refers to a saturated or unsaturated, linear or branched, non-aromatic hydrocarbon moiety, such as —$CH_3$, —$CH_2$—, —$CH_2$—CH=$CH_2$—, or branched —$C_3H_7$. The term "cycloalkyl" refers to a saturated or unsaturated, non-aromatic, cyclic hydrocarbon moiety, such as cyclohexyl or cyclohexen-3-yl. The term "heterocycloalkyl" refers to a saturated or unsaturated, non-aromatic, cyclic moiety having at least one ring heteroatom, such as 4-tetrahydropyranyl or 4-pyranyl. The term "aryl" refers to a hydrocarbon moiety having one or more aromatic rings. Examples of an aryl moiety include phenyl, phenylene, naphthyl, naphthylene, pyrenyl, anthryl, and phenanthryl. The term "heteroaryl" refers to a moiety having one or more aromatic rings that contain at least one heteroatom. Examples of a heteroaryl moiety include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl. The term "alkoxy" refers to a linear or branched, saturated or unsaturated, non-aromatic hydrocarbon moiety containing an oxygen radical, such as —$OCH_3$ or —OCH=$C_2H_5$. The term "aryloxy" refers to a moiety having at least one aromatic ring and an oxygen radical bonded to the aromatic ring, such as phenoxy. The term "heteroaryloxy" refers to a moiety having at least one aromatic ring that contains at least one ring heteroatom and an oxygen radical bonded to the aromatic ring, such as 4-pyrindinoxy. The term "alkylthio" refers to a linear or branched, saturated or unsaturated, non-aromatic hydrocarbon moiety containing a sulfur radical, such as —$SCH_3$ or —SCH=$C_2H_5$. The term "arylthio" refers to a moiety having at least one aromatic ring and a sulfur radical bonded to the aromatic ring, such as phenylthio. The term "alkylamino" refers to a moiety having a nitrogen radical bonded to an alkyl group defined above, such as —$NHCH_3$ or —NHCH=$C_2H_5$. The term "dialkylamino" refers to a moiety having a nitrogen radical bonded to two alkyl groups defined above, such as —$N(CH_3)_2$ or —$N(CH_3)$(CH=$C_2H_5$). The term "arylamino" refers to a moiety having a nitrogen radical bonded to an aryl group defined above, such as phenylamino. The term "diarylamino" refers to a moiety having a nitrogen radical bonded to two aryl groups defined above, such as diphenylamino.

Alkyl, cycloalkyl, heterocycloalkyl, aryl, heteroaryl, alkoxy, aryloxy, heteroaryloxy, alkylthio, arylthio, alkylamino, dialkylamino, arylamino, and diarylamino mentioned herein include both substituted and unsubstituted moieties, unless specified otherwise. Possible substituents on cycloalkyl, heterocycloalkyl, aryl, heteroaryl, aryloxy, heteroaryloxy, arylthio, arylamino, and diarylamino include $C_1$-$C_{10}$ alkyl, $C_2$-$C_{10}$ alkenyl, $C_2$-$C_{10}$ alkynyl, $C_3$-$C_8$ cycloalkyl, $C_5$-$C_8$ cycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, hydroxyl, halogen, thio, $C_1$-$C_{10}$ alkylthio, arylthio, $C_1$-$C_{10}$ alkylsulfonyl, arylsulfonyl, cyano, nitro, acyl, acyloxy, carboxyl, and carboxylic ester. On the other hand, possible substituents on alkyl, alkoxy, alkylthio, alkylamino, and dialkylamino include all of the above-recited substituents except $C_1$-$C_{10}$ alkyl, $C_2$-$C_{10}$ alkenyl, and $C_2$-$C_{10}$ alkynyl. Cycloalkyl and heterocycloalkyl can also be fused with aryl or heteroaryl.

In another aspect, this invention features a method for treating a PPAR-related disease, which includes administering to a subject in need thereof an effective amount of a compound of formula (I) shown above except that $R_1$ is H, $C_1$-$C_6$ alkyl, $C_3$-$C_{15}$ cycloalkyl, $C_3$-$C_{15}$ heterocycloalkyl, aryl, heteroaryl, C(O)$R_a$, or $SO_2R_a$, in which $R_a$ is $C_1$-$C_6$ alkyl, aryl, or heteroaryl; and one of $R_2$, $R_3$, $R_4$, $R_5$, $R_6$, and $R_7$ is $(CR_dR_e)_m$—X—$R_b$, O—$(CR_dR_e)_m$—X—$R_b$, or O—C$(R_dR_e)R_c$, and each of the others, independently, is H, OH, halogen, $C_1$-$C_6$ alkyl, $C_3$-$C_{15}$ cycloalkyl, $C_3$-$C_{15}$ heterocycloalkyl, aryl, heteroaryl, $C_1$-$C_6$ alkoxy, aryloxy, heteroaryloxy, $C_1$-$C_6$ alkylthio, arylthio, $NH_2$, $C_1$-$C_6$ alkylamino, $C_1$-$C_{12}$ dialkylamino, arylamino, diarylamino, $NO_2$, CN, $SO_3H$, $SO_2N(R_fR_g)$, $SO_2R_f$, $COOR_f$, or C(O)$R_f$; or one of $R_2$, $R_3$, $R_4$, $R_5$, $R_6$, and $R_7$ is $(CR_dR_e)_n$—X—$R_b$, O—$(CR_dR_e)_n$—X—$R_b$, or O—C($R_{dc}$, and each of the others, independently, is H, OH, halogen, $C_3$-$C_6$ alkyl, $C_3$-$C_{15}$ cycloalkyl, $C_3$-$C_{15}$ heterocycloalkyl, aryl, heteroaryl, $C_1$-$C_6$ alkoxy, aryloxy, heteroaryloxy, $C_1$-$C_6$ alkylthio, arylthio, $NH_2$, $C_1$-$C_6$ alkylamino, $C_1$-$C_{12}$ dialkylamino, arylamino, diarylamino, $NO_2$, CN, $SO_3H$, $SO_2N(R_fR_g)$, $SO_2R_f$, $COOR_f$, or C(O)$R_f$; in which m is 3-5; n is 2-5; X is N($R_h$), O, or S, or X and $R_b$, taken together, is heteroaryl; $R_b$ is H, $C_1$-$C_6$ alkyl, heteroaryl, $COOR_i$, or aryl optionally substituted with OH, halogen, $C_3$-$C_6$ alkyl, $C_3$-$C_{15}$ cycloalkyl, $C_3$-$C_{15}$ heterocycloalkyl, $C_1$-$C_6$ alkoxy, aryloxy, heteroaryloxy, heteroaryl, aryl, $NO_2$, CN, $COOR_i$, or C(O)$R_i$, or $R_b$ and X taken together, is heteroaryl; $R_c$ is H, OH, halogen, $NH_2$, $C_1$-$C_6$ alkylamino, $C_1$-$C_{12}$ dialkylamino, arylamino, diarylamino, $C_1$-$C_6$ alkyl, heteroaryl, $COOR_i$, or aryl optionally substituted with OH, halogen, $C_3$-$C_6$ alkyl, $C_3$-$C_{15}$ cycloalkyl, $C_3$-$C_{15}$ heterocycloalkyl, $C_1$-$C_6$ alkoxy, aryloxy, heteroaryloxy, heteroaryl, aryl, $NO_2$, CN, $COOR_i$, or C(O)$R_i$; each $R_d$, independently, is H, $C_1$-$C_6$ alkyl, aryl, or heteroaryl; each $R_e$, independently, is H, $C_1$-$C_6$ alkyl, aryl, or heteroaryl; each of $R_f$ and $R_g$, independently, is H, $C_1$-$C_6$ alkyl, aryl, or heteroaryl; each of $R_h$ and $R_i$, independently, being H, $C_1$-$C_6$ alkyl, aryl, or heteroaryl.

For example, one can administer to a subject infected with a PPAR-related disease a compound of formula (I), in which $R_1$ is H, $C_1$-$C_6$ alkyl, or $SO_2R_a$; one of $R_2$, $R_3$, $R_4$, $R_5$, $R_6$, and $R_7$ is $(CR_dR_e)_m$—X—$R_b$, O—$(CR_dR_e)_m$—X—$R_b$, or O—C$(R_dR_e)R_c$, and each of the others, independently, is H, $C_1$-$C_6$ alkyl, $C_1$-$C_6$ alkoxy, or $COOR_f$; or one of $R_2$, $R_3$, $R_4$, $R_5$, $R_6$, and $R_7$ is $(CR_dR_e)_n$—X—$R_b$ or O—$(CR_dR_e)_n$—X—$R_b$, and each of the others, independently, is H; n is 2; $R_b$ is heteroaryl or aryl substituted with $C_3$-$C_6$ alkyl, heteroaryl, or $C(O)R_i$; and $R_c$ is $COOR_j$. In this compound, $R_b$ can be

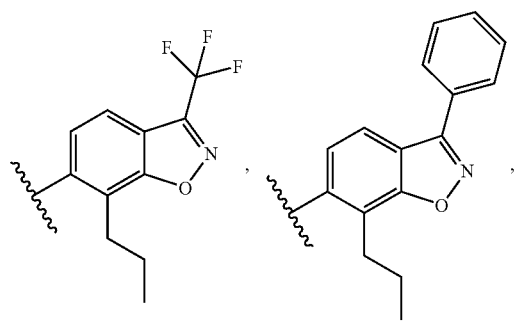

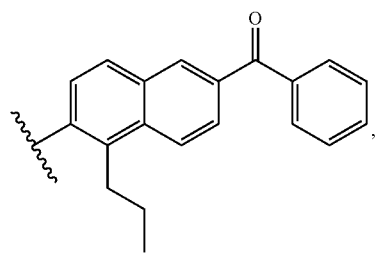

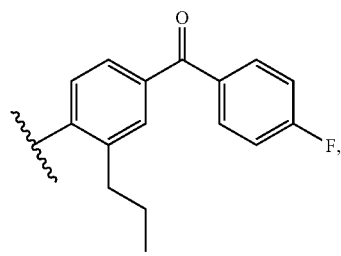

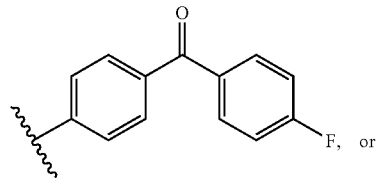

and $R_1$ can be H, $CH_2COOR$, $CH(CH_3)COOR$, $CH(CH_2CH_3)COOR$, $CH_2CH_2COOR$, $CH_2(CH_2)_2COOR$, or

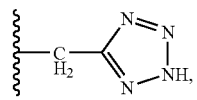

in which R is H, $C_1$-$C_6$ alkyl, aryl, or heteroaryl.

In still another aspect, this invention features a compound of formula (I) show above. In this formula, $R_1$ is $(CR_cR_d)(CR_cR_d)_m$—X—$R_a$ or $(CR_cR_d)_n$—X—$R_b$, in which m is 3-5; n is 2-5; X is $N(R_e)$, O, or S, or X and $R_a$ or X and $R_b$, taken together, is heteroaryl; $R_a$ is H, $C_1$-$C_6$ alkyl, $C_3$-$C_{15}$ cycloalkyl, $C_3$-$C_{15}$ heterocycloalkyl, heteroaryl, or aryl optionally substituted with OH, halogen, $C_3$-$C_6$ alkyl, $C_3$-$C_{15}$ cycloalkyl, $C_3$-$C_{15}$ heterocycloalkyl, $C_1$-$C_6$ alkoxy, aryloxy, heteroaryloxy, heteroaryl, aryl, $NO_2$, CN, $COOR_f$, or $C(O)R_f$, or $R_a$ and X, taken together, is heteroaryl; $R_b$ is H, $C_1$-$C_6$ alkyl, $C_3$-$C_{15}$ cycloalkyl, $C_3$-$C_{15}$ heterocycloalkyl, heteroaryl, or aryl optionally substituted with OH, halogen, $C_3$-$C_6$ alkyl, $C_3$-$C_{15}$ cycloalkyl, $C_3$-$C_{15}$ heterocycloalkyl, aryloxy, heteroaryloxy, heteroaryl, aryl, $NO_2$, CN, $COOR_f$, or $C(O)R_f$, or $R_b$ and X, taken together, is heteroaryl; each $R_c$, independently, is H, $C_1$-$C_6$ alkyl, aryl, or heteroaryl; and each $R_d$, independently, is H, $C_1$-$C_6$ alkyl, aryl, or heteroaryl; each of $R_e$ and $R_f$, independently, being H, $C_1$-$C_6$ alkyl, aryl, or heteroaryl; and one of $R_2$, $R_3$, $R_4$, $R_5$, $R_6$, and $R_7$ is $C_1$-$C_6$ alkyl, $C_3$-$C_{15}$ cycloalkyl, $C_3$-$C_{15}$ heterocycloalkyl, aryl, heteroaryl, $C_1$-$C_6$ alkoxy, aryloxy, heteroaryloxy, $C_1$-$C_6$ alkylthio, arylthio, $NH_2$, $C_1$-$C_6$ alkylamino, $C_1$-$C_{12}$ dialkylamino, arylamino, diarylamino, $NO_2$, CN, $SO_3H$, $SO_2N(R_gR_h)$, $SO_2R_g$, $COOR_g$, or $C(O)R_g$; and each of the others, independently, is H, $C_1$-$C_6$ alkyl, $C_3$-$C_{15}$ cycloalkyl, $C_3$-$C_{15}$ heterocycloalkyl, aryl, heteroaryl, $C_1$-$C_6$ alkoxy, aryloxy, heteroaryloxy, $C_1$-$C_6$ alkylthio, arylthio, $NH_2$, $C_1$-$C_6$ alkylamino, $C_1$-$C_{12}$ dialkylamino, arylamino, diarylamino, $NO_2$, CN, $SO_3H$, $SO_2N(R_gR_h)$, $SO_2R_g$, $COOR_g$, or $C(O)R_g$; each of $R_g$ and $R_h$, independent, being H, $C_1$-$C_6$ alkyl, aryl, or heteroaryl.

Referring to formula (I), a subset of the just-described compounds are those in which $R_a$ is heteroaryl or aryl substituted with $C_3$-$C_6$ alkyl, $C_1$-$C_6$ alkoxy, heteroaryl, $C(O)R_f$, or $NO_2$, or $R_a$ and X, taken together, is heteroaryl; $R_b$ is heteroaryl; n is 2; one of $R_2$, $R_3$, $R_4$, $R_5$, $R_6$, and $R_7$ is OH, $C_1$-$C_6$ alkyl, $C_1$-$C_6$ alkoxy, or $COOR_e$; and each of the others, independently, is H, $C_1$-$C_6$ alkyl, $C_1$-$C_6$ alkoxy, or $C(O)R_e$. In these compounds, $R_a$ can be

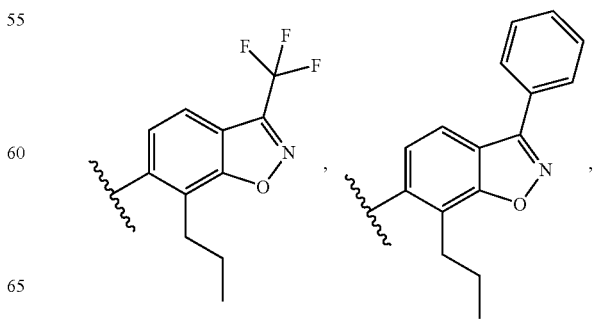

-continued

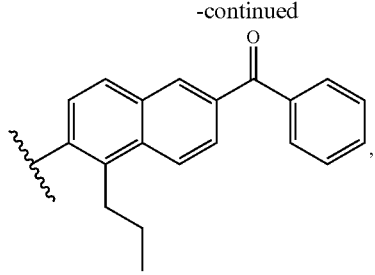

,

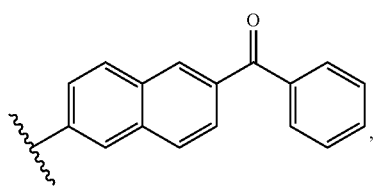

,

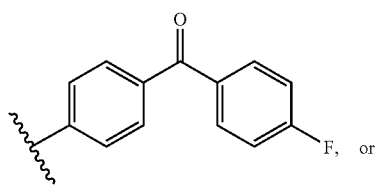

F, or

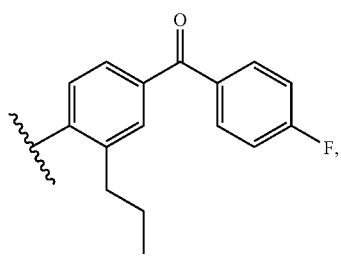

F, and one of $R_2$, $R_3$, $R_4$, $R_5$, $R_6$, and $R_7$ can be OH, $OCH_2COOR$, $OC(CH_3)_2COOR$, $OCH(CH_3)COOR$, $O(CH_2)_2COOR$, $O(CH_2)_3COOR$, $CH_2COOR$, COOR,

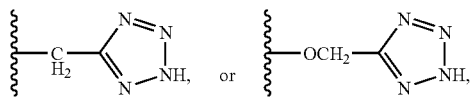

in which R is H, $C_1$-$C_6$ alkyl, aryl, or heteroaryl.

In yet another aspect, this invention features a compound of formula (I) shown above except that $R_1$ is H, $C_1$-$C_6$ alkyl, $C_3$-$C_{15}$ cycloalkyl, $C_3$-$C_{15}$ heterocycloalkyl, aryl, heteroaryl, $C(O)R_a$, or $SO_2R_a$, in which $R_a$ is $C_1$-$C_6$ alkyl, heteroaryl, or aryl optionally substituted with $CF_3$, OH, halogen, $C_1$-$C_6$ alkoxy, aryloxy, heteroaryloxy, $C_3$-$C_{15}$ cycloalkyl, $C_3$-$C_{15}$ heterocycloalkyl, aryl, heteroaryl, $NO_2$, CN, $COOR_b$, or $C(O)R_b$; $R_b$ being H, $C_1$-$C_6$ alkyl, aryl, or heteroaryl; and one of $R_2$, $R_3$, $R_4$, $R_5$, $R_6$, and $R_7$ is $(CR_eR_f)_m$—X—$R_c$, O—$(CR_eR_f)_m$—X—$R_c$, or O—$C(R_eR_f)R_d$; and each of the others, independently, is H, OH, halogen, $C_1$-$C_6$ alky, $C_3$-$C_{15}$ cycloalkyl, $C_3$-$C_{15}$ heterocycloalkyl, aryl, heteroaryl, $C_1$-$C_6$ alkoxy, aryloxy, heteroaryloxy, $C_1$-$C_6$ alkylthio, arylthio, $NH_2$, $C_1$-$C_6$ alkylamino, $C_1$-$C_{12}$ dialkylamino, arylamino, diarylamino, $NO_2$, CN, $SO_3H$, $SO_2N(R_gR_h)$, $SO_2R_g$, $COOR_g$, or $C(O)R_g$; or one of $R_2$, $R_3$, $R_4$, $R_5$, $R_6$, and $R_7$ is $(CR_eR_f)_n$—X—$R_c$, O—$(CR_eR_f)_n$—X—$R_c$, or O—$C(R_eR_f)R_d$; and each of the others, independently, is H, OH, halogen, $C_3$-$C_6$ alkyl, $C_3$-$C_{15}$ cycloalkyl, $C_3$-$C_{15}$ heterocycloalkyl, aryl, heteroaryl, $C_3$-$C_6$ alkoxy, aryloxy, heteroaryloxy, $C_1$-$C_6$ alkylthio, arylthio, $NH_2$, $C_1$-$C_6$ alkylamino, $C_1$-$C_{12}$ dialkylamino, arylamino, diarylamino, $NO_2$, CN, $SO_3H$, $SO_2N(R_gR_h)$, $SO_2R_g$, $COOR_g$, or $C(O)R_g$; in which m is 3-5; n is 2-5; X is $N(R_i)$, O, or S, or X and $R_c$, taken together, is heteroaryl; $R_c$ is $C_1$-$C_6$ alkyl, $COOR_j$, heteroaryl containing at least two aromatic rings fused together, or aryl optionally substituted with OH, halogen, $C_3$-$C_6$ alkyl, $C_3$-$C_{15}$ cycloalkyl, $C_3$-$C_{15}$ heterocycloalkyl, $C_1$-$C_6$ alkoxy, aryloxy, heteroaryloxy, heteroaryl, aryl, $NO_2$, CN, $COOR_j$, or $C(O)R_j$, or $R_c$ and X taken together, is heteroaryl; $R_d$ is H, OH, halogen, $NH_2$, $C_1$-$C_6$ alkylamino, $C_1$-$C_{12}$ dialkylamino, arylamino, diarylamino, $C_1$-$C_6$ alkyl, heteroaryl, $COOR_i$, or aryl optionally substituted with OH, halogen, $C_3$-$C_6$ alkyl, $C_3$-$C_{15}$ cycloalkyl, $C_3$-$C_{15}$ heterocycloalkyl, $C_1$-$C_6$ alkoxy, aryloxy, heteroaryloxy, heteroaryl, aryl, $NO_2$, CN, $COOR_j$, or $C(O)R_j$; each $R_e$, independently, is H, $C_1$-$C_6$ alkyl, aryl, or heteroaryl; each $R_f$, independently, is H, $C_1$-$C_6$ alkyl, aryl, or heteroaryl; and each of $R_g$ and $R_h$, independently, is H, $C_1$-$C_6$ alkyl, aryl, or heteroaryl; each of $R_i$ and $R_j$, independently, being H, $C_1$-$C_6$ alkyl, aryl, or heteroaryl.

Referring to formula (I), a subset of the just-described compounds are those in which $R_1$ is H, $C_1$-$C_6$ alkyl, or $SO_2R_a$; one of $R_2$, $R_3$, $R_4$, $R_5$, $R_6$, and $R_7$ is $(CR_eR_f)_m$—X—$R_c$, O—$(CR_eR_f)_m$—X—$R_c$, or O—$C(R_eR_f)R_d$, and each of the others, independently, is H, $C_1$-$C_6$ alkyl, $C_1$-$C_6$ alkoxy, or $COOR_g$; or one of $R_2$, $R_3$, $R_4$, $R_5$, $R_6$, and $R_7$ is $(CR_eR_f)_n$—X—$R_c$ or O—$(CR_eR_f)_n$—X—$R_c$, and each of the others, independently, is H; n is 2; $R_c$ is heteroaryl containing at least two aromatic rings fused together or aryl substituted with $C_3$-$C_6$ alkyl, heteroaryl, or $C(O)R_j$; and $R_d$ is $COOR_j$. In these compounds, $R_c$ can be

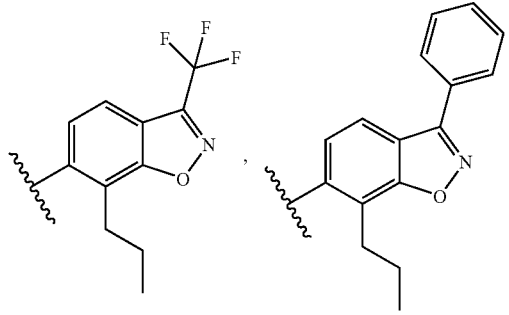

,

-continued

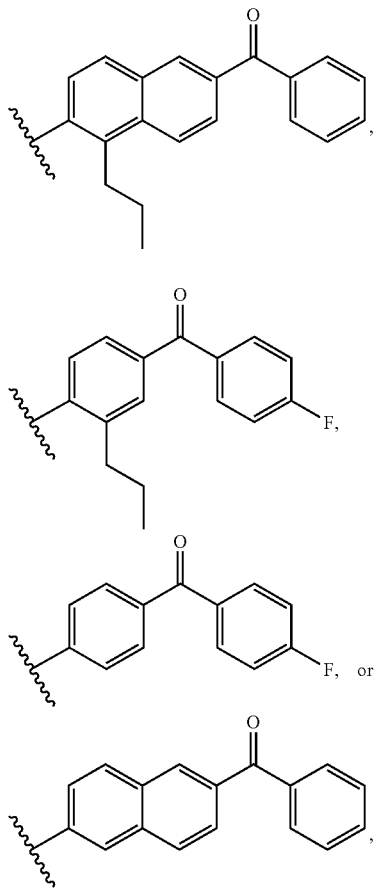

and $R_1$ can be H, $CH_2COOR$, $CH(CH_3)COOR$, $CH(CH_2CH_3)COOR$, $CH_2CH_2COOR$, $CH_2(CH_2)_2COOR$, or

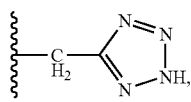

in which R is H, $C_1$-$C_6$ alkyl, aryl, or heteroaryl.

In a further aspect, this invention features a compound of formula (I) shown above except $R_1$ is $C_1$-$C_6$ alkyl, $C_3$-$C_{15}$ cycloalkyl, $C_3$-$C_{15}$ heterocycloalkyl, heteroaryl, $C(O)R_a$, $SO_2R_a$, or aryl optionally substituted with OH, $C_1$-$C_6$ alkyl, $C_3$-$C_{15}$ cycloalkyl, $C_3$-$C_{15}$ heterocycloalkyl, $C_1$-$C_6$ alkoxy, aryloxy, heteroaryloxy, heteroaryl, aryl, $NO_2$, CN, $COOR_a$, or $C(O)R_a$; in which $R_a$ is $C_1$-$C_6$ alkyl, heteroaryl, or aryl optionally substituted with $CF_3$, OH, halogen, $C_1$-$C_6$ alkoxy, aryloxy, heteroaryloxy, $C_3$-$C_{15}$ cycloalkyl, $C_3$-$C_{15}$ heterocycloalkyl, aryl, heteroaryl, $NO_2$, CN, $COOR_b$, or $C(O)R_b$; $R_b$ being H, $C_1$-$C_6$ alkyl, aryl, or heteroaryl; and one of $R_2$, $R_3$, $R_4$, $R_5$, $R_6$, and $R_7$ is $(CR_eR_f)_m$—X—$R_c$, O—$(CR_eR_f)_m$—X—$R_c$, or O—$C(R_eR_f)R_d$; and each of the others, independently, is H, OH, halogen, $C_1$-$C_6$ alkyl, $C_3$-$C_{15}$ cycloalkyl, $C_3$-$C_{15}$ heterocycloalkyl, aryl, heteroaryl, $C_1$-$C_6$ alkoxy, aryloxy, heteroaryloxy, $C_1$-$C_6$ alkylthio, arylthio, $NH_2$, $C_1$-$C_6$ alkylamino, $C_1$-$C_{12}$ dialkylamino, arylamino, diarylamino, $NO_2$, CN, $SO_3H$, $SO_2N(R_gR_h)$, $SO_2R_g$, $COOR_g$, or $C(O)R_g$; or one of $R_2$, $R_3$, $R_4$, $R_5$, $R_6$, and $R_7$ is $(CR_eR_f)_n$—X—$R_c$, O—$(CR_eR_f)_n$—X—$R_c$, or O—$C(R_eR_f)R_d$; and each of the others, independently, is H, OH, halogen, $C_3$-$C_6$ alkyl, $C_3$-$C_{15}$ cycloalkyl, $C_3$-$C_{15}$ heterocycloalkyl, aryl, heteroaryl, $C_3$-$C_6$ alkoxy, aryloxy, heteroaryloxy, $C_1$-$C_6$ alkylthio, arylthio, $NH2$, $C_1$-$C_6$ alkylamino, $C_1$-$C_{12}$ dialkylamino, arylamino, diarylamino, $NO_2$, CN, $SO_3H$, $SO_2N(R_gR_h)$, $SO_2R_g$, $COOR_g$, or $C(O)R_g$; in which m is 3-5; n is 2-5; X is $N(R_i)$, O, or S; $R_c$ is $C_1$-$C_6$ alkyl, $COOR_j$, heteroaryl, or aryl optionally substituted with OH, halogen, $C_3$-$C_6$ alkyl, $C_3$-$C_{15}$ cycloalkyl, $C_3$-$C_{15}$ heterocycloalkyl, $C_1$-$C_6$ alkoxy, aryloxy, heteroaryloxy, heteroaryl, aryl, $NO_2$, CN, $COOR_j$, or $C(O)R_j$; $R_d$ is H, OH, halogen, $NH_2$, $C_1$-$C_6$ alkylamino, $C_1$-$C_{12}$ dialkylamino, arylamino, diarylamino, $C_1$-$C_6$ alkyl, heteroaryl, $COOR_i$, or aryl optionally substituted with OH, halogen, $C_3$-$C_6$ alkyl, $C_3$-$C_{15}$ cycloalkyl, $C_3$-$C_{15}$ heterocycloalkyl, $C_1$-$C_6$ alkoxy, aryloxy, heteroaryloxy, heteroaryl, aryl, $NO_2$, CN, $COOR_j$, or $C(O)R_j$; each $R_e$, independently, is H, $C_1$-$C_6$ alkyl, aryl, or heteroaryl; each $R_f$, independently, is H, $C_1$-$C_6$ alkyl, aryl, or heteroaryl; and each of $R_g$ and $R_h$, independently, is H, $C_1$-$C_6$ alkyl, aryl, or heteroaryl; $R_i$ being $C_1$-$C_6$ alkyl, aryl, or heteroaryl; $R_j$ being H, $C_1$-$C_6$ alkyl, aryl, or heteroaryl.

Referring to formula (I), a subset of the just-described compounds are those in which $R_c$ is heteroaryl. In these compounds, $R_c$ can be pyridinyl, X can be $N(CH_3)$ or S, and $R_1$ can be $CH_2COOR$, in which R is H, $C_1$-$C_6$ alkyl, aryl, or heteroaryl.

In addition, this invention encompasses a pharmaceutical composition that contains an effective amount of at least one of the above-mentioned indole compounds and a pharmaceutically acceptable carrier. This invention also encompasses a pharmaceutical composition that contains effective amounts of at least one of the above-mentioned indole compounds and tetraethylthiuram disulfide.

The indole compounds described above are potent ligands with agonist or partial agonist activities on one or more PPARs (e.g., PPARα, PPARγ, PPARδ, PPARα/γ, or PPARα/γ/δ). The indole compounds include the compounds themselves, as well as their salts and their prodrugs, if applicable. A salt, for example, can be formed between an anion and a positively charged group (e.g., amino) on an indole compound. Examples of suitable anions include chloride, bromide, iodide, sulfate, nitrate, phosphate, citrate, methanesulfonate, trifluoroacetate, and acetate. Likewise, a salt can also be formed between a cation and a negatively charged group (e.g., carboxylate) on an indole compound. Examples of suitable cations include sodium ion, potassium ion, magnesium ion, calcium ion, and an ammonium cation such as tetramethylammonium ion. Examples of prodrugs include esters and other pharmaceutically acceptable derivatives, which, upon administration to a subject, are capable of providing active indole compounds.

Also within the scope of this invention is a composition containing one or more of the indole compounds described above for use in treating a PPAR-related disease, and the use of such a composition for the manufacture of a medicament for the just-mentioned treatment.

The details of one or more embodiments of the invention are set forth the description below. Other features, objects, and advantages of the invention will be apparent from the description and from the claims.

DETAILED DESCRIPTION
Shown below are the structures of compounds 1-175, exemplary compounds of this invention:
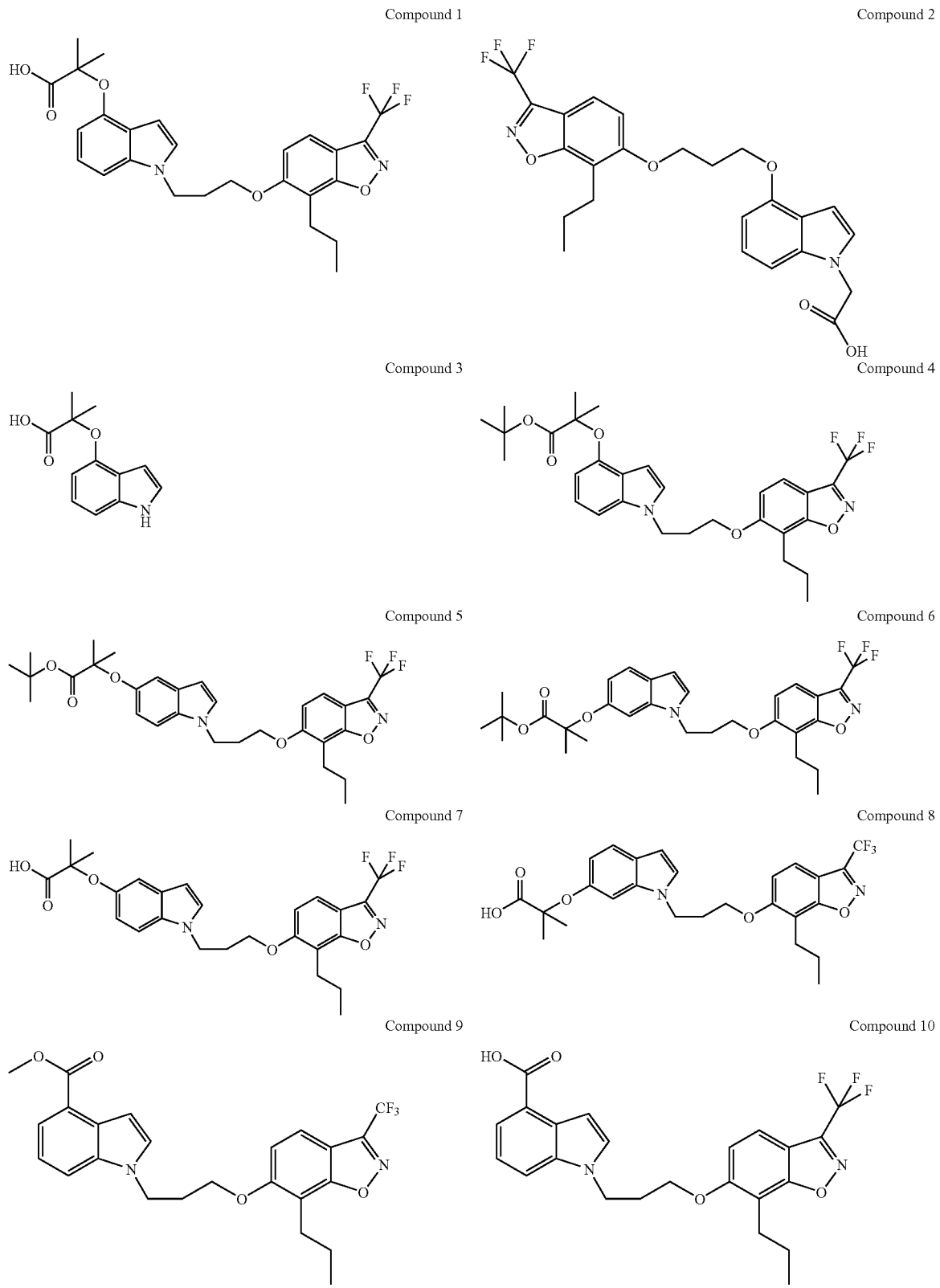

-continued
Compound 11
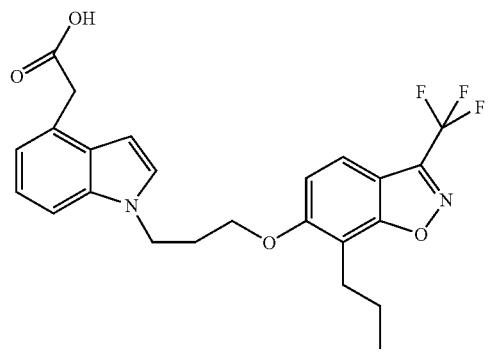
Compound 12
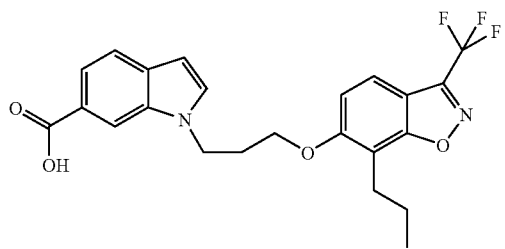
Compound 13
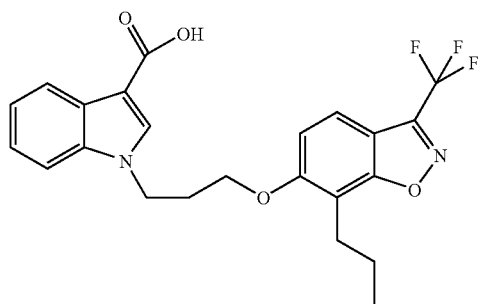
Compound 14
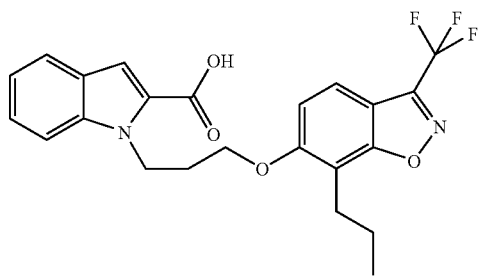
Compound 15
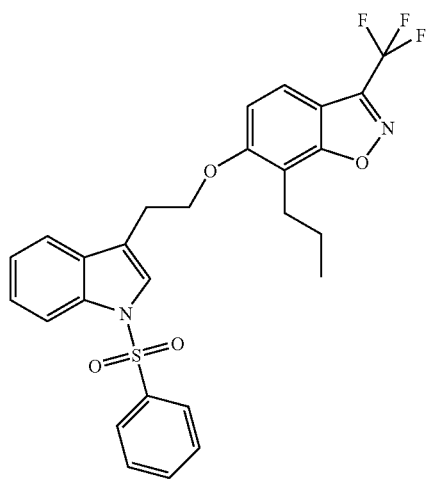
Compound 16
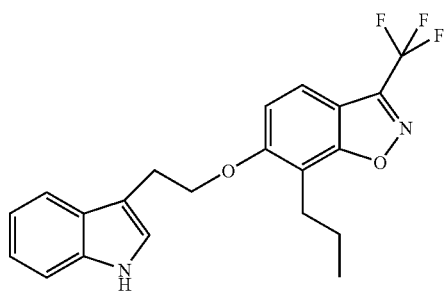
Compound 17
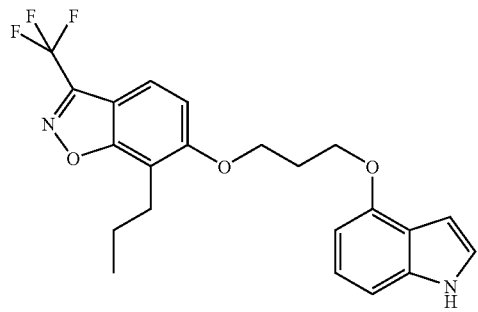
Compound 18
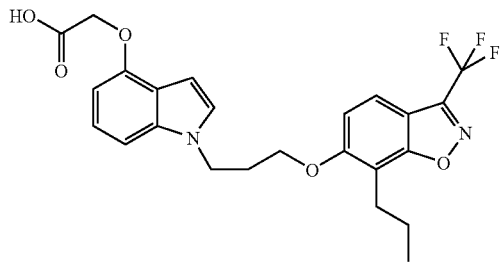

-continued
Compound 19
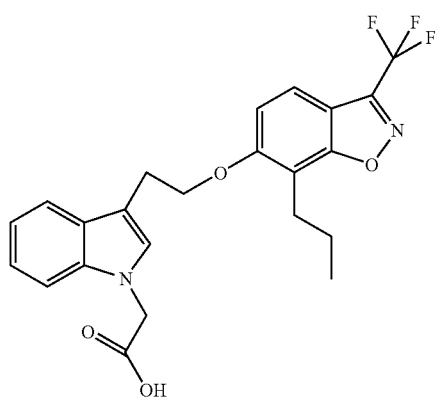
Compound 20
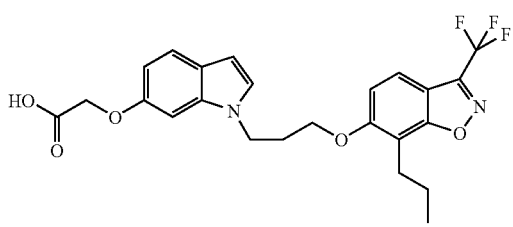
Compound 21
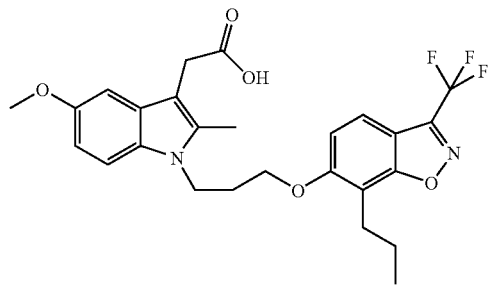
Compound 22
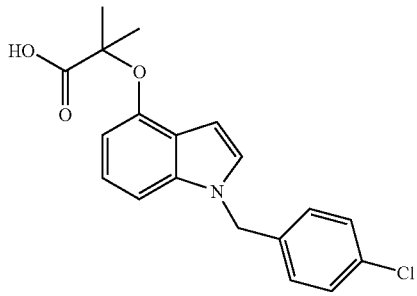
Compound 23
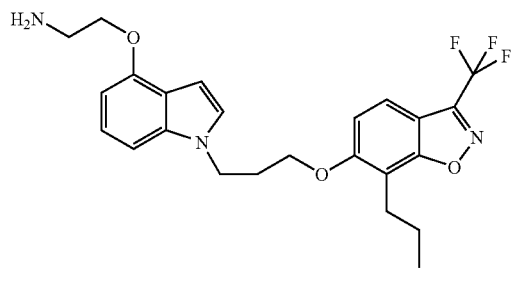
Compound 24
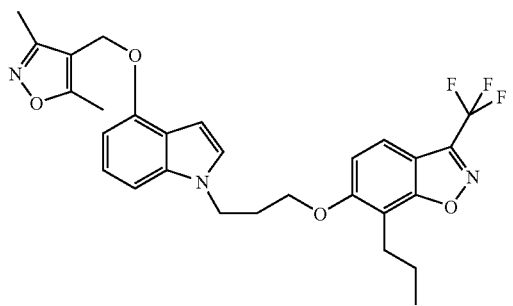
Compound 25
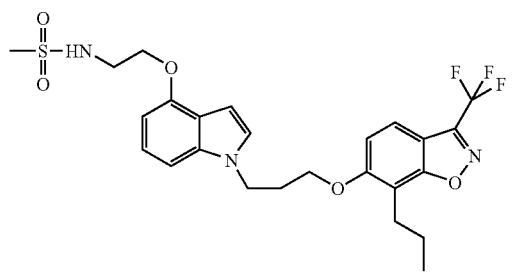
Compound 26
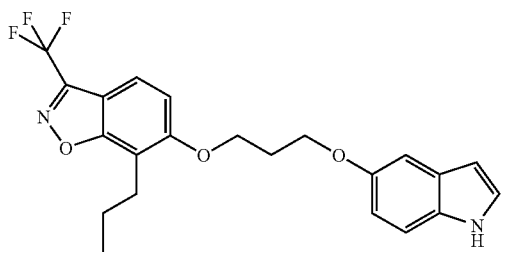

-continued
Compound 27
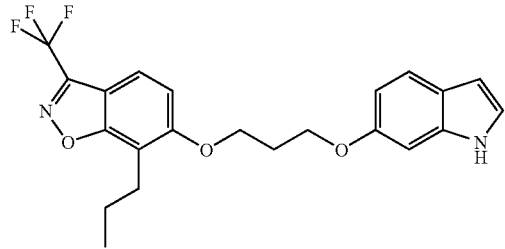
Compound 28
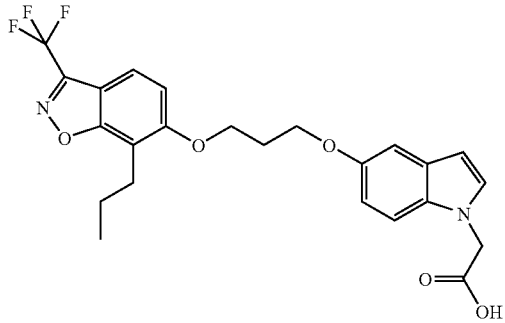
Compound 29
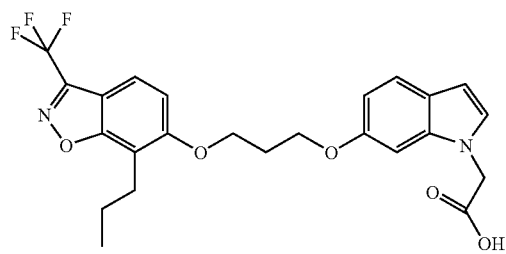
Compound 30
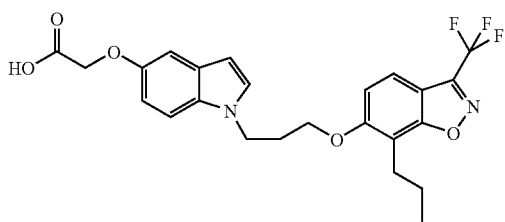
Comound 31
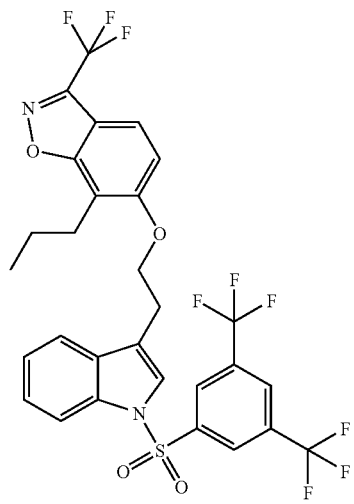
Compound 32
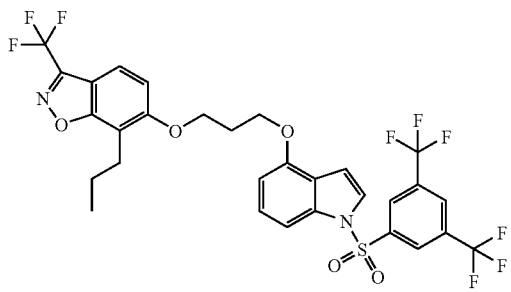
Compound 33
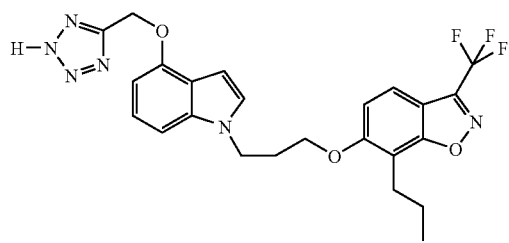
Compound 34
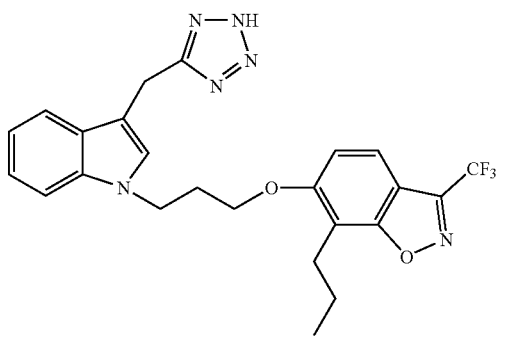

-continued
Compound 35
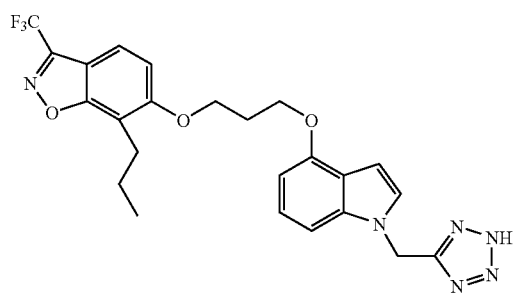
Compound 36
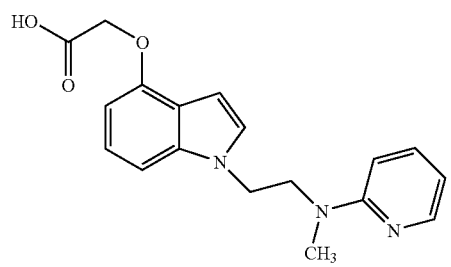
Compound 37
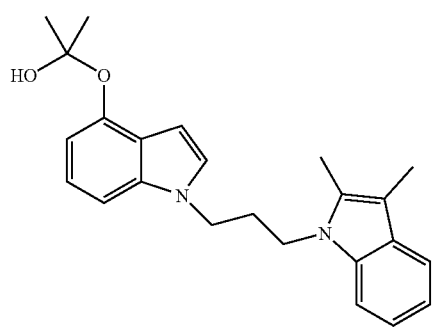
Compound 38
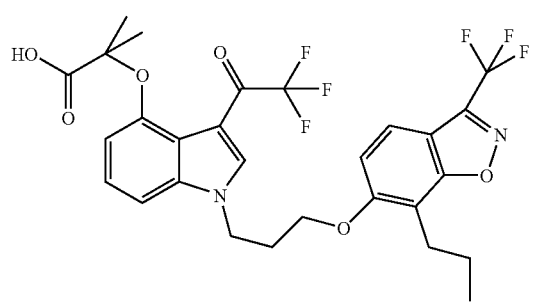
Compound 39
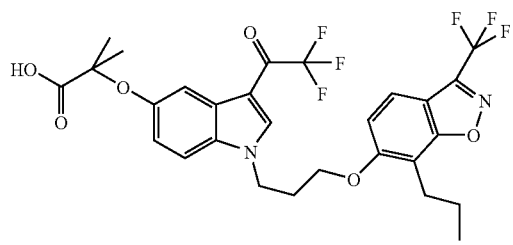
Compound 40
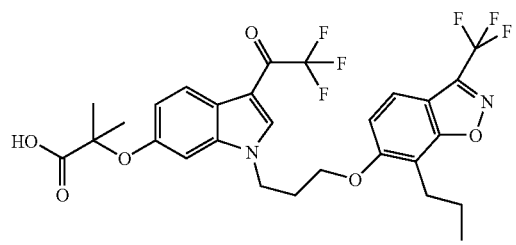
Compound 41
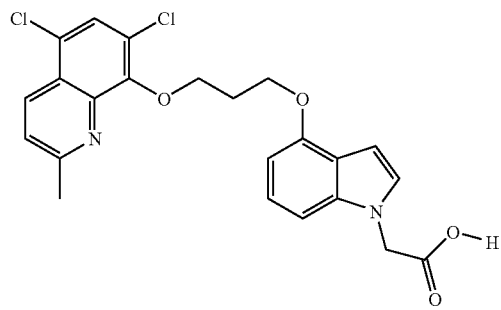
Compound 42
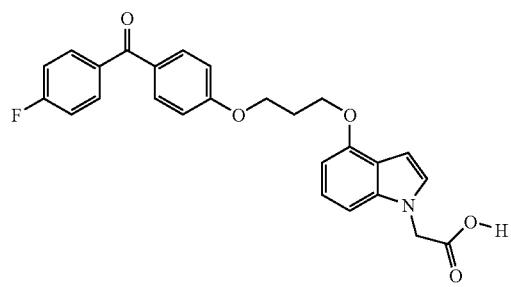
Compound 43
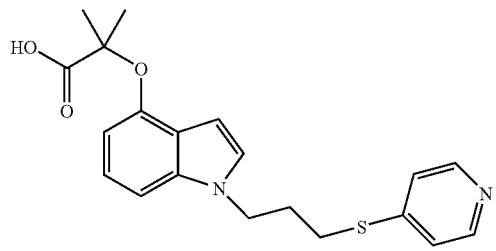
Compound 44
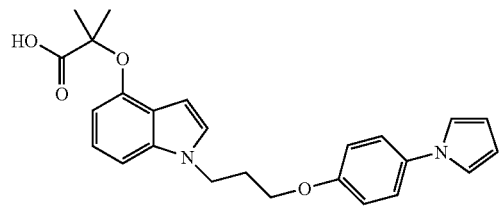

-continued
Compound 45
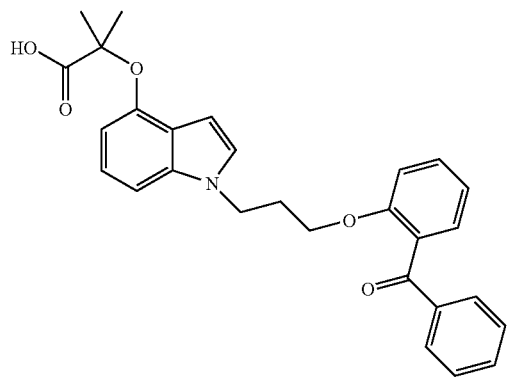
Compound 46
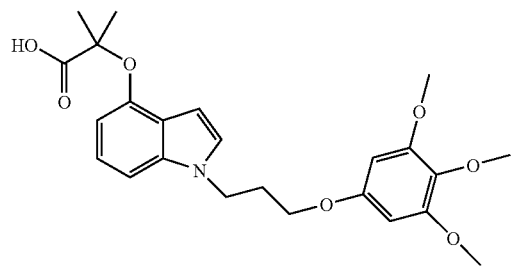
Compound 47
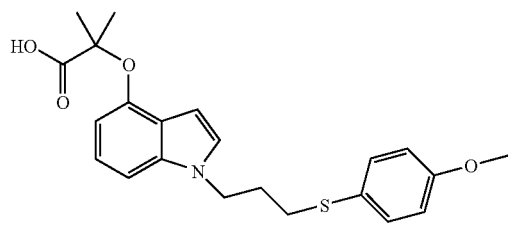
Compound 48
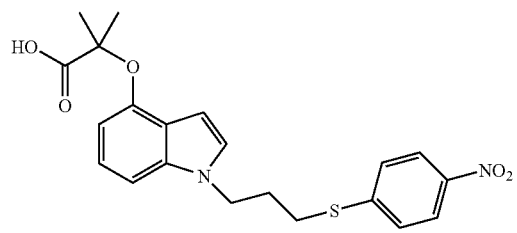
Compound 49
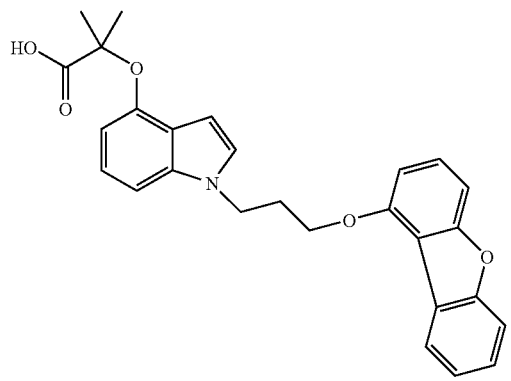
Compound 50
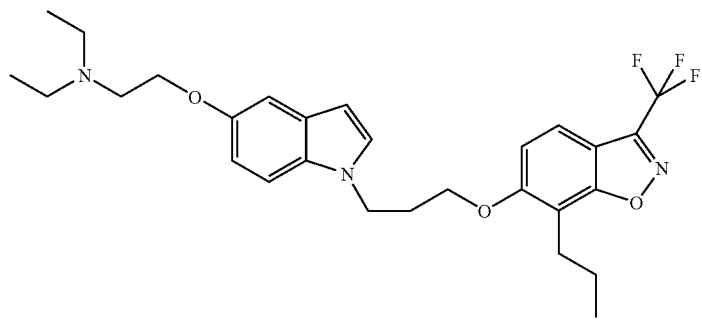

-continued
Compound 51
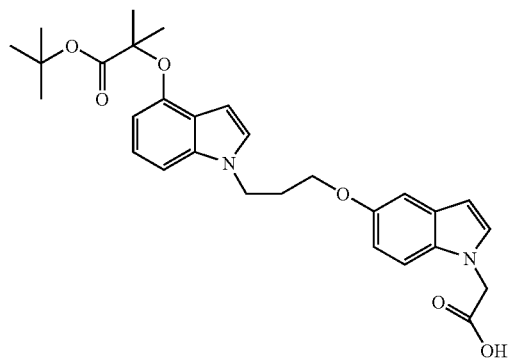
Compound 52
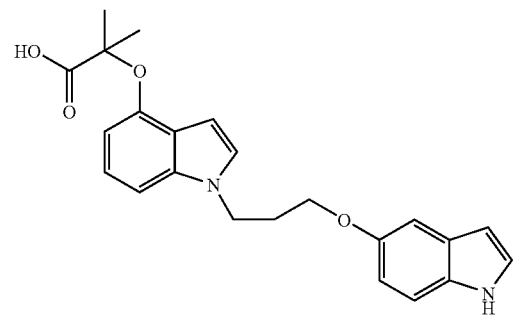
Compound 53
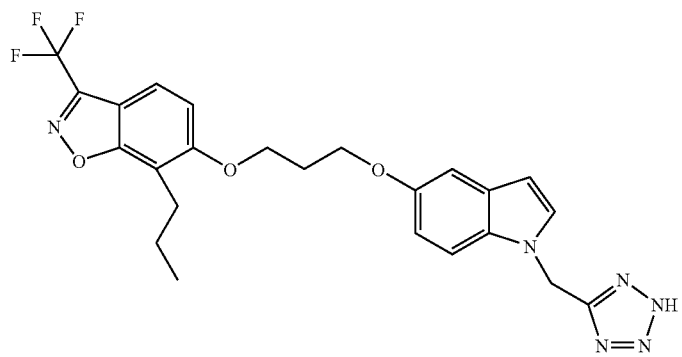
Compound 54
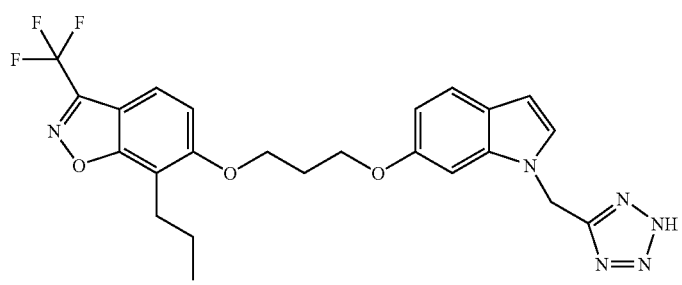
Compound 55
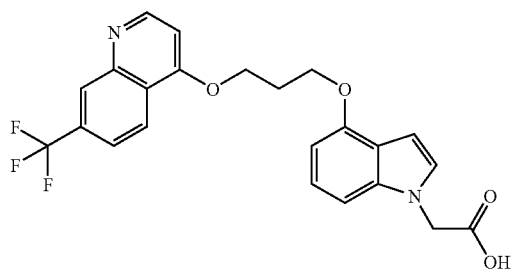
Compound 56
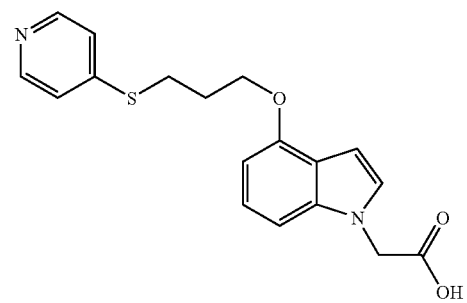
Compound 57
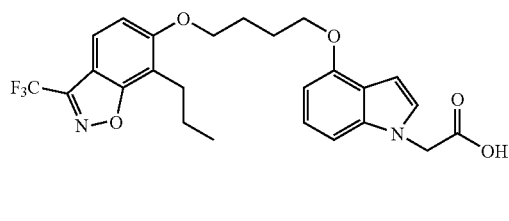
Compound 58
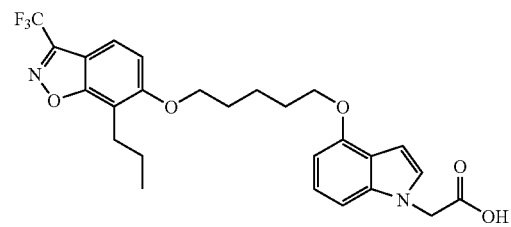

-continued
Compound 59
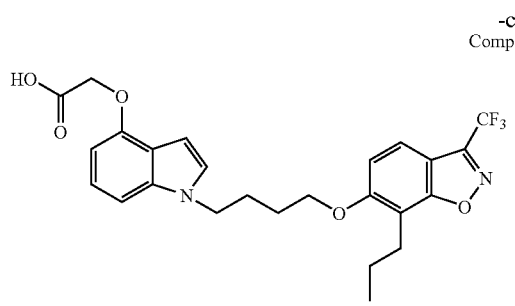
Compound 60
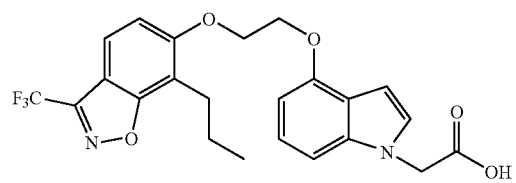
Compound 61
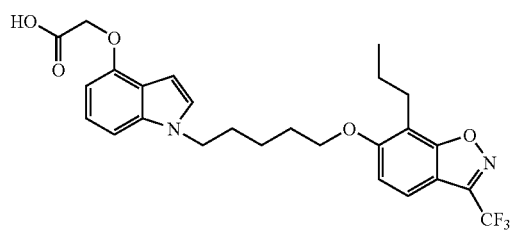
Compound 62
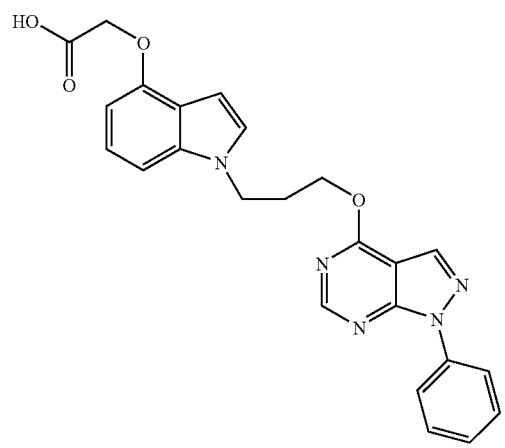
Compound 63
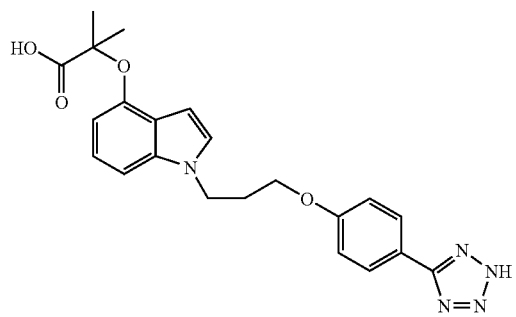
Compound 64
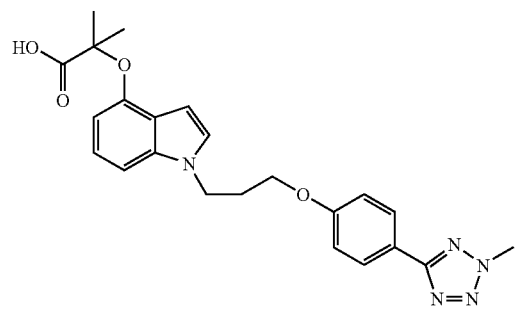
Compound 65
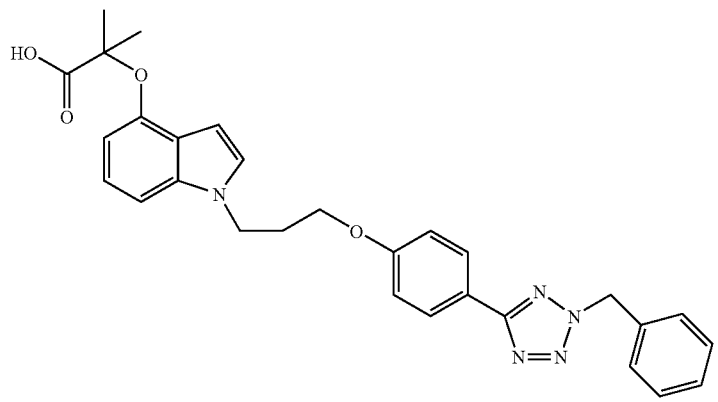

-continued
Compound 66
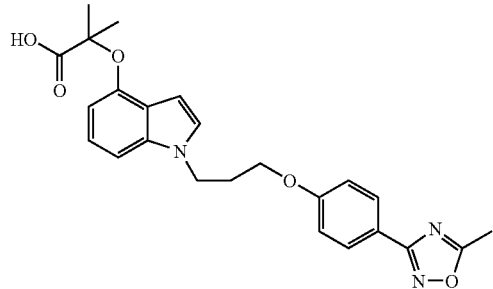
Compound 67
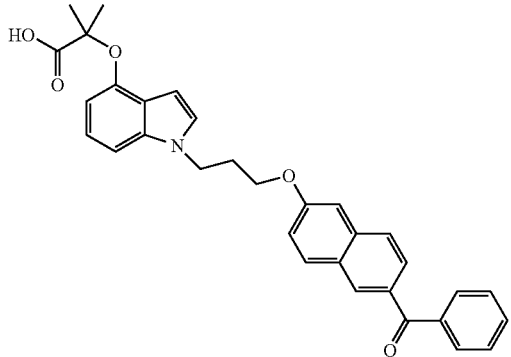
Compound 68
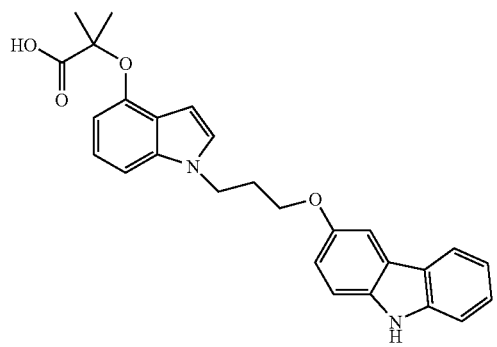
Compound 69
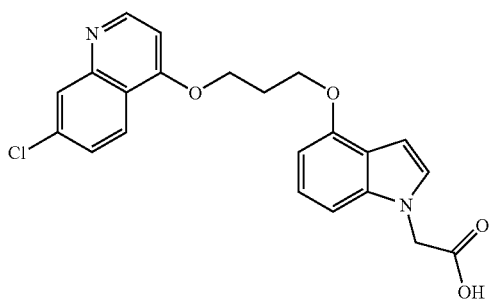
Compound 70
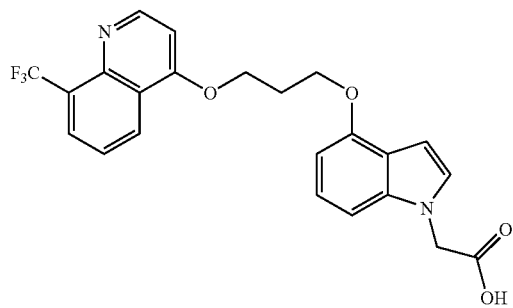
Compound 71
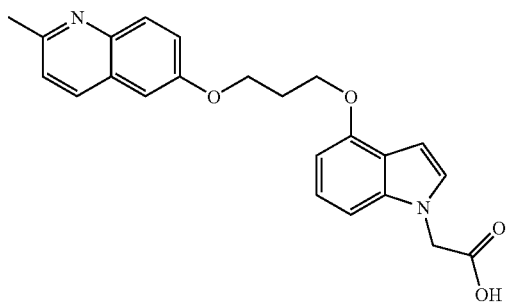
Compound 72
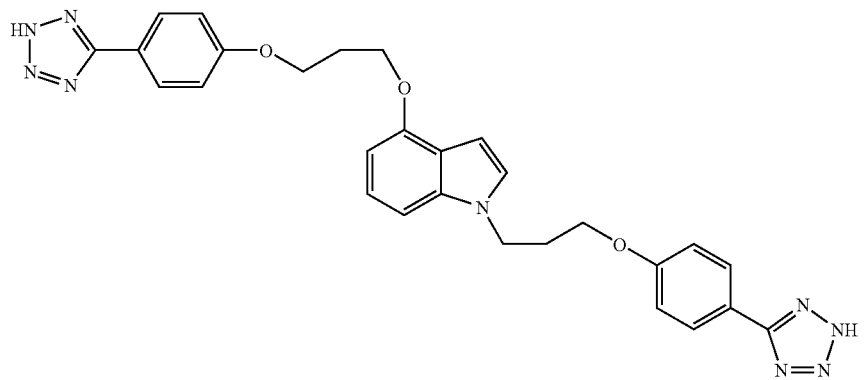

-continued
Compound 73
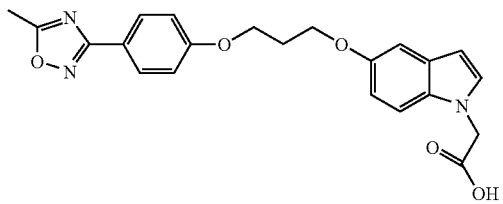
Compound 74
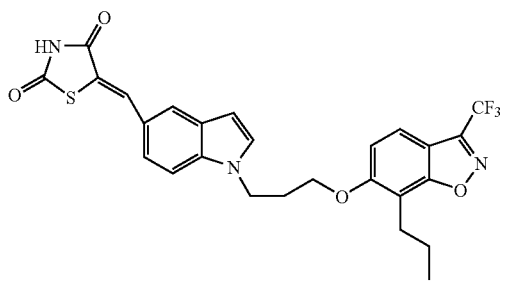
Compound 75
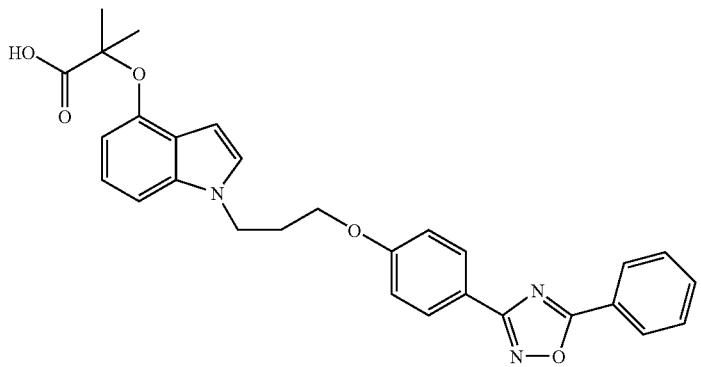
Compound 76
Compound 77
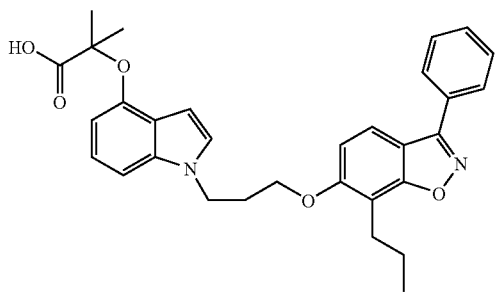
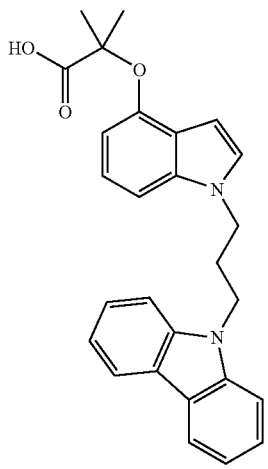
Compound 78
Compound 79
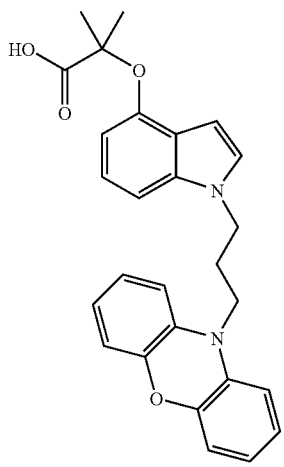
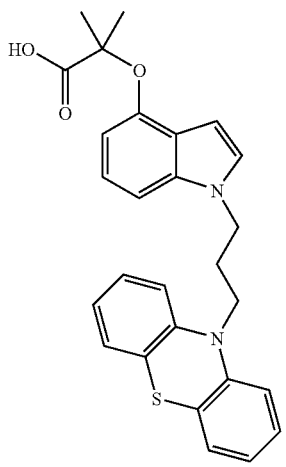

-continued
Compound 80
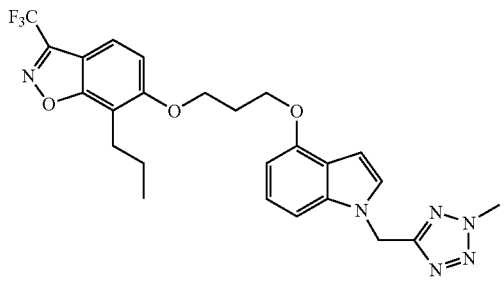
Compound 81
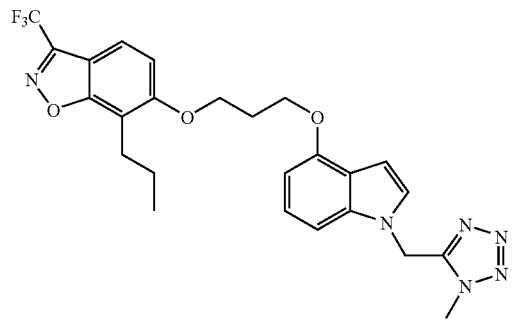
Compound 82
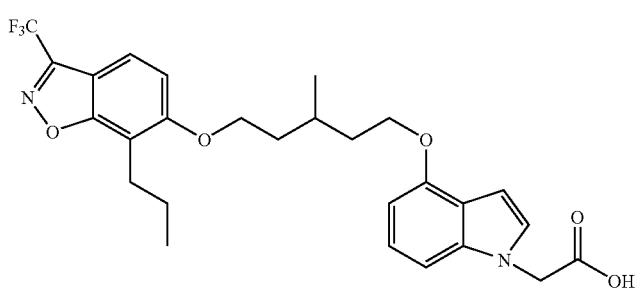
Compound 83
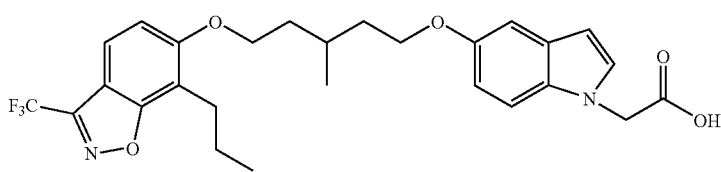
Compound 84
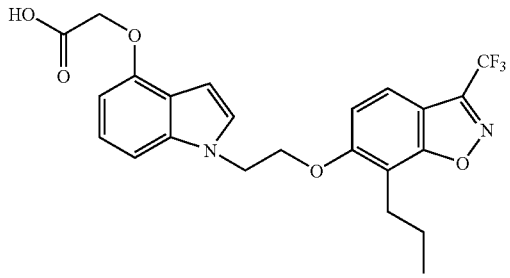
Compound 85
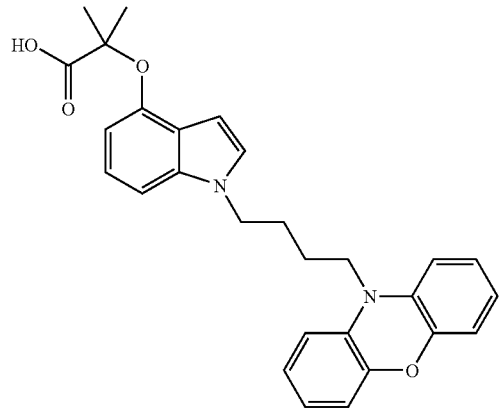
Compound 86
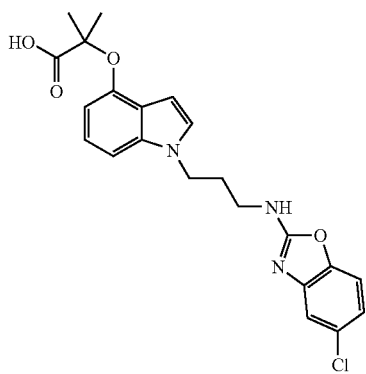
Compound 87
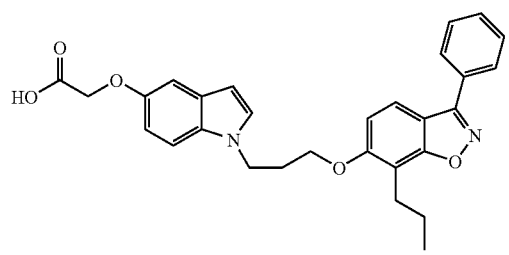

-continued
Compound 88
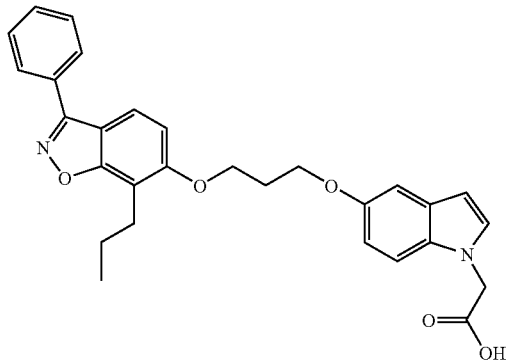
Compound 89
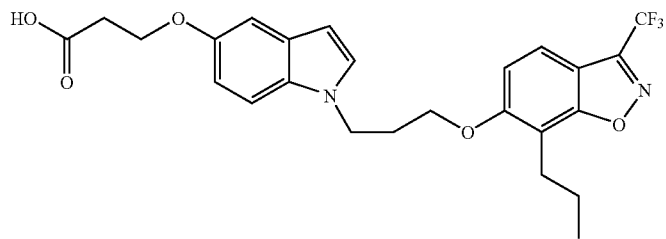
Compound 90
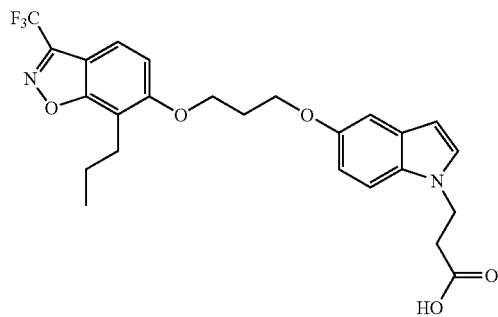
Compound 91
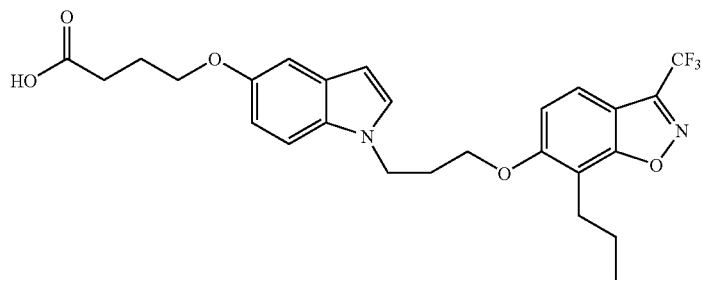
Compound 92
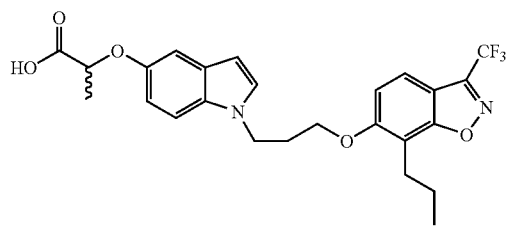
Compound 93
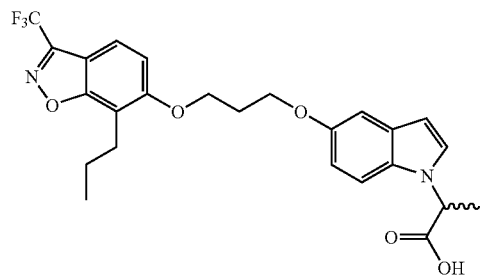

-continued
Compound 94
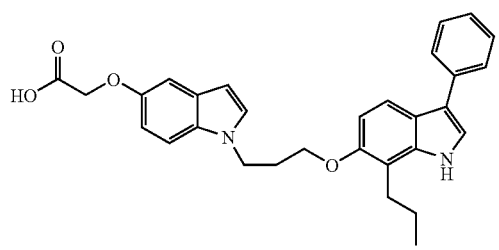
Compound 95
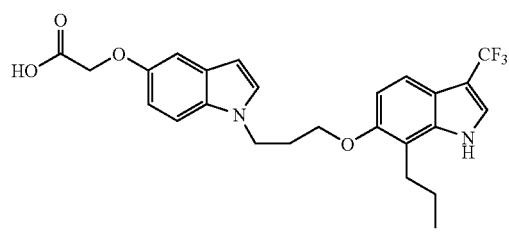
Compound 96
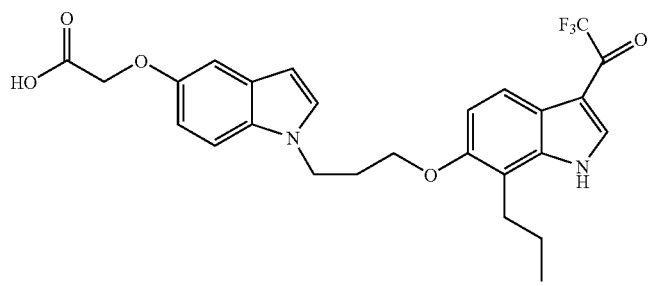
Compound 97
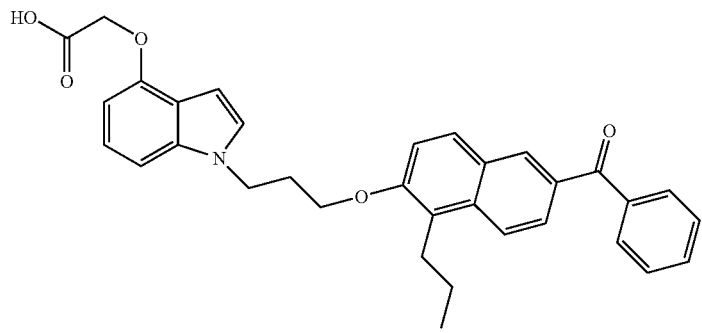
Compound 98
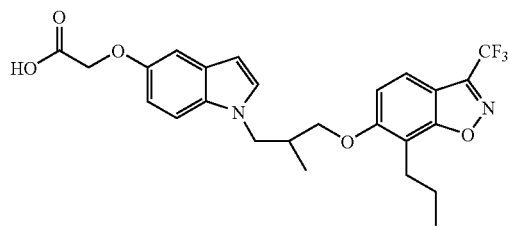
Compound 99
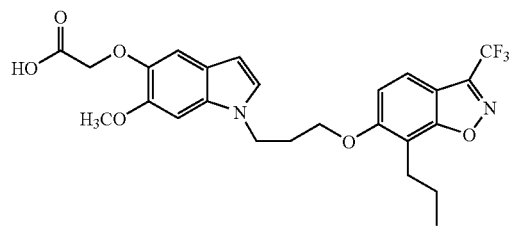
Compound 100
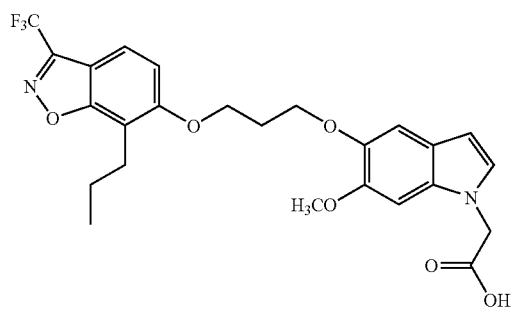
Compound 101
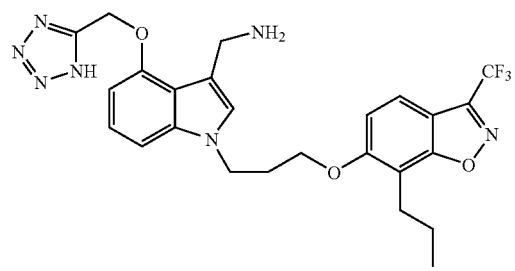

-continued
Compound 102
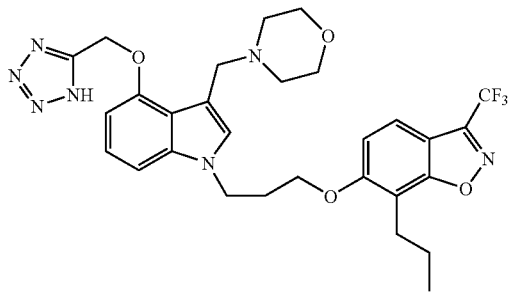
Compound 103
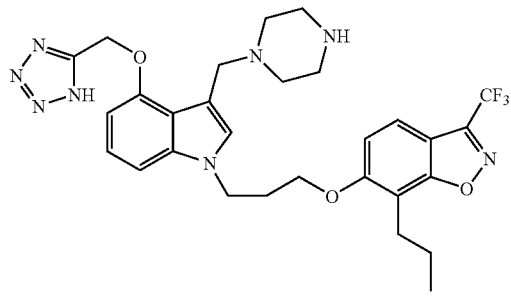
Compound 104
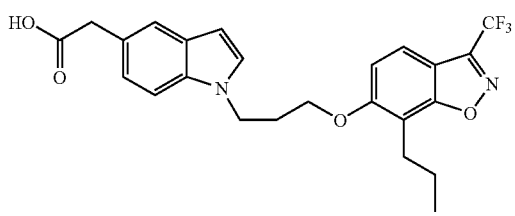
Compound 105
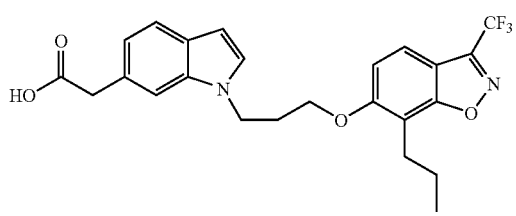
Compound 106
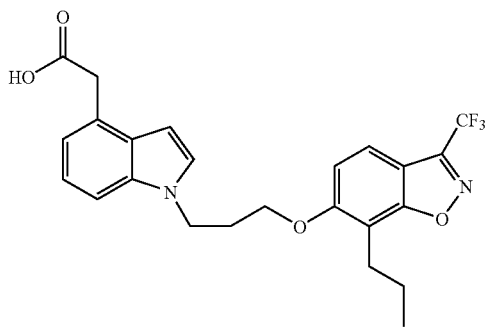
Compound 107
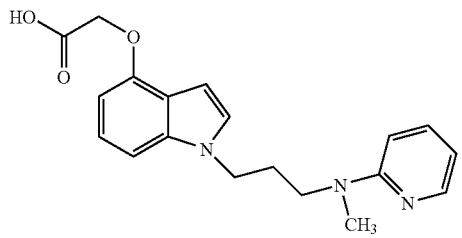
Compound 108
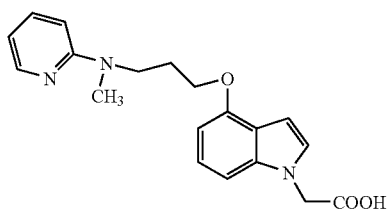
Compound 109
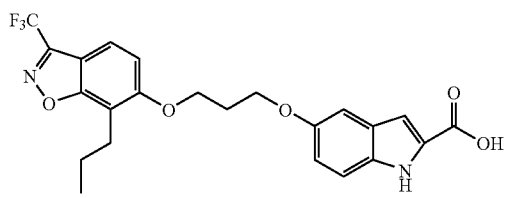
Compound 110
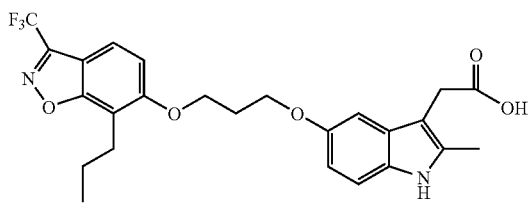
Compound 111
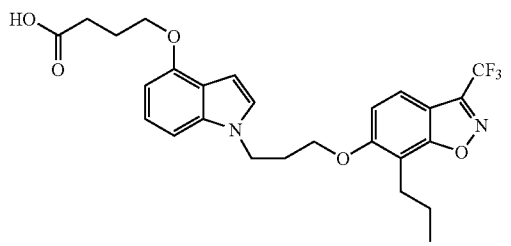

Compound 112
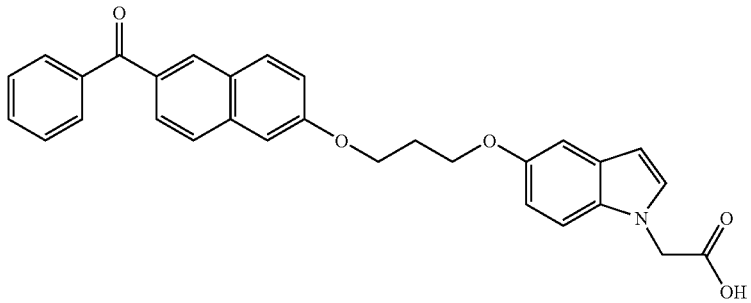
Compound 113
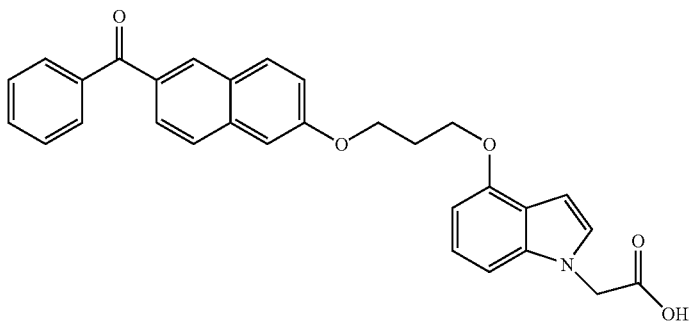
Compound 114
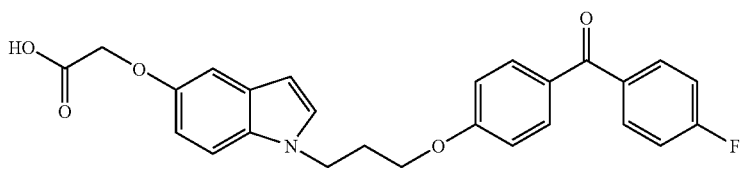
Compound 115
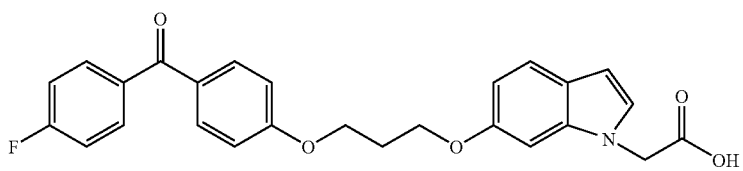
Compound 116
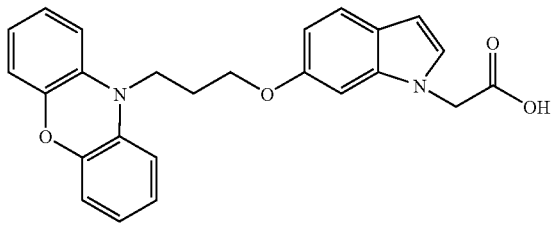
Compound 117
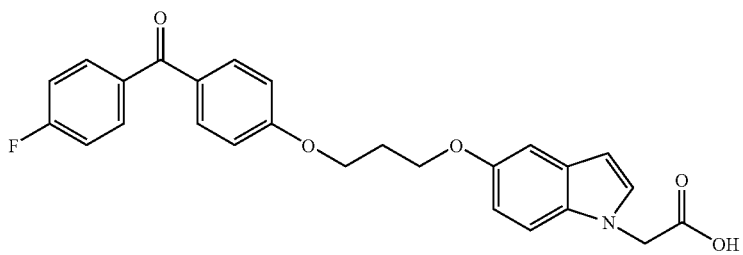

-continued
Compound 118
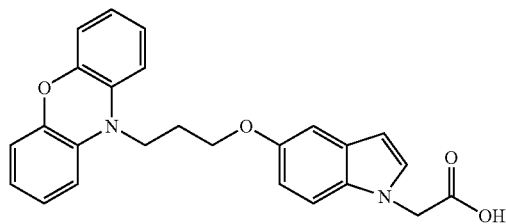
Compound 119
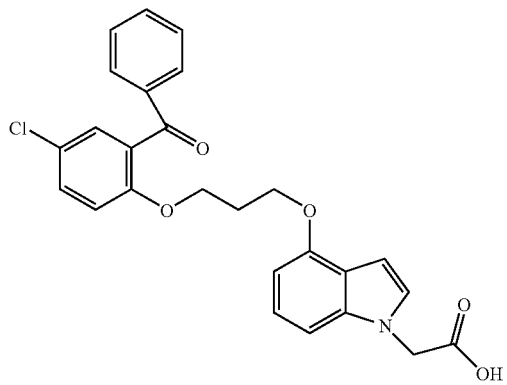
Compound 120
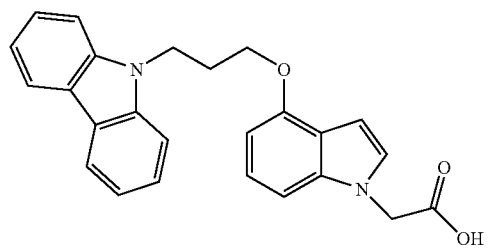
Compound 121
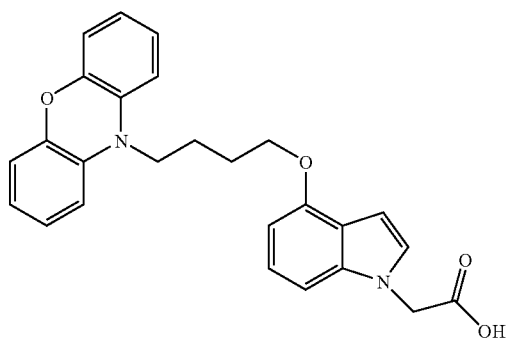
Compound 122
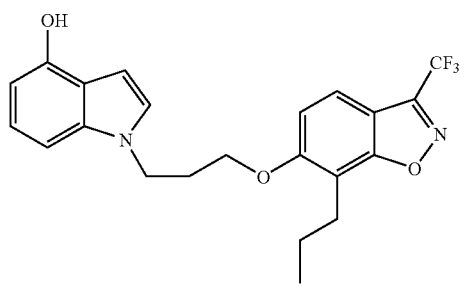
Compound 123
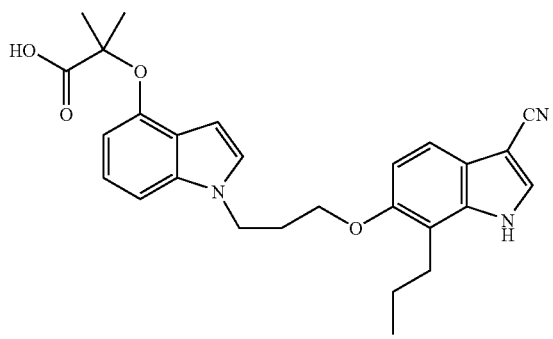
Compound 124
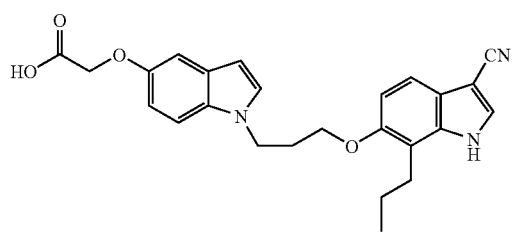
Compound 125
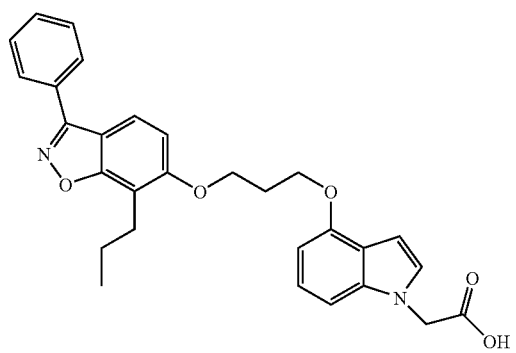

-continued
Compound 126
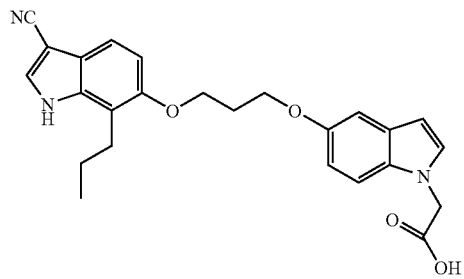
Compound 127
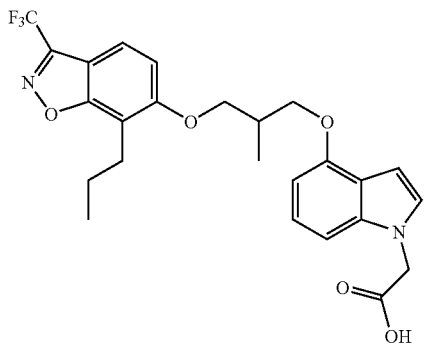
Compound 128
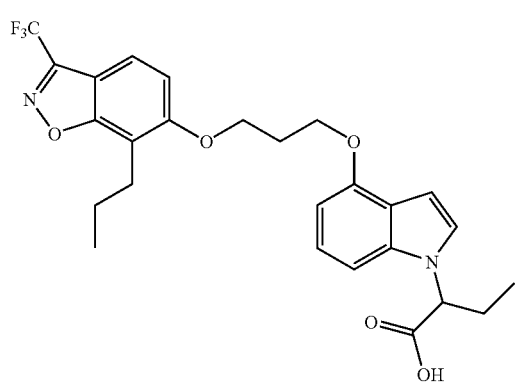
Compound 129
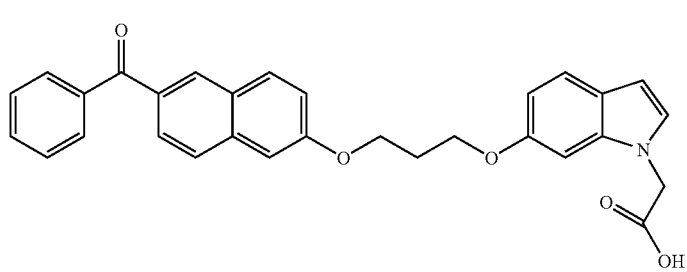
Compound 130
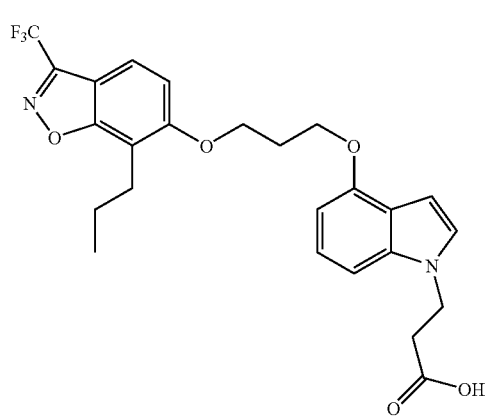

-continued
Compound 131
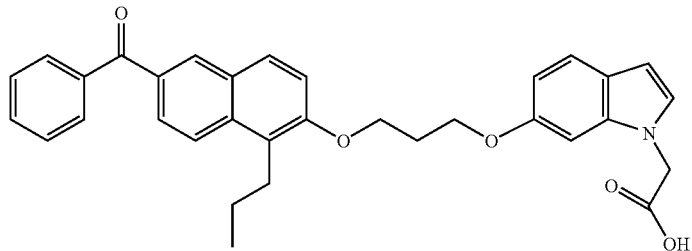
Compound 132
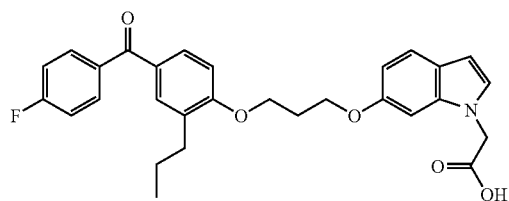
Compound 133
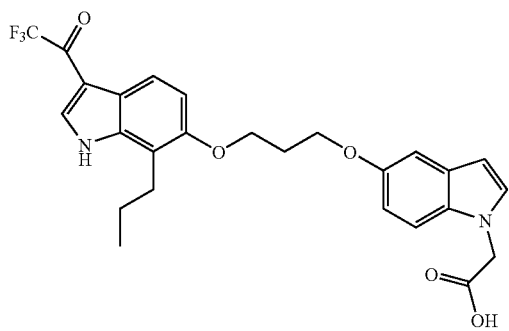
Compound 134
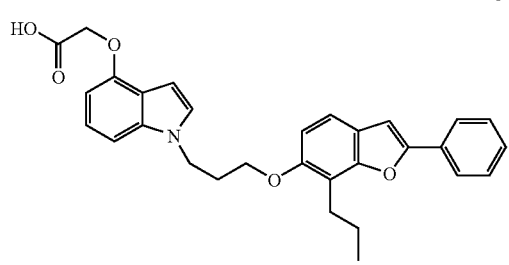
Compound 135
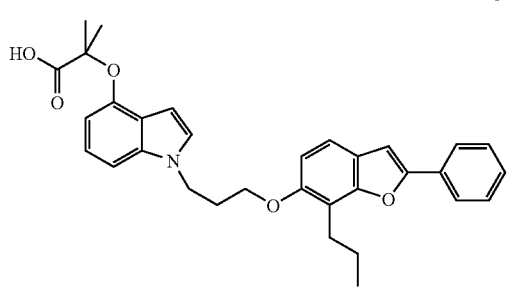
Compound 136
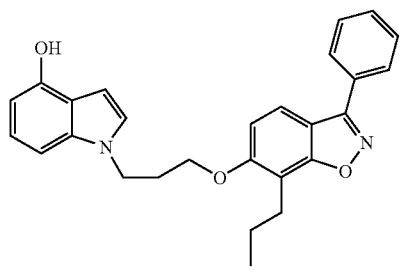
Compound 137
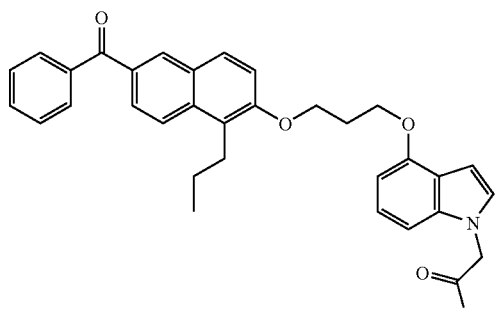
Compound 138
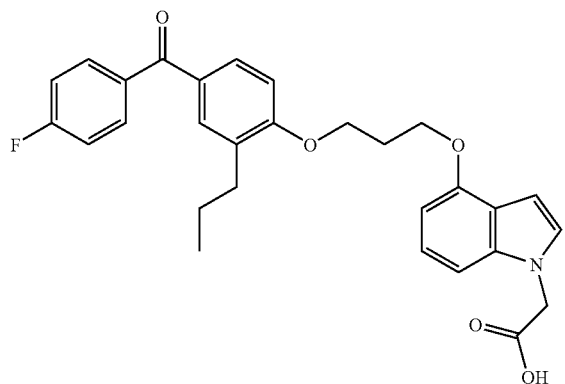

-continued
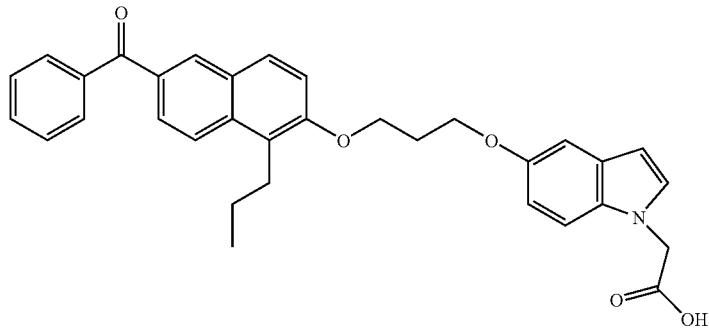
Compound 139
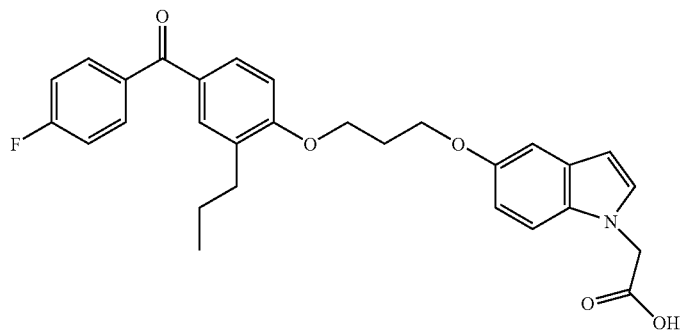
Compound 140
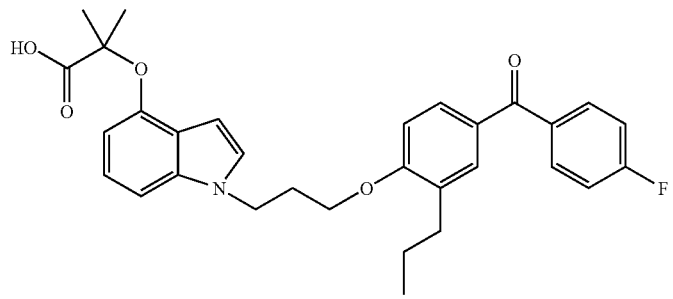
Compound 141
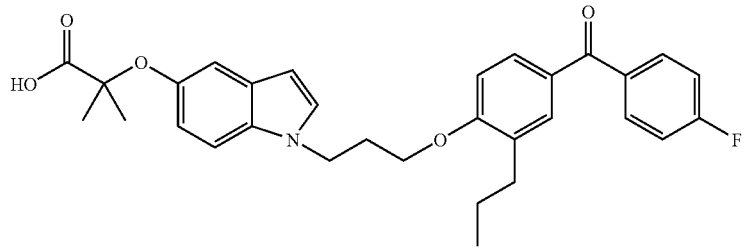
Compound 142
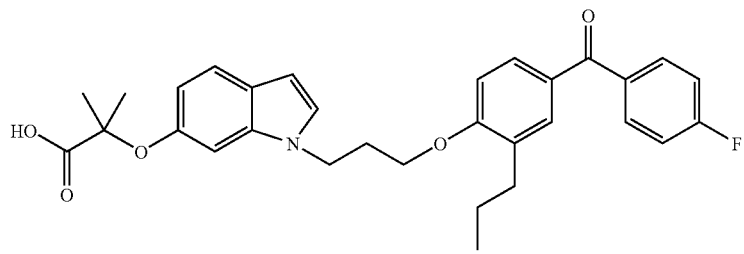
Compound 143

-continued
Compound 144
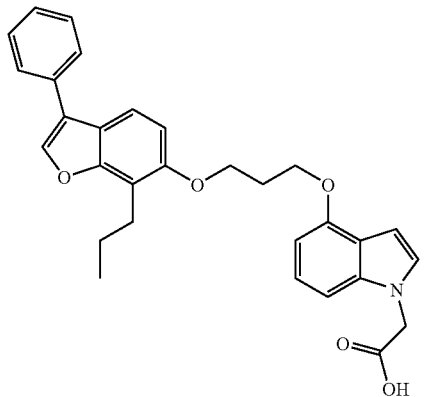
Compound 145
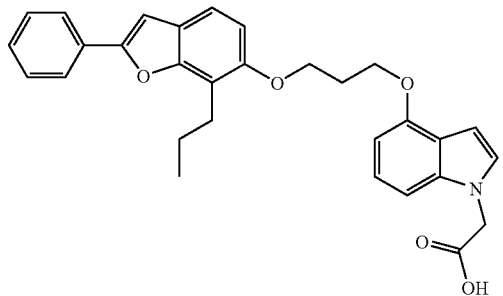
Compound 146
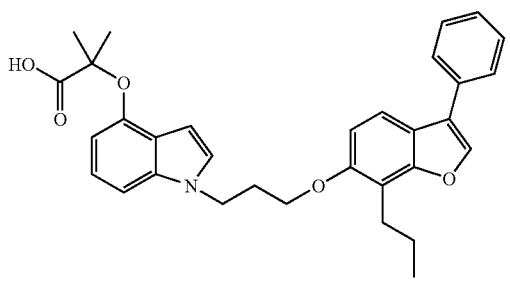
Compound 147
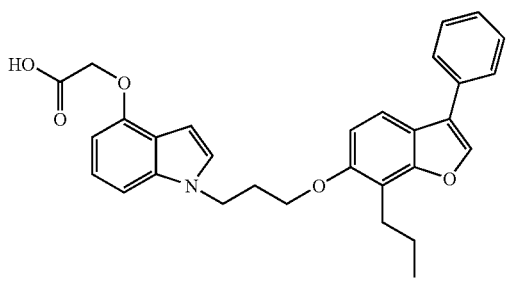
Compound 148
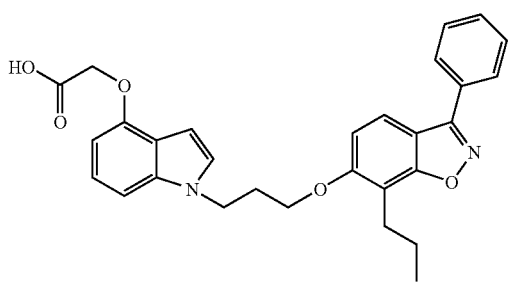
Compound 149
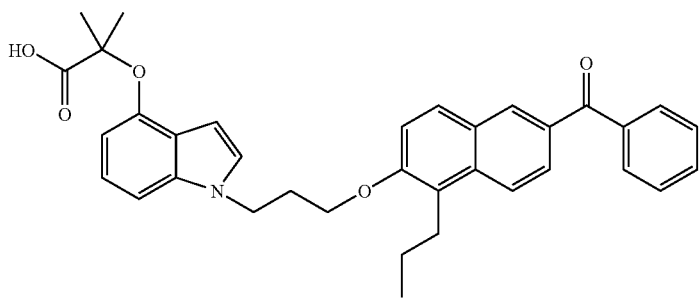
Compound 150
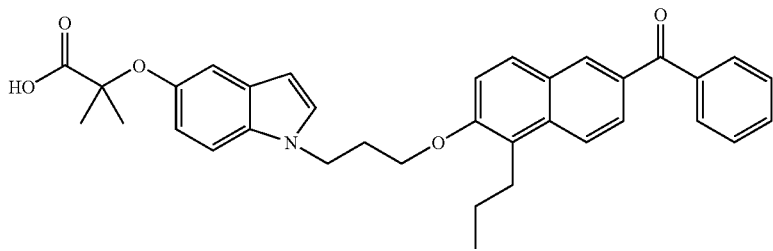

Compound 151
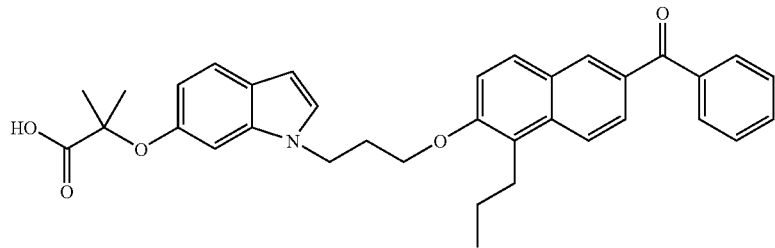
Compound 152
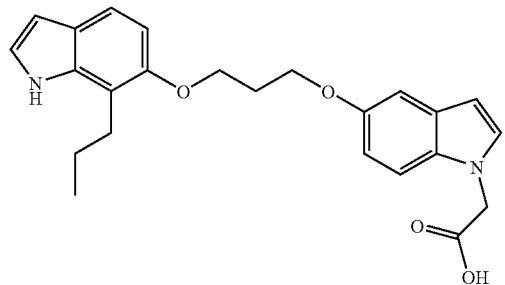
Compound 153
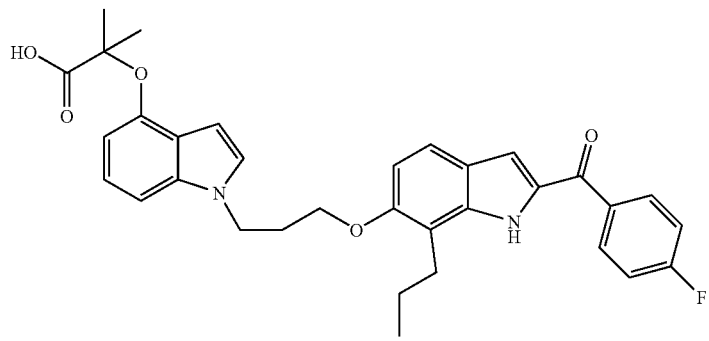
Compound 154
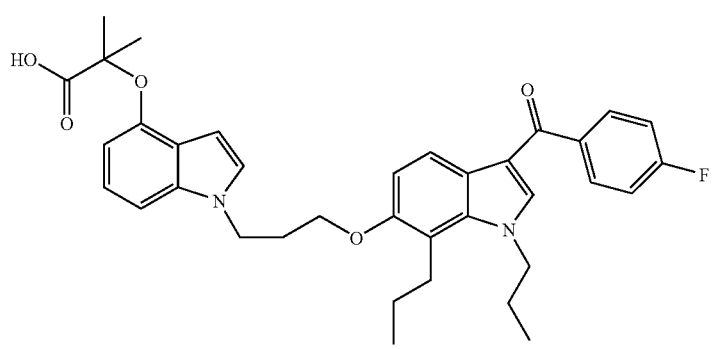

-continued
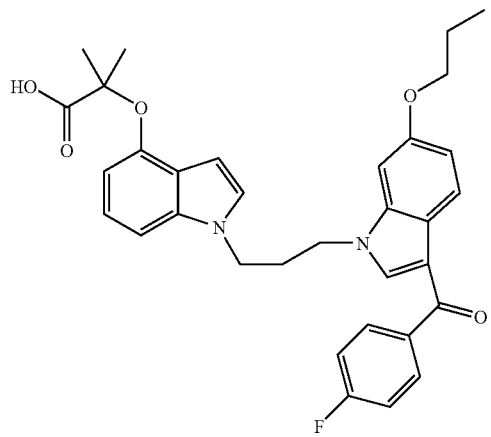
Compound 155
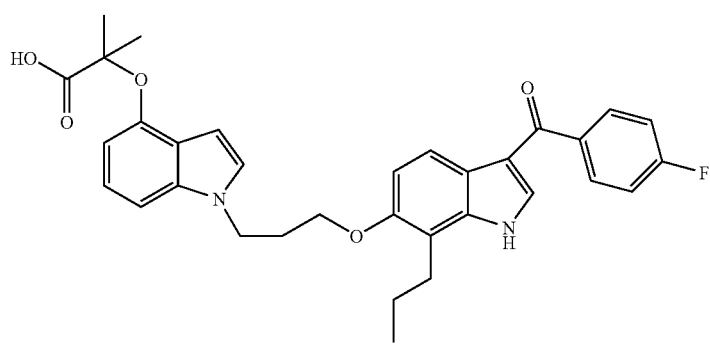
Compound 156
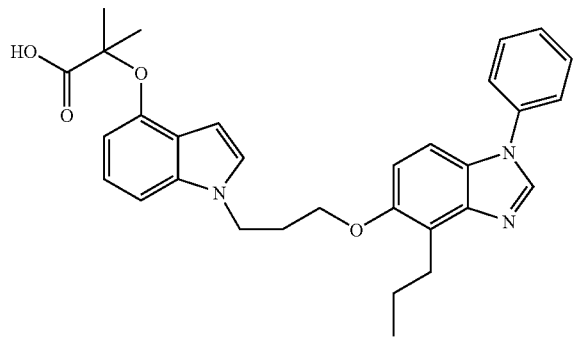
Compound 157
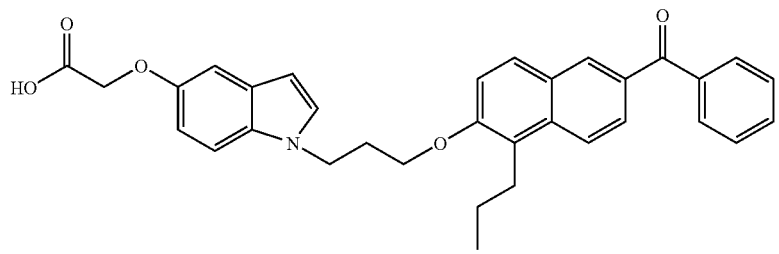
Compound 158
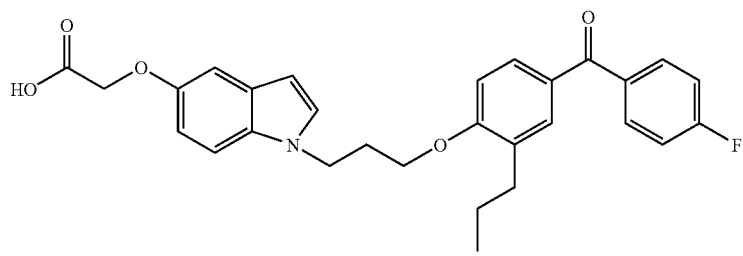
Compound 159

-continued
Compound 160
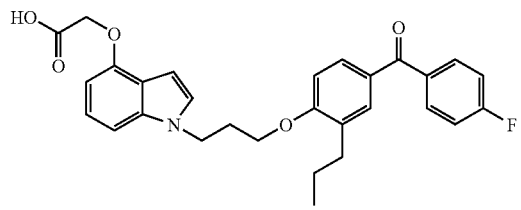
Compound 161
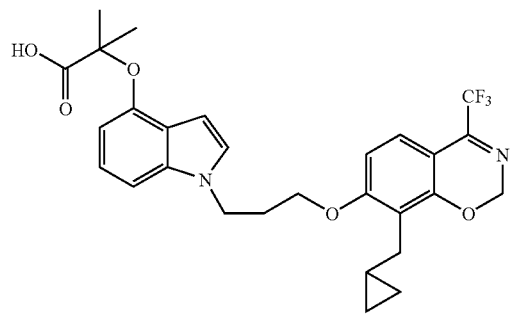
Compound 162
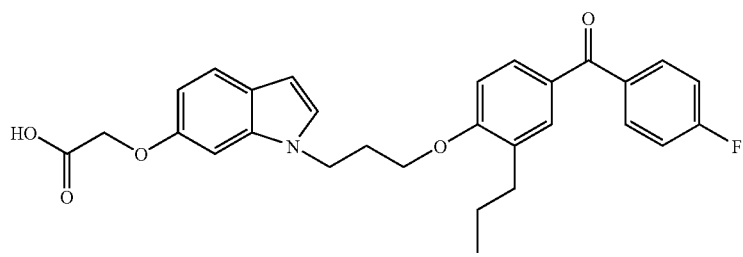
Compound 163
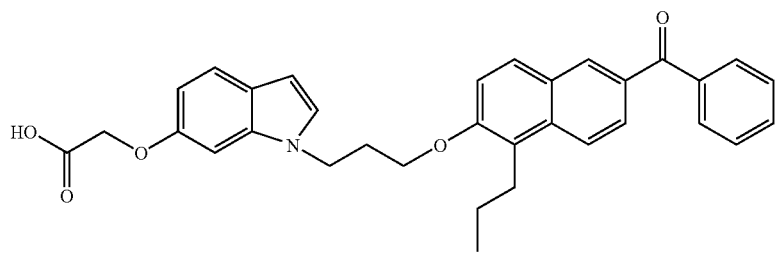
Compound 164
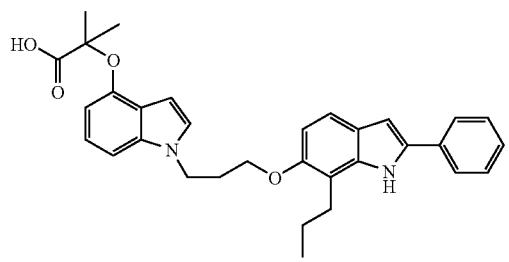
Compound 165
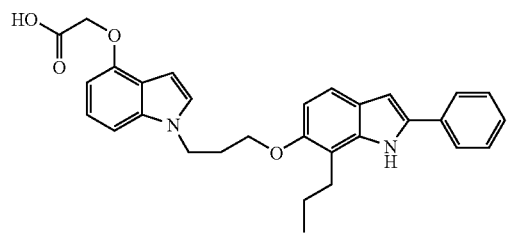
Compound 166
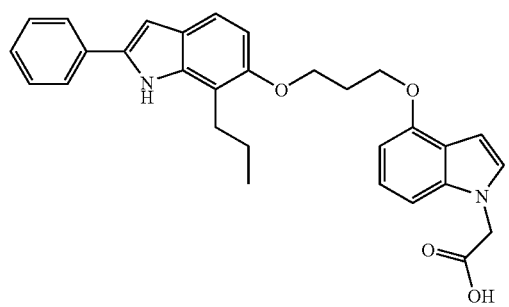
Compound 167
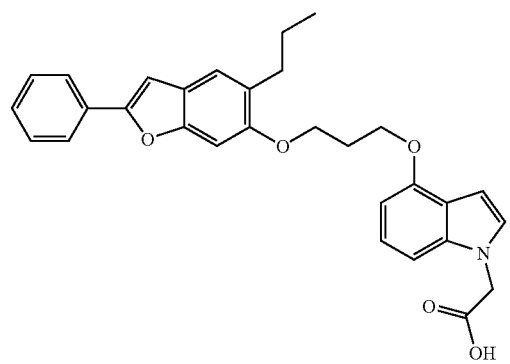

-continued
Compound 168
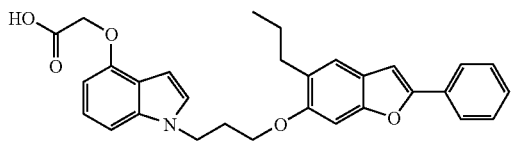
Compound 169
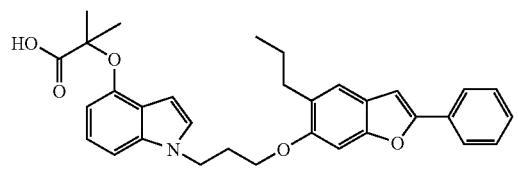
Compound 170
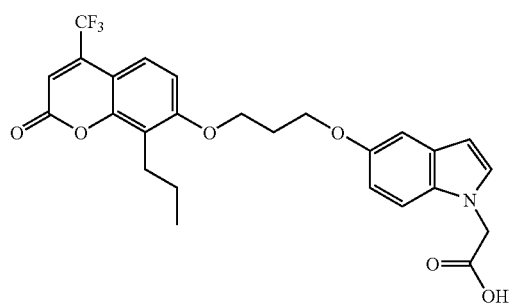
Compound 171
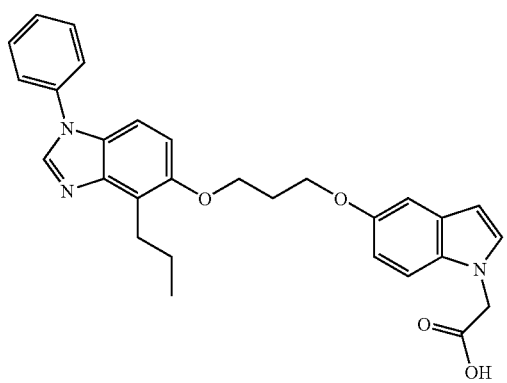
Compound 172
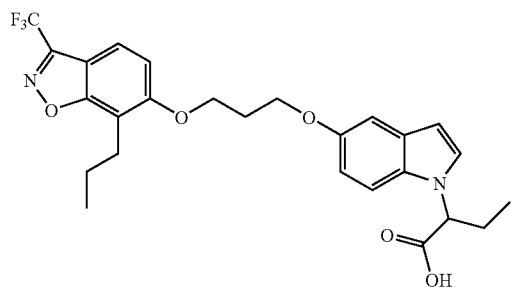
Compound 173
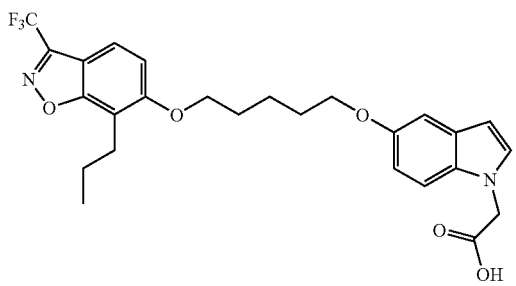
Compound 174
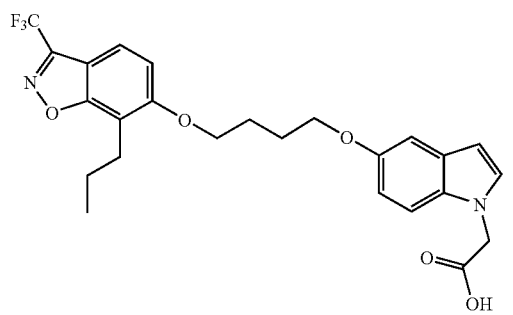
Compound 175
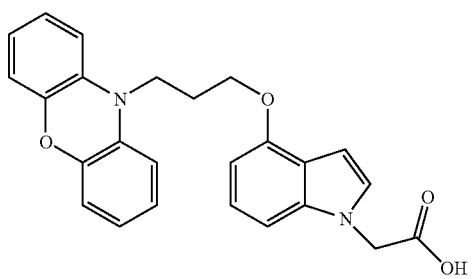

The indole compounds described above can be prepared by methods well known to a skilled person in the art. For example, scheme I and II shown below depict two typical synthetic routes for synthesizing exemplary indole compounds. Details of preparation of these compounds are provided in Examples 1-175.

Scheme I:

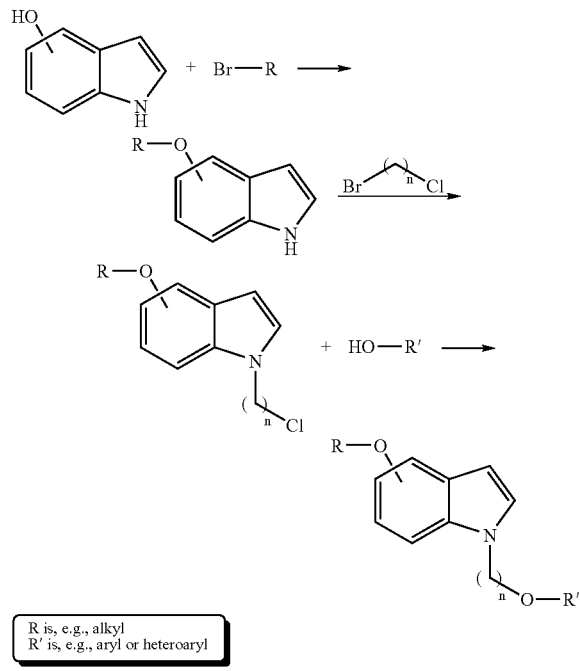

Scheme II:

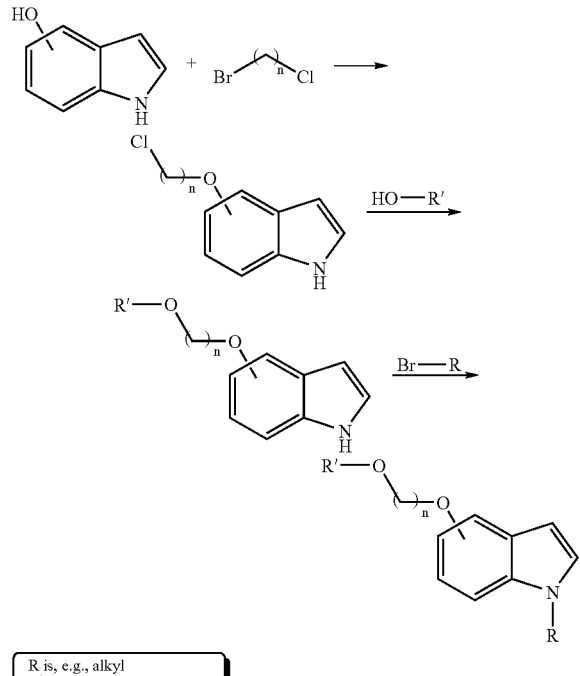

As shown in Scheme I, hydroxyindole can react with a bromo-containing alkyl substituted with various functional groups (e.g., COOCH$_2$CH$_3$) in the presence of 1 equivalent of base to yield an alkoxy-substituted indole. An indole compound of the invention can be prepared by treating the alkoxy-substituted indole with a linker compound containing a bromo group and a chloro group, followed by treating with an aromatic compound containing a hydroxy group. Alternatively, as shown in Scheme II, hydroxyindole can first react with a linker compound in the presence of 1 equivalent of base, followed by an aromatic compound containing a hydroxy group to yield an alkoxy-substituted indole. Then, the alkoxy-substituted indole can react with a bromo-containing alkyl substituted with various functional groups to afford an indole compound of the invention.

Other indole compounds can be prepared using other suitable starting materials following the synthetic routes disclosed herein and other synthetic methods known in the art. The methods described above may also additionally include steps, either before or after the steps described specifically herein, to add or remove suitable protecting groups in order to ultimately allow synthesis of the indole compounds. In addition, various synthetic steps may be performed in an alternate sequence or order to give the desired compounds. Synthetic chemistry transformations and protecting group methodologies (protection and deprotection) useful in synthesizing applicable indole compounds are known in the art and include, for example, those described in R. Larock, Comprehensive Organic Transformations, VCH Publishers (1989); T. W. Greene and P. G. M. Wuts, Protective Groups in Organic Synthesis, 2nd Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995) and subsequent editions thereof.

The indole compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

Also within the scope of this invention is a pharmaceutical composition contains an effective amount of at least one indole compound described above and a pharmaceutical acceptable carrier. Further, this invention covers a method of administering an effective amount of one or more of the indole compounds to a patient with a PPAR-related disease. Effective doses will vary, as recognized by those skilled in the art, depending on the types of diseases treated, route of administration, excipient usage, and the possibility of co-usage with other therapeutic treatment.

The indole compounds described above may be administered alone or may be administered concurrently with other therapeutic agents. Examples of such a therapeutic agent include a lipid lowering agent, an antidiabetic agent (e.g., sulfonylurea or biguanides), α-glucosidase inhibitors, or insulin or other insulin secretagogues. An example of a lipid lowering drug is a cholesterol biosynthesis inhibitor, particularly a 3-hydroxy-3-methyl-glutaryl coenzyme A reductase inhibitor (e.g., lovastatin, simvastatin, pravastatin, fluvastatin, atorvastatin, rivastatin, itavastatin, or rosuvastatin). Other lipid lowering drugs include cholesterol absorption inhibitors (e.g., stanol esters, sterol glycosides such as tiqueside, or azetidinones such as ezetimibe), cholesterol O-acyltransferase inhibitors (e.g., avasimibe), niacin, bile acid sequestrants, microsomal triglyceride transport inhibitors, or bile acid reuptake inhibitors.

In addition, a composition containing tetraethylthiuram disulfide (disulfiram, ANTABUSE™) and a PPAR agonist shows synergistic effect in binding to PPAR. Specifically, tetraethylthiuram disulfide alone is a poor PPAR agonist. However, a combination of tetraethylthiuram disulfide and a PPAR agonist (e.g., rosiglitazone, pioglitazone, or an indole compound described above) shows greater activity in binding to PPAR than the PPAR agonist alone. For example, a solution containing 0.5, µM rosiglitazone and 10 µM tetraethylthiuram disulfide exhibits 5 times greater PPARγ transactivation activity than a solution containing 0.5 µM rosiglitazone alone. As another example, a solution containing 10 µM compound 1 and 10 µM tetraethylthiuram disulfide exhibits at least 3 times greater PPARγ transactivation activity than a solution containing 10 µM compound 1 alone.

To practice the method of the present invention, a composition having one or more indole compounds can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having one or more active indole compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active indole compound. Examples of other carriers include colloidal silicon oxide, magnesium stearate, cellulose, sodium lauryl sulfate, and D&C Yellow #10.

The indole compounds of this invention can be preliminarily screened for their efficacy in treating PPAR-related diseases by in vitro assays (See Examples 176 and 177 below) and then confirmed by animal experiments and clinic trials. Other methods will also be apparent to those of ordinary skill in the art.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Preparation of Compound 1: 2-methyl-2-{1-[3-(7-propyl-3-trifluoromethyl-benzo[d]isoxazol-6-yloxy)-propyl]- 1H-indol-4-yloxy}-propionic acid A mixture of 4-hydroxyindole (0.100 g, 0.75 mmol, 1.0 eq), powdered potassium hydroxide (0.046 g, 0.83 mmol, 1.1 eq), and DMSO (2 mL) was stirred at room temperature for 1 hour and then ethyl 2-bromo-2-methylpropionate (0.161 g, 0.12 mL, 0.83 mmol, 1.1 eq) was added to the above mixture dropwise. The reaction mixture was stirred at room temperature for another 2 hours before 15 mL of water was added. The mixture was extracted with ethyl acetate (2×30 mL). The organic layer was collected, combined, washed with water (6×25 mL) and brine (2×20 mL), and dried over anhydrous $Na_2SO_4$. The solvent was removed in vacuo. The residue thus obtained was purified by flash chromatograph over silica gel using hexane/ethyl acetate (95/5) as an eluant to afford 2-(1H-indol-4-yloxy)-2-methylpropionic acid ethyl ester (0.144 g, yield: 80%).

2-(1H-Indol-4-yloxy)-2-methylpropionic acid ethyl ester (0.100 g, 0.40 mmol, 1.0 eq), powdered potassium hydroxide (0.034 g, 0.61 mmol, 1.5 eq), and DMSO (3 mL) were mixed and stirred at room temperature for 10 minutes. 1-Bromo-3-chloropropane (0.12 mL, 0.191 g, 1.21 mmol, 3.0 eq) was then added to the above mixture. The reaction mixture was stirred at room temperature for another 1.5 hours before 15 mL of water was added. The mixture was extracted with ethyl acetate (2×30 mL). The organic layer was collected, combined, washed with water (6×25 mL) and brine (2×20 mL), and dried over anhydrous $Na_2SO_4$. The solvent was removed in vacuo to afford 2-[1-(3-chloropropyl)-1H-indol-4-yloxy]-2-methylpropionic acid ethyl ester (0.127 g, yield: 97%) as a dense oily liquid, which was used for the next step without further purification.

A mixture of 2-[1-(3-chloropropyl)-1H-indol-4-yloxy]-2-methylpropionic acid ethyl ester (0.100 g, 0.31 mmol, 1.0 eq), 7-propyl-3-trifluoromethyl-benzo[d]isoxazol-6-ol (0.076 g, 0.31 mmol, 1.0 eq), potassium carbonate (0.064 g, 0.46 mmol, 1.5 eq), potassium iodide (0.010 g, 0.06 mmol, 0.2 eq), and DMF (3 mL) was heated at 110° C. for 1.5 hours. The reaction mixture was cooled to room temperature before 20 mL of water was added. The mixture was then extracted with ethyl acetate (2×20 mL). The organic layer was collected, combined, washed with water (6×20 mL) and brine (2×20 mL), and dried over anhydrous $Na_2SO_4$. The solvent was removed in vacuo to give an oily residue, which was purified by filtering through a short silica column using hexane/ethyl acetate (95/5) as an eluant to afford 2-methyl-2-{1-[3-(7- propyl-3-trifluoromethyl-benzo[d]isoxazol-6-yloxy)-propyl]-1H-indol-4-yloxy}-propionic acid ethyl ester (0.140 g, yield: 85%).

2-Methyl-2-{1-[3-(7-propyl-3-trifluoromethyl-benzo[d]isoxazol-6-yloxy)-propyl]-1H-indol-4-yloxy}-propionic acid ethyl ester (0.100 g, 0.19 mmol, 1 eq) and LiOH (0.018 g, 0.75 mmol, 4 eq) were added to a methanol and water mixture (10 mL, 4:1). After the suspension was refluxed for 2 hours, the solvent was removed in vacuo. 0.5 N HCl was added to the residue and the mixture was extracted with ether (2×20 mL). The organic layer was collected, combined, washed with water (2×20 mL) and brine (2×10 mL), and dried over anhydrous $Na_2SO_4$. The solvent was removed in vacuo to afford 2-methyl-2-{1-[3-(7-propyl-3-trifluoromethyl-benzo[d]isoxazol-6-yloxy)-propyl]-1H-indol-4-yloxy}-propionic acid (compound 1, 0.086 g, yield: 90%).

$^1$H NMR (ppm): $CDCl_3$+MeOH-$d_4$ δ 1.05 (t, J=7.2 Hz, 3H), 1.69 (s, 6H), 1.73-1.84 (m, 2H), 2.36 (p, 2H), 3.01 (t, J=7.5 Hz, 2H), 4.01 (t, J=5.4 Hz, 2H), 4.40 (t, J=6.6 Hz, 2H), 6.56-6.60 (m, 2H), 6.93 (d, J=8.7 Hz, 1H), 6.99 (d, J=3 Hz, 1H), 7.04-7.10 (m, 3H), 7.53 (d, J=8.7 Hz, 1H).

LC/MS $(M+1)^+$: 505.

EXAMPLE 2

Preparation of Compound 2: {4-[3-(7-propyl-3-trifluoromethyl-benzo[d]isoxazol-6-yloxy)-propoxy]-indol-1-yl}-acetic acid A mixture of 4-hydroxyindole (0.100 g, 0.75 mmol, 1.0 eq), powdered potassium hydroxide (0.042 g, 0.75 mmol, 1.0 eq), and DMSO (3 mL) was stirred at room temperature for 1 hour before 1-bromo-3-chloropropane (0.118 g, 0.75 mmol, 1.0 eq) was added. The above mixture was then stirred at room temperature for another 0.5 hour and then 15 mL of water was added to it. The resultant mixture was extracted with ethyl acetate (2×30 mL). The organic layer was collected, combined, washed with water (6×25 mL) and brine (2×20 mL), and dried over anhydrous $Na_2SO_4$. The solvent was removed in vacuo and the residue was purified by flash chromatography over silica gel using hexane/ethyl acetate (95/5) as an eluant to afford 4-(3-chloropropoxy)-1H-indole (0.130 g, yield: 83%).

4-(3-Chloropropoxy)-1H-indole (0.100 g, 0.48 mmol), 7-propyl-3-trifluoromethyl-benzo[d]isoxazol-6-ol (0.117 g, 0.48 mmol), potassium carbonate (0.099 g, 0.72 mmol), potassium iodide (0.016 g, 0.10 mmol), and DMF (5 mL) were mixed and heated at 110° C. for 1.5 hours. The mixture was cooled to room temperature. Water (10 mL) and ethyl acetate (10 mL) were added and the resultant mixture was stirred for five minutes. The organic layer was separated and aqueous layer was extracted again with ethyl acetate (10 mL). The organic layer was combined, washed with water (6×20 mL) and brine (2×20 mL), and dried over anhydrous $Na_2SO_4$. The solvent was removed in vacuo to give an oily residue, which was purified by filtering through a short silica column using hexane/dichloromethane (50/50) as an eluant to afford 6-[3-(1H-indol-4-yloxy)-propoxy]-7-propyl-3-trifluoromethyl-benzo[d]isoxazole (0.156 g, yield: 78%).

A mixture of 6-[3-(1H-indol-4-yloxy)-propoxy]-7-propyl-3-trifluoromethyl-benzo[d]isoxazole (0.100 g, 0.24 mmol), methyl-2-bromoacetate (0.109 g, 0.72 mmol), potassium carbonate (0.050 g, 0.36 mmol), potassium iodide (0.008 g, 0.05 mmol), and acetonitrile (15 mL) was stirred and refluxed for 12 hours. The mixture was cooled to room temperature and filtered to remove suspended salts. The solvent was removed in vacuo and the residue partitioned between dichloromethane and water. The organic layer was collected, washed with water (2×20 mL) and brine (2×20 mL), and then dried over anhydrous $Na_2SO_4$. The solvent was removed and the residue was purified by flash chromatograph over silica gel using hexane/ethyl acetate (95/5) as an eluant to afford {4-[3-(7-propyl-3-trifluoromethyl-benzo[d]isoxazol-6-yloxy)-propoxy]-indol-1-yl}-acetic acid methyl ester (0.089 g, yield: 76%).

{4-[3-(7-Propyl-3-trifluoromethyl-benzo[d]isoxazol-6-yloxy)-propoxy]-indol-1-yl}-acetic acid methyl ester (0.080 g, 0.16 mmol) and LiOH (0.016 g, 0.65 mmol) were added in a methanol and water mixture (10 mL, 4:1). After the mixture was refluxed for 2 hours, the solvent was removed in vacuo. 0.5 N HCl was added to residue and the mixture was extracted with ether (2×20 mL). The organic layer was collected, combined, washed with water (2×20 mL) followed by brine (2×10 mL), and dried over anhydrous $Na_2SO_4$. The solvent was then removed to afford {4-[3-(7-propyl-3-trifluoromethyl-benzo[d]isoxazol-6-yloxy)-propoxy]-indol-1-yl}-acetic acid (compound 2, 0.073 g, yield: 94%).

$^1$H NMR (ppm): $CDCl_3$ δ 0.94 (t, J=7.5 Hz, 3H), 1.65-1.72 (m, 2H), 2.42 (p, 2H), 2.91 (t, J=7.5 Hz, 2H), 4.34-4.38 (m, 4H), 4.82 (s, 2H), 6.56 (d, J=7.2 Hz, 1H), 6.63 (dd, J=0.9, 3 Hz, 1H), 6.90 (d, J=8.4 Hz, 1H), 7.00 (d, J=3 Hz, 1H), 7.09-7.15 (m, 2H), 7.54 (d, J=8.4 Hz, 1H).

LC/MS $(M+1)^+$: 477.

EXAMPLE 3

Preparation of compound 3: 2-(1H-indol-4-yloxy)-2-methyl-propionic acid

Compound 3 was prepared in a manner similar to that described in the first and fourth paragraphs of Example 1.

$^1$H NMR (ppm): $CDCl_3$ δ 1.40 (s, 6H), 6.21 (d, J=7.8 Hz, 1H), 6.28 (t, J=2.1 Hz, 1H), 6.77 (t, J=8.1 Hz, 1H), 6.78 (d, J=8.1 Hz, 1H), 7.83 (t, J=2.1 Hz, 1H), 9.86 (bs, 1H).

LC/MS $(M+1)^+$: 220.

EXAMPLE 4

Preparation of compound 4: 2-methyl-2-{1-[3-(7-propyl-3-trifluoromethyl-benzo[d]isoxazol-6-yloxy)-propyl]-1H-indol-4-yloxy}-propionic acid tert-butyl ester Compound 4 was prepared in a manner similar to that described in Example 1.

$^1$H NMR (ppm): $CDCl_3$ δ 1.04 (t, J=7.5 Hz, 3H), 1.45 (s, 9H), 1.65 (s, 6H) 1.75-1.83 (m, 2H), 2.36 (p, 2H), 3.00 (t, J=7.5 Hz, 2H), 3.99 (t, J=5.4 Hz, 2H), 4.37 (t, J=6.6 Hz, 2H), 6.44 (dd, J=1.5, 4.2 Hz, 1H), 6.58 (d, J=3 Hz, 1H), 6.91-6.99 (m, 4H), 7.52 (d, J=8.7 Hz, 1H).

LC/MS $(M+1)^+$: 561.

EXAMPLE 5

Preparation of Compound 5: 2-methyl-2-{1-[3-(7-propyl-3-trifluoromethyl-benzo[d]isoxazol-6-yloxy)-propyl]-1H-indol-5-yloxy}-propionic acid tert-butyl ester Compound 5 was prepared in a manner similar to that described in Example 1.

$^1$H NMR (ppm): $CDCl_3$ δ 1.02 (t, J=7.5 Hz, 3H), 1.47 (s, 9H), 1.51 (s, 6H) 1.71-1.81 (m, 2H), 2.34 (p, 2H), 2.98 (t, J=7.5 Hz, 2H), 3.99 (t, J=5.4 Hz, 2H), 4.35 (t, J=6.6 Hz, 2H), 6.36 (d, J=3 Hz, 1H), 6.84 (dd, J=2.4, 8.7 Hz, 1H), 6.91 (d, J=9 Hz, 1H), 7.01 (d, J=3 Hz, 1H), 7.13 (d, J=2.1 Hz, 1H), 7.17 (d, J=9 Hz, 1H), 7.50 (d, J=8.7 Hz, 1H).

LC/MS (M+1)$^+$: 561.

EXAMPLE 6

Preparation of compound 6: 2-methyl-2-{1-[3-(7-propyl-3-trifluoromethyl-benzo[d]isoxazol-6-yloxy)-propyl]-1H-indol-6-yloxy}-propionic acid tert-butyl ester Compound 6 was prepared in a manner similar to that described in Example 1.

$^1$H NMR (ppm): CDCl$_3$ δ 1.04 (t, J=7.5 Hz, 3H), 1.49 (s, 9H), 1.56 (s, 6H), 1.73-1.83 (m, 2H), 2.35 (p, 2H), 3.01 (t, J=7.5 Hz, 2H), 4.01 (t, J=5.4 Hz, 2H), 4.33 (t, J=6.3 Hz, 2H), 6.41 (d, J=3.3 Hz, 1H), 6.76 (dd, J=2.1, 5.4 Hz, 1H), 6.95 (d, J=9.3 Hz, 2H), 6.96 (d, J=3.3 Hz, 1H), 7.46 (d, J=8.7 Hz, 1H), 7.53 (d, J=8.7 Hz, 1H).

LC/MS (M+1)$^+$: 561.

EXAMPLE 7

Preparation of Compound 7: 2-methyl-2-{1-[3-(7-propyl-3-trifluoromethyl-benzo[d]isoxazol-6-yloxy)-propyl]-1H-indol-5-yloxy}-propionic acid Compound 7 was prepared in a manner similar to that described in Example 1.

$^1$H NMR (ppm): CDCl$_3$+MeOH-d$_4$ δ 1.04 (t, J=7.5 Hz, 3H), 1.56 (s, 6H) 1.75-1.85 (m, 2H), 2.38 (p, 2H), 3.00 (t, J=7.5 Hz, 2H), 4.02 (t, J=5.4 Hz, 2H), 4.40 (t, J=6.6 Hz, 2H), 6.44 (d, J=3 Hz, 1H), 6.86 (dd, J=2.4, 9 Hz, 1H), 6.93 (d, J=8.7 Hz, 1H), 7.08 (d, J=3 Hz, 1H), 7.19 (d, J=9 Hz, 1H), 7.23 (d, J=2.1 Hz, 2H), 7.53 (d, J=8.7 Hz, 1H).

LC/MS (M+1)$^+$: 505.

EXAMPLE 8

Preparation of compound 8: 2-methyl-2-{1-[3-(7-propyl-3-trifluoromethyl-benzo[d]isoxazol-6-yloxy)-propyl]-1H-indol-6-yloxy}-propionic acid Compound 8 was prepared in a manner similar to that described in Example 1.

$^1$H NMR (ppm): CDCl$_3$+MeOH-d$_4$ δ 1.03 (t, J=7.5 Hz, 3H), 1.55 (s, 6H), 1.74-1.82 (m, 2H), 2.33 (p, 2H), 2.99 (t, J=7.5 Hz, 2H), 3.99 (t, J=5.4 Hz, 2H), 4.33 (t, J=6.6 Hz, 2H), 6.44 (d, J=3.0 Hz, 1H), 6.79 (dd, J=1.8, 8.7 Hz, 1H), 6.91 (d, J=8.7 Hz, 2H), 6.96 (d, J=1.8 Hz, 1H), 7.02 (d, J=3.0 Hz, 1H), 7.48-7.53 (m, 2H).

LC/MS (M+1)$^+$: 505.

EXAMPLE 9

Preparation of Compound 9: 1-[3-(7-propyl-3-trifluoromethyl-benzo[d]isoxazol-6-yloxy)-propyl]-1H-indole-4-carboxylic acid methyl ester Compound 9 was prepared in a manner similar to that described in Example 1.

$^1$H NMR (ppm): CDCl$_3$ δ 1.04 (t, J=7.5 Hz, 3H), 1.75-1.83 (m, 2H), 2.37 (p, 2H), 3.00 (t, J=7.5 Hz, 2H), 3.97 (s, 3H), 3.98 (t, J=5.4 Hz, 2H), 4.46 (t, J=6.6 Hz, 2H), 6.91 (d, J=8.7 Hz, 1H), 7.12 (d, J=3 Hz, 1H), 7.19-7.24 (m, 2H), 7.50-7.56 (m, 2H), 7.89 (dd, J=0.9, 7.5 Hz, 1H).

LC/MS (M+1)$^+$: 461.

EXAMPLE 10

Preparation of Compound 10: 1-[3-(7-propyl-3-trifluoromethyl-benzo[d]isoxazol-6-yloxy)-propyl]-1H-indole-4-carboxylic acid Compound 10 was prepared in a manner similar to that described in Example 1.

$^1$H NMR (ppm): CDCl$_3$+MeOH-d$_4$ δ 1.04 (t, J=7.5 Hz, 3H), 1.75-1.83 (m, 2H), 2.38 (p, 2H), 3.00 (t, J=7.5 Hz, 2H), 4.01 (t, J=5.4 Hz, 2H), 4.47 (t, J=6.6 Hz, 2H), 6.94 (d, J=8.7 Hz, 1H), 7.13 (d, J=3 Hz, 1H), 7.21-7.25 (m, 2H), 7.51-7.59 (m, 2H), 7.90 (d, J=7.5 Hz, 1H).

LC/MS (M+1)$^+$: 447.

EXAMPLE 11

Preparation of Compound 11: {1-[3-(7-propyl-3-trifluoromethyl-benzo[d]isoxazol-6-yloxy)-propyl]-1H-indol-3-yl}-acetic acid Compound 11 was prepared in a manner similar to that described in Example 1.

$^1$H NMR (ppm): CDCl$_3$+MeOH-d$_4$ δ 1.02 (t, J=7.5 Hz, 3H), 1.73-1.81 (m, 2H), 2.35 (p, 2H), 2.98 (t, J=7.5 Hz, 2H), 3.76 (s, 2H), 4.00 (t, J=5.4 Hz, 2H), 4.37 (t, J=6.6 Hz, 2H), 6.91 (d, J=9 Hz, 1H), 7.04 (s, 1H), 7.11 (t, J=7.5 Hz, 1H), 7.19 (t, J=7.5 Hz, 1H), 7.31 (d, J=8.1 Hz, 1H), 7.50 (d, J=8.7 Hz, 1H), 7.59 (d, J=7.5 Hz, 1H).

LC/MS (M+1)+: 461.

EXAMPLE 12

Preparation of compound 12: 1-[3-(7-propyl-3-trifluoromethyl-benzo[d]isoxazol-6-yloxy)-propyl]-1H-indole-6-carboxylic acid Compound 12 was prepared in a manner similar to that described in Example 1.

$^1$H NMR (ppm): CDCl$_3$+MeOH-d$_4$ δ 1.04 (t, J=7.5 Hz, 3H), 1.75-1.85 (m, 2H), 2.43 (p, 2H), 3.03 (t, J=7.5 Hz, 2H), 4.03 (t, J=5.4 Hz, 2H), 4.52 (t, J=6.6 Hz, 2H), 6.55 (d, J=3 Hz, 1H), 6.92 (d, J=8.7 Hz, 1H), 7.25 (d, J=3 Hz, 1H), 7.51 (d, J=8.7 Hz, 1H), 7.66 (d, J=8.7 Hz, 1H), 7.85 (dd, J=0.9, 8.7 Hz, 1H), 8.19 (s, 1H).

LC/MS (M+1)$^+$: 447.

EXAMPLE 13

Preparation of compound 13: 1-[3-(7-propyl-3-trifluoromethyl-benzo[d]isoxazol-6-yloxy)-propyl]-1H-indole-3-carboxylic acid Compound 13 was prepared in a manner similar to that described in Example 1.

$^1$H NMR (ppm): CDCl$_3$+MeOH-d$_4$ δ 1.03 (t, J=7.5 Hz, 3H), 1.72-1.84 (m, 2H), 2.43 (p, 2H), 2.99 (t, J=7.5 Hz, 2H), 4.07 (t, J=5.4 Hz, 2H), 4.46 (t, J=6.9 Hz, 2H), 6.94 (d, J=9 Hz, 1H), 7.25-7.33 (m, 2H), 7.39-7.41 (m, 1H), 7.52 (d, J=8.7 Hz, 1H), 7.90 (s, 1H), 8.22-8.25 (m, 1H).

LC/MS (M+1)$^+$: 447.

EXAMPLE 14

Preparation of Compound 14: 1-[3-(7-propyl-3-trifluoromethyl-benzo[d]isoxazol-6-yloxy)-propyl]-1H-indole-2-carboxylic acid Compound 14 was prepared in a manner similar to that described in Example 1.

$^1$H NMR (ppm): CDCl$_3$+MeOH-d$_4$ δ 1.03 (t, J=7.5 Hz, 3H), 1.72-1.81 (m, 2H), 2.38 (p, 2H), 2.99 (t, J=7.5 Hz, 2H), 4.10 (t, J=5.7 Hz, 2H), 4.82 (t, J=6.9 Hz, 2H), 6.94 (d, J=8.7 Hz, 1H), 7.13 (t, J=7.5 Hz, 1H), 7.28 (t, J=7.5, 1H), 7.37 (s, 1H), 7.40 (d, J=8.1 Hz, 1H) 7.51 (d, J=8.7 Hz, 1H), 7.68 (d, J=8.1 Hz, 1H).

LC/MS (M+1)$^+$: 447.

EXAMPLE 15

Preparation of Compound 15: 6-[2-(1-benzenesulfonyl-1H-indol-3-yl)-ethoxy]-7-propyl-3-trifluoromethyl-benzo[d]isoxazole Compound 15 was prepared in a manner similar to that described in Example 2.

$^1$H NMR (ppm): CDCl$_3$ δ 0.88 (t, J=7.5 Hz, 3H), 1.53-1.65 (m, 2H), 2.80 (t, J=7.5 Hz, 2H), 3.22 (t, J=6.3 Hz, 2H), 4.35 (t, J=6.6 Hz, 2H), 7.01 (d, J=8.7 Hz, 1H), 7.22-7.41 (m, 4H), 7.48-7.58 (m, 4H), 7.84-7.87 (m, 2H), 8.00 (d, J=8.1 Hz, 1H).

LC/MS (M+1)$^+$: 529.

EXAMPLE 16

Preparation of Compound 16: 6-[2-(1H-indol-3-yl)-ethoxy]-7-propyl-3-trifluoromethyl-benzo[d]isoxazole Compound 16 was prepared in a manner similar to that described in Example 2.

$^1$H NMR (ppm): CDCl$_3$ δ 0.92 (t, J=7.5 Hz, 3H), 1.59-1.72 (m, 2H), 2.89 (t, J=7.5 Hz, 2H), 3.20 (t, J=6.3 Hz, 2H), 4.35 (t, J=6.6 Hz, 2H), 7.02 (d, J=8.7 Hz, 1H), 7.11-7.21 (m, 3H), 7.38 (d, J=7.5 Hz, 1H), 7.50 (d, J=8.7 Hz, 1H), 7.65 (d, J=8.1 Hz, 1H), 8.05 (bs, 1H).

LC/MS (M+1)$^+$: 389.

EXAMPLE 17

Preparation of Compound 17: 6-[3-(1H-indol-4-yloxy)-propoxy]-7-propyl-3-trifluoromethyl-benzo[d]isoxazole Compound 17 was prepared in a manner similar to that described in Example 2.

$^1$H NMR (ppm): CDCl$_3$ δ 0.98 (t, J=7.5 Hz, 3H), 1.66-1.78 (m, 2H), 2.45 (p, 2H), 2.94 (t, J=7.5 Hz, 2H), 4.36-4.41 (m, 4H), 6.58 (d, J=7.2 Hz, 1H), 6.66-6.68 (m, 1H), 7.04 (d, J=8.4 Hz, 1H), 7.09-7.16 (m, 3H), 7.55 (d, J=8.7 Hz, 1H), 8.20 (bs, 1H).

LC/MS (M+1)$^+$: 419.

EXAMPLE 18

Preparation of Compound 18: {1-[3-(7-propyl-3-trifluoromethyl-benzo[d]isoxazol-6-yloxy)-propyl]-1H-indol-4-yloxy}-acetic acid Compound 18 was prepared in a manner similar to that described in Example 1.

$^1$H NMR (ppm): CDCl$_3$+MeOH-d$_4$ δ 0.90 (t, J=7.5 Hz, 3H), 1.55-1.69 (m, 2H), 2.21 (p, 2H), 2.86 (t, J=7.5 Hz, 2H), 3.87 (t, J=5.7 Hz, 2H), 4.26 (t, J=6.6 Hz, 2H), 4.61 (s, 2H), 6.31 (d, J=6.6 Hz, 1H), 6.53 (d, J=3 Hz, 1H), 6.81-6.96 (m, 4H), 7.39 (d, J=9.0 Hz, 1H).

LC/MS (M+1)$^+$: 477.

EXAMPLE 19

Preparation of Compound 19: {3-[2-(7-propyl-3-trifluoromethyl-benzo[d]isoxazol-6-yloxy)-ethyl]-indol-1-yl}-acetic acid Compound 19 was prepared in a manner similar to that described in Example 2.

$^1$H NMR (ppm): CDCl$_3$+MeOH-d$_4$ δ 0.95 (t, J=7.5 Hz, 3H), 1.61-1.73 (m, 2H), 2.90 (t, J=7.5 Hz, 2H), 3.31 (t, J=6.9 Hz, 2H), 4.36 (t, J=6.9 Hz, 2H), 4.81 (s, 2H), 7.02 (s, 1H), 7.05 (d, J=9.0 Hz, 1H), 7.14 (t, J=6.9 Hz, 1H), 7.21-7.29 (m, 2H), 7.52 (d, J=8.4 Hz, 1H), 7.63 (d, J=7.8 Hz, 1H).

LC/MS (M+1)$^+$: 447.

EXAMPLE 20

Preparation of Compound 20: {1-[3-(7-propyl-3-trifluoromethyl-benzo[d]isoxazol-6-yloxy)-propyl]-1H-indol-6-yloxy}-acetic acid Compound 20 was prepared in a manner similar to that described in Example 1.

$^1$H NMR (ppm): CDCl$_3$ δ 1.00 (t, J=7.2 Hz, 3H), 1.70-1.80 (m, 2H), 2.96 (t, J=7.5 Hz, 2H), 3.92 (t, J=5.4 Hz, 2H), 4.27 (t, J=6.0 Hz, 2H), 4.48 (s, 2H), 6.38 (d, J=3.0 Hz, 1H), 6.72-6.80 (m, 2H), 6.84 (d, J=8.7 Hz, 1H), 6.93 (d, J=3.3 Hz, 1H), 7.35 (d, J=8.7 Hz, 1H), 7.45 (d, J=8.7 Hz, 1H).

LC/MS (M+1)$^+$: 477.

EXAMPLE 21

Preparation of Compound 21: {5-methoxy-2-methyl-1-[3-(7-propyl-3-trifluoromethyl-benzo[d]isoxazol-6-yloxy)-propyl]-1H-indol-3-yl}-acetic acid Compound 21 was prepared in a manner similar to that described in Example 1.

$^1$H NMR (ppm): CDCl$_3$ δ 1.02 (t, J=7.2 Hz, 3H), 1.72-1.81 (m, 2H), 2.27 (t, J=6.0 Hz, 2H), 2.36 (s, 3H), 2.99 (t, J=7.5 Hz, 2H), 3.65 (s, 3H), 3.84 (s, 3H), 4.04 (t, J=5.4 Hz, 2H), 4.31 (t, J=6.9 Hz, 2H), 6.76 (dd, J=9.0, 2.4 Hz, 1H), 6.94 (d, J=8.7 Hz, 1H), 7.00 (d, J=2.1 Hz, 1H), 7.14 (d, J=9.0 Hz, 1H ), 7.52 (d, J=8.7 Hz, 1H).

LC/MS (M+1)$^+$: 505.

EXAMPLE 22

Preparation of Compound 22: 2-[1-(4-chloro-benzyl)-1H-indol-4-yloxy]-2-methyl-propionic acid Compound 22 was prepared in a manner similar to that described in Example 1.

$^1$H NMR (ppm): CDCl$_3$ d 1.68 (s, 6H), 5.22 (s, 2H), 6.55 (d, J=7.5 Hz, 2H), 6.61 (d, J=3.3 Hz, 1H), 6.90-7.04 (m, 5H), 7.22 (d, J=8.1 Hz, 1H).

LC/MS (M+1)$^+$: 344.

EXAMPLE 23

Preparation of Compound 23: 2-{1-[3-(7-propyl-3-trifluoromethyl-benzo[d]isoxazol-6-yloxy)-propyl]-1H-indol-4-yloxy}-ethylamine Compound 23 was prepared in a manner similar to that described in Example 1.

$^1$H NMR (ppm): CDCl$_3$+MeOH-d$_4$ δ 1.03 (t, J=7.5 Hz, 3H), 1.72-1.84 (m, 2H), 1.90 (s, 2H), 2.21 (p, 2H), 2.99 (t, J=7.5 Hz, 2H), 3.14 (t, J=4.8 Hz, 2H), 3.97 (t, J=5.4 Hz, 2H), 4.13 (t, J=4.8 Hz, 2H), 4.37 (t, J=6.6 Hz, 2H), 6.51 (d, J=7.8 Hz, 1H), 6.60 (d, J=3 Hz, 1H), 6.88-6.98 (m, 3H), 7.08 (t, J=7.8 Hz, 1H), 7.50 (d, J=9.0 Hz, 1H). LC/MS (M+1)$^+$: 462.

EXAMPLE 24

Preparation of Compound 24: 6-{3-[4-(3,5-dimethyl-isoxazol-4-ylmethoxy)-indol-1-yl]-propoxy}-7-propyl-3-trifluoromethyl-benzo[d]isoxazole Compound 24 was prepared in a manner similar to that described in Example 1.

$^1$H NMR (ppm): CDCl$_3$ δ 1.03 (t, J=7.5 Hz, 3H), 1.75-1.82 (m, 2H), 2.32 (s, 3H), 2.36 (m, 2H), 2.38 (s, 3H), 2.99 (t, J=7.2 Hz, 2H), 4.00 (t, J=5.4 Hz, 2H), 4.39 (t, J=6.6 Hz, 2H), 4.94 (s, 2H), 6.53 (d, J=3.0 Hz, 1H), 6.58 (d, J=7.5 Hz, 1H), 6.92 (d, J=9.0 Hz, 1H), 6.96 (d, J=3.0 Hz, 1H), 7.01 (d, J=8.1 Hz, 1H), 7.11 (t, J=7.5, 8.1 Hz, 1H), 7.51 (d, J=9.0 Hz, 1H).

LC/MS (M+1)$^+$: 528.

EXAMPLE 25

Preparation of Compound 25: N-(2-{1-[3-(7-propyl-3-trifluoromethyl-benzo[d]isoxazol-6-yloxy)-propyl]-1H-indol-4-yloxy}-ethyl)-methanesulfonamide Compound 25 was prepared in a manner similar to that described in Example 1.

$^1$H NMR (ppm): CDCl$_3$ δ 1.04 (t, J=7.2 Hz, 3H), 1.75-1.83 (m, 2H), 2.36 (p, 2H), 3.00 (t, J=7.5 Hz, 2H), 3.04 (s, 3H), 3.64 (q, J=5.1, 5.4, 5.1 Hz, 2H), 3.99 (t, J=5.4 Hz, 2H), 4.26 (t, J=5.1 Hz, 2H), 4.40 (t, J=6.3 Hz, 2H), 6.50 (d, J=7.5 Hz, 1H), 6.53 (d, J=2.7 Hz, 1H), 6.92 (d, J=8.1 Hz, 1H), 6.98-7.02 (m, 2H), 7.09 (t, J=7.5 Hz, 1H), 7.52 (d, J=8.4 Hz, 1H).

LC/MS (M+1)$^+$: 540.

EXAMPLE 26

Preparation of Compound 26: 6-[3-(1H-indol-5-yloxy)-propoxy]-7-propyl-3-trifluoromethyl-benzo[d]isoxazole Compound 26 was prepared in a manner similar to that described in Example 2.

$^1$H NMR (ppm): CDCl$_3$ δ 0.94 (t, J=7.5 Hz, 3H), 1.62-1.72 (m, 2H), 2.34 (p, 2H), 2.90 (t, J=7.5 Hz, 2H), 4.23 (d, J=6.0 Hz, 2H), 4.30 (t, J=6.0 Hz, 2H), 6.44-6.45 (m, 1H), 6.85 (dd, J=1.2, 8.7 Hz, 1H), 7.05-7.15 (m, 3H), 7.25 (d, J=8.7 Hz, 1H), 7.52 (d, J=8.7 Hz, 1H), 8.07 (bs, 1H).

LC/MS (M+1)$^+$: 419.

EXAMPLE 27

Preparation of Compound 27: 6-[3-(1H-indol-6-yloxy)-propoxy]-7-propyl-3-trifluoromethyl-benzo[d]isoxazole Compound 27 was prepared in a manner similar to that described in Example 2.

$^1$H NMR (ppm): CDCl$_3$ δ 0.93 (t, J=7.5 Hz, 3H), 1.63-1.71 (m, 2H), 2.34 (p, 2H), 2.90 (t, J=7.5 Hz, 2H), 4.21 (d, J=6.0 Hz, 2H), 4.30 (t, J=6.0 Hz, 2H), 6.45-6.47 (m, 1H), 6.79 (dd, J=2.1, 8.7 Hz, 1H), 6.87 (s, 1H), 7.04-7.07 (m, 2H), 7.47-7.53 (m, 2H), 8.04 (bs, 1H).

LC/MS (M+1)$^+$: 419.

EXAMPLE 28

Preparation of Compound 28: {5-[3-(7-propyl-3-trifluoromethyl-benzo[d]isoxazol-6-yloxy)-propoxy]-indol-1-yl}-acetic acid Compound 28 was prepared in a manner similar to that described in Example 2.

$^1$H NMR (ppm): CDCl$_3$ δ 0.95 (t, J=7.5 Hz, 3H), 1.65-1.73 (m, 2H), 2.34 (p, 2H), 2.91 (t, J=7.5 Hz, 2H), 4.23 (d, J=6.0 Hz, 2H), 4.32 (t, J=6.0 Hz, 2H), 4.79 (s, 2H), 6.45 (d, J=3 Hz, 1H), 6.87 (dd, J=1.5, 8.7 Hz, 1H), 7.06-7.16 (m, 4H), 7.54 (d, J=8.7 Hz, 1H).

LC/MS (M+1)$^+$: 477.

EXAMPLE 29

Preparation of Compound 29: {6-[3-(7-propyl-3-trifluoromethyl-benzo[d]isoxazol-6-yloxy)-propoxy]-indol-1-yl}-acetic acid Compound 29 was prepared in a manner similar to that described in Example 2.

$^1$H NMR (ppm): CDCl$_3$ δ 0.92 (t, J=7.5 Hz, 3H), 1.63-1.71 (m, 2H), 2.34 (p, 2H), 2.89 (t, J=7.5 Hz, 2H), 4.22 (d, J=6.0 Hz, 2H), 4.30 (t, J=6.0 Hz, 2H), 4.79 (s, 2H), 6.48 (d, J=3.0 Hz, 1H), 6.70 (d, J=1.8 Hz, 1H), 6.80 (dd, J=2.1, 8.7 Hz, 1H), 6.94 (d, J=3.0 Hz, 1H), 7.07 (d, J=8.7 Hz, 1H), 7.47-7.54 (m, 2H).

LC/MS (M+1)$^+$: 477.

EXAMPLE 30

Preparation of Compound 30: {1-[3-(7-propyl-3-trifluoromethyl-benzo[d]isoxazol-6-yloxy)-propyl]-1H-indol-5-yloxy}-acetic acid Compound 30 was prepared in a manner similar to that described in Example 1.

$^1$H NMR (ppm): CDCl$_3$ δ 0.99 (t, J=7.2 Hz, 3H), 1.70-1.80 (m, 2H) 2.62 (bs, 2H), 2.91-2.98 (t, 2H), 3.90 (bs, 2H), 4.29 (bs, 2H), 4.55 (bs, 2H), 6.34 (bs, 1H), 6.80-6.90 (m, 2H), 6.95-7.08 (m, 2H), 7.18-7.22 (bd, 1H), 7.46 (d, J=8.4 Hz, 1H).

LC/MS (M+1)$^+$: 477.

EXAMPLE 31

Preparation of Compound 31: 6-{2-[1-(3,5-bis-trifluoromethyl-benzenesulfonyl)-1H-indol-3-yl]-ethoxy}-7-propyl-3-trifluoromethyl-benzo[d]isoxazole Compound 31 was prepared in a manner similar to that described in Example 2.

$^1$H NMR (ppm): CDCl$_3$ δ 0.87 (t, J=7.2 Hz, 3H), 1.57-1.62 (m, 2H), 2.78-2.84 (m, 2H), 3.24 (t, J=6.3 Hz, 2H), 4.34 (t, J=6.6 Hz, 2H), 7.00 (d, J=8.7 Hz, 1H), 7.29-7.59 (m, 5H), 7.97-8.00 (m, 2H), 8.26 (s, 2H).

LC/MS (M+1)$^+$: 665.

EXAMPLE 32

Preparation of Compound 32: 6-{3-[1-(3,5-bis-trifluoromethyl-benzenesulfonyl)-1H-indol-4-yloxy]-propoxy}-7-propyl-3-trifluoromethyl-benzo[d]isoxazole Compound 32 was prepared in a manner similar to that described in Example 2.

$^1$H NMR (ppm): CDCl$_3$ δ 0.88 (t, J=7.5 Hz, 3H), 1.60-1.70 (m, 2H), 2.38 (t, J=6.0 Hz, 2H), 2.84-2.90 (m, 2H), 4.27-4.32 (m, 4H), 6.72 (d, J=8.1 Hz, 1H), 6.83 (d, J=3.6 Hz, 1H), 7.05 (d, J=8.7 Hz, 1H), 7.25-7.31 (m, 1H), 7.43 (d, J=3.6 Hz, 1H), 7.50-7.60 (m, 2H), 7.99 (s, 1H), 8.27 (s, 2H).

LC/MS (M+1)$^+$: 695.

EXAMPLE 33

Preparation of Compound 33: 7-propyl-6-{3-[4-(2H-tetrazol-5-ylmethoxy)-indol-1-yl]-propoxy}-3-trifluoromethyl-benzo[d]isoxazole Compound 33 was prepared in a manner similar to that described in Example 1.

$^1$H NMR (ppm): MeOH-d$_4$ δ 0.95 (t, J=7.2 Hz, 3H), 1.65-1.74 (m, 2H), 2.28 (t, J=6.0 Hz, 2H), 2.87-2.93 (m, 2H), 3.99 (t, J=5.4 Hz, 2H), 4.36 (t, J=6.6 Hz, 2H), 5.48 (s, 2H), 6.52-6.57 (m, 2H), 6.93-7.06 (m, 4H), 7.52 (d, J=9.0 Hz, 1H).

LC/MS (M+1)$^+$: 501.

EXAMPLE 34

Preparation of Compound 34: 7-propyl-6-{3-[3-(2H-tetrazol-5-ylmethyl)-indol-1-yl]-propoxy}-3-trifluoromethyl-benzo[d]isoxazole Compound 34 was prepared in a manner similar to that described in Example 1.

$^1$H NMR (ppm): CDCl$_3$+MeOH-d$_4$ δ 1.00 (t, J=7.2 Hz, 3H), 1.72-1.80 (m, 2H), 2.35 (t, J=6.0 Hz, 2H), 2.93-2.99 (m, 2H), 4.08 (t, J=5.4 Hz, 2H), 4.38-4.44 (m, 4H). 6.99-7.14 (m, 4H), 7.36-7.43 (m, 2H), 7.56 (d, J=8.7 Hz, 1H).

LC/MS (M+1)$^+$: 485.

EXAMPLE 35

Preparation of Compound 35: 7-propyl-6-{3-[1-(2H-tetrazol-5-ylmethyl)-1H-indol-4-yloxy]-propoxy}-3-trifluoromethyl-benzo[d]isoxazole Compound 35 was prepared in a manner similar to that described in Example 2.

$^1$H NMR (ppm): CDCl$_3$+MeOH-d$_4$ δ 0.89 (t, J=7.2 Hz, 3H), 1.60-1.69 (m, 2H), 2.39 (t, J=6.0 Hz, 2H), 2.89 (t, J=7.5 Hz, 2H), 4.35 (t, J=6.0 Hz, 2H), 4.40 (t, J=6.0 Hz, 2H), 5.64 (s, 2H), 6.55-6.59 (m, 2H), 6.97-7.09 (m, 2H), 7.17 (d, J=3.3 Hz, 1H), 7.28 (d, J=9.0 Hz, 1H), 7.59 (d, J=8.1 Hz, 1H).

LC/MS (M+1)$^+$: 501.

EXAMPLE 36

Preparation of Compound 36: {1-[2-(methyl-pyridin-2-yl-amino)-ethyl]-1H-indol-4-yloxy}-acetic acid Compound 36 was prepared in a manner similar to that described in Example 1.

LC/MS (M+1)$^+$: 326.

EXAMPLE 37

Preparation of Compound 37: 2-{1-[3-(2,3-dimethyl-indol-1-yl)-propyl]-1H-indol-4-yloxy}-propan-2-ol Compound 37 was prepared in a manner similar to that described in Example 1.

$^1$H NMR (ppm): CDCl$_3$+MeOH-d$_4$ δ 1.65 (s, 6H), 2.16 (s, 3H), 2.21 (s, 3H), 2.25 (p, J=7 Hz, 2H), 4.01 (t, J=7 Hz, 2H), 4.10 (t, J=7 Hz, 2H), 6.56-6.61 (m, 2H), 6.93 (d, J=8.1 Hz, 1H), 7.00-7.07 (m, 5H), 7.44-7.47 (m, 1H).

LC/MS (M+1)$^+$: 405.

EXAMPLE 38

Preparation of Compound 38: 2-methyl-2-[1-[3-(7-propyl-3-trifluoromethyl-benzo[d]isoxazol-6-yloxy)-propyl]-3-(2,2,2-trifluoro-acetyl)-1H-indol-4-yloxy]-propionic acid Compound 38 was prepared in a manner similar to that described in Example 1.

LC/MS (M+1)$^+$: 601.

EXAMPLE 39

Preparation of Compound 39: 2-methyl-2-[1-[3-(7-propyl-3-trifluoromethyl-benzo[d]isoxazol-6-yloxy)-propyl]-3-(2,2,2-trifluoro-acetyl)-1H-indol-5-yloxy]-propionic acid Compound 39 was prepared in a manner similar to that described in Example 1.

$^1$H NMR (ppm): CDCl$_3$+MeOH-d$_4$ δ 1.03 (t, J=7.5 Hz, 3H), 1.62 (s, 6H) 1.75-1.82 (m, 2H), 2.47 (p, 2H), 2.99 (t, J=7.5 Hz, 2H), 4.09 (t, J=5.4 Hz, 2H), 4.50 (t, J=6.6 Hz, 2H), 6.96 (d, J=8.7 Hz, 1H), 7.05 (dd, J=2.1, 9 Hz, 1H), 7.35 (d, J=8.7 Hz, 1H), 7.56 (d, J=8.7 Hz, 1H), 7.89 (d, J=1.2 Hz, 1H), 8.01 (d, J=2.4 Hz, 1H).

LC/MS (M+1)$^+$: 601.

EXAMPLE 40

Preparation of Compound 40: 2-methyl-2-[1-[3-(7-propyl-3-trifluoromethyl-benzo[d]isoxazol-6-yloxy)-propyl]-3-(2,2,2-trifluoro-acetyl)-1H-indol-6-yloxy]-propionic acid Compound 40 was prepared in a manner similar to that described in Example 1.

$^1$H NMR (ppm): CDCl$_3$+MeOH-d$_4$ δ 1.00 (t, J=7.5 Hz, 3H), 1.57 (s, 6H), 1.73-1.80 (m, 2H), 2.42 (p, 2H), 2.97 (t, J=7.5 Hz, 2H), 4.06 (t, J=5.4 Hz, 2H), 4.43 (t, J=6.6 Hz, 2H), 6.93-7.03 (m, 3H), 7.53 (d, J=8.7 Hz, 1H), 7.85 (d, J=1.8 Hz, 1H), 8.25 (d, J=8.4 Hz, 1H).

LC/MS (M+1)$^+$: 601.

EXAMPLE 41

Preparation of Compound 41: {4-[3-(5,7-dichloro-2-methyl-quinolin-8-yloxy)-propoxy]-indol-1-yl}-acetic acid Compound 41 was prepared in a manner similar to that described in Example 2.

$^1$H NMR (ppm): CDCl$_3$+MeOH-d$_4$ δ 2.39 (t, J=6 Hz, 2H), 2.65 (s, 3H), 4.40 (t, J=6 Hz, 2H), 4.53 (t, J=6 Hz, 2H), 4.57 (s, 2H), 6.49-6.52 (m, 2H), 6.71 (d, J=8 Hz, 1H), 6.76 (d, J=2.4 Hz, 1H), 7.01 (t, J=8, 1H), 7.27 (d, J=8.7 Hz, 1H), 7.46 (s, 1H), 8.27 (d, J=8.7 Hz, 1H).

LC/MS (M+1)$^+$: 460.

EXAMPLE 42

Preparation of Compound 42: (4-{3-[4-(4-fluoro-benzoyl)-phenoxy]-propoxy}-indol-1-yl)-acetic acid Compound 42 was prepared in a manner similar to that described in Example 2.

$^1$H NMR (ppm): CDCl$_3$+MeOH-d$_4$ δ 2.37 (t, J=6 Hz, 2H), 4.27-4.33 (m, 4H), 4.83 (s, 2H), 6.55 (d, J=7.8 Hz, 1H), 6.64 (d, J=2.7 Hz, 1H), 6.84 (d, J=8.1 Hz, 1H), 6.93-7.15 (m, 6H), 7.72-7.78 (m, 4H).

HRMS-FAB (M$^+$): 447.15.

EXAMPLE 43

Preparation of Compound 43: 2-methyl-2-{1-[3-(pyridin-4-ylsulfanyl)-propyl]-1H-indol-4-yloxy}-propionic acid Compound 43 was prepared in a manner similar to that described in Example 1.

$^1$H NMR (ppm): CDCl$_3$ d 1.71 (s, 6H), 2.14-2.18 (t, J=6.6 Hz, 2H), 2.74-2.79 (t, J=7.2 Hz, 2H), 4.19-4.23 (t, J=6.0 Hz, 2H), 6.53-6.56 (d, J=7.5 Hz, 1H), 6.63-6.64 (d, J=3.3 Hz, 1H), 6.74-6.76 (d, J=5.1 Hz, 2H), 6.85-6.88 (d, J=8.1 Hz, 1H), 6.94-6.97 (m, 2H), 8.17 (bs, 4H).

LC/MS (M+1)$^+$: 371.

EXAMPLE 44

Preparation of Compound 44: 2-methyl-2-{1-[3-(4-pyrrol-1-yl-phenoxy)-propyl]-1H-indol-4-yloxy}-propionic acid Compound 44 was prepared in a manner similar to that described in Example 1.

$^1$H NMR (ppm): CDCl$_3$ δ 1.66 (s, 6H), 2.24-2.28 (t, J=6.0 Hz, 2H), 3.82-3.85 (t, J=5.7 Hz, 2H), 4.30-4.34 (t, J=6.6 Hz, 2H), 6.30-6.31 (t, J=2.1 Hz, 2H), 6.53-6.54 (d, J=3.0 Hz, 2H), 6.86-6.89 (dd, J1=2.1 Hz, J2=4.8 Hz, 2H), 6.97-6.98 (t, J=2.1 Hz, 2H), 7.01-7.03 (d, J=6.6 Hz, 2H), 7.24-7.27 (dd, J1=2.1 Hz, J2=4.2 Hz, 2H),

LC/MS (M+1)$^+$: 419.

EXAMPLE 45

Preparation of Compound 45: 2-{1-[3-(2-benzoyl-phenoxy)-propyl]-1H-indol-4-yloxy}-2-methyl-propionic acid Compound 45 was prepared in a manner similar to that described in Example 1.

$^1$H NMR (ppm): CDCl$_3$ δ 1.63 (s, 6H), 1.94-1.98 (t, J=6.3 Hz, 2H), 3.78-3.86 (m, 4H), 6.41-6.42 (d, J=3.3 Hz, 1H), 6.55-6.58 (d, J=7.5 Hz, 1H), 6.78-6.79 (d, J=3.0 Hz, 1H), 6.83-6.88 (t, J1=7.5 Hz, J2=7.8 Hz, 2H), 6.96-7.09 (m, 2H), 7.40-7.48 (m, 4H), 7.53-7.55 (d, J=7.2 Hz, 1H), 7.84-7.85 (d, J=1.5 Hz, 1H), 7.87 (s, 1H).

LC/MS (M+1)$^+$: 458.

EXAMPLE 46

Preparation of Compound 46: 2-methyl-2-{1-[3-(3,4,5-trimethoxy-phenoxy)-propyl]-1H-indol-4-yloxy}-propionic acid Compound 46 was prepared in a manner similar to that described in Example 1.

$^1$H NMR (ppm): CDCl$_3$ δ 1.67 (s, 6H), 2.26-2.30 (t, J=6.0 Hz, 2H), 3.77-3.85 (m, 11H), 4.32-4.36 (t, J=6.6 Hz, 2H), 6.53-6.54 (d, J=3.0 Hz, 1H), 6.56-6.58 (d, J=6.9 Hz, 1H), 7.01-7.02 (d, J=2.7 Hz, 1H), 7.05-7.07 (d, J=7.2 Hz, 2H).

LC/MS (M+1)$^+$: 444.

EXAMPLE 47

Preparation of Compound 47: 2-{1-[3-(4-methoxy-phenylsulfanyl)-propyl]-1H-indol-4-yloxy}-2-methyl-propionic acid Compound 47 was prepared in a manner similar to that described in Example 1.

$^1$H NM (ppm): CDCl$_3$ δ 1.65 (s, 6H), 2.04-2.08 (t, J=6.6 Hz, 2H), 2.71-2.75 (t, J=6.6 Hz, 2H), 3.78 (s, 3H), 4.20-4.25 (t, J=6.6 Hz, 2H), 6.51-6.52 (d, J=3.0 Hz, 1H), 6.56-6.59 (t, J=3.9 Hz, 1H), 6.79-6.83 (dd, J1=2.1 Hz, J2=4.5 Hz, 1H), 7.00-7.01 (d, J=3.0 Hz, 1H), 7.04-7.06 (d, J=3.9 Hz, 2H), 7.28-7.31 (dd, J1=2.1 Hz, J2=4.5 Hz, 2H).

LC/MS (M+1)$^+$: 400.

EXAMPLE 48

Preparation of Compound 48: 2-methyl-2-{1-[3-(4-nitro-phenylsulfanyl)-propyl]-1H-indol-4-yloxy}-propionic acid Compound 48 was prepared in a manner similar to that described in Example 1.

$^1$H NMR (ppm): CDCl$_3$ δ 1.68 (s, 6H), 2.19-2.33 (t, J=6.6 Hz, 2H), 2.88-2.93 (t, J=7.2 Hz, 2H), 4.26-4.31 (t, J=6.3 Hz, 2H), 6.56-6.57 (d, J=3.0 Hz, 1H), 6.59-6.62 (m, 2H), 7.04-7.07 (m, 3H), 7.11-7.16 (dd, J1=1.8 Hz, J2=4.8 Hz, 2H), 8.00-8.04 (dd, J1=1.8 Hz, J2=5.1 Hz, 2H).

LC/MS (M+1)$^+$: 417.

EXAMPLE 49

Preparation of Compound 49: 2-{1-[3-(dibenzofuran-1-yloxy)-propyl]-1H-indol-4-yloxy}-2-methyl-propionic acid Compound 49 was prepared in a manner similar to that described in Example 1.

$^1$H NMR (ppm): CDCl$_3$ δ 1.65 (s, 6H), 2.30-2.34 (t, J=6.0 Hz, 2H), 3.93-3.97 (t, J=5.7 Hz, 2H), 4.36-4.41 (t, J=6.6 Hz, 2H), 6.51-6.52 (t, J=3.3 Hz, 1H), 6.56-6.58 (d, J=7.5 Hz, 2H), 7.00-7.06 (m, 3H), 7.10-7.13 (d, J=8.1 Hz, 1H), 7.27-7.34 (m, 2H), 7.39-7.46 (m, 2H), 7.51-7.54 (d, J=7.5 Hz, 1H), 7.83-7.86 (d, J=7.8 Hz, 1H).

LC/MS (M+1)$^+$: 444.

EXAMPLE 50

Preparation of Compound 50: diethyl-(2-{1-[3-(7-propyl-3-trifluoromethyl-benzo[d]isoxazol-6-yloxy)-propyl]-1H-indol-5-yloxy}-ethyl)-amine Compound 50 was prepared in a manner similar to that described in Example 1.

$^1$H NMR (ppm): CDCl$_3$ δ 1.02 (t, J=7.5 Hz, 3H), 1.08 (t, J=7.2 Hz, 6H), 1.74-1.81 (m, 2H), 2.33 (p, 2H), 2.66 (q, J=7.2 Hz, 4H), 2.91 (t, J=6.3 Hz, 2H), 2.98 (t, J=7.5 Hz, 2H), 3.96 (t, J=5.4 Hz, 2H), 4.09 (t, J=6.3 Hz, 2H), 4.34 (t, J=6.6 Hz, 2H), 6.38 (d, J=3.0 Hz, 1H), 6.85 (dd, J=2.1, 8.7 Hz, 1H), 6.89 (d, J=9 Hz, 3H), 7.00 (d, J=3.3 Hz, 1H), 7.09 (d, J=2.4 Hz, 1H), 7.21 (d, J=9.6 Hz, 1H), 7.49 (d, J=8.7 Hz, 1H).

LC/MS (M+1)$^+$: 518.

EXAMPLE 51

Preparation of Compound 51: 2-{1-[3-(1-carboxymethyl-1H-indol-5-yloxy)-propyl]-1H-indol-4-yloxy}-2-methyl-propionic acid tert-butyl ester Compound 51 was prepared in a manner similar to that described in Example 2.

$^1$H NMR (ppm): CDCl$_3$+MeOH-d$_4$ δ 1.42 (s, 6H), 1.62 (s, 6H), 2.26 (p, 2H), 3.89 (t, J=5.7 Hz, 2H), 4.32 (t, J=6.6 Hz, 2H), 4.81 (s, 2H), 6.40-6.44 (m, 2H), 6.53 (d, J=3.0 Hz, 1H), 6.80 (dd, J=2.4, 8.7 Hz, 1H), 6.96-7.02 (m, 5H), 7.10 (d, J=8.7 Hz, 1H).

LC/MS (M+1)$^+$: 507.

EXAMPLE 52

Preparation of Compound 52: 2-{1-[3-(1H-indol-5-yloxy)-propyl]-1H-indol-4-yloxy}-2-methyl-propionic acid Compound 52 was prepared in a manner similar to that described in Example 1.

$^1$H NMR (ppm): CDCl$_3$+MeOH-d$_4$ δ 1.62 (s, 6H), 2.28 (p, 2H), 3.91 (t, J=5.7 Hz, 2H), 4.36 (t, J=6.6 Hz, 2H), 6.42-6.44 (m, 1H), 6.49 (dd, J=0.6, 3.3 Hz, 1H), 6.58 (dd, J=0.6, 7.5 Hz, 1H), 6.86 (dd, J=2.4, 8.7 Hz, 1H), 7.02-7.07 (m, 3H), 7.11-7.17 (m, 2H), 7.27 (d, J=8.7 Hz, 1H).

LC/MS (M+1)$^+$: 393.

EXAMPLE 53

Preparation of Compound 53: 7-propyl-6-{3-[1-(2H-tetrazol-5-ylmethyl)-1H-indol-5-yloxy]-propoxy}-3-trifluoromethyl-benzo[d]isoxazole Compound 53 was prepared in a manner similar to that described in Example 2.

$^1$H NMR (ppm): MeOH-d$_4$ δ 0.88 (t, J=7.2 Hz, 3H), 1.59-1.68 (m, 2H), 2.25-2.31 (m, 2H), 2.85-2.91 (m, 2H), 4.19 (t, J=6.0 Hz, 2H), 4.34 (t, J=6.0 Hz, 2H), 5.57 (s, 2H), 6.78 (dd, J=9.0, 2.2 Hz, 1H), 7.04 (d, J=2.1 Hz, 1H), 7.21-7.30 (m, 3H), 7.60 (d, J=8.4 Hz, 1H).

LC/MS (M+1)$^+$: 501.

EXAMPLE 54

Preparation of Compound 54: 7-propyl-6-{3-[1-(2H-tetrazol-5-ylmethyl)-1H-indol-6-yloxy]-propoxy}-3-trifluoromethyl-benzo[d]isoxazole Compound 54 was prepared in a manner similar to that described in Example 2.

$^1$H NMR (ppm): DMSO-d$_6$ δ 0.79-0.85 (m, 3H), 1.53-1.65 (m, 2H), 2.13-2.30 (m, 2H), 2.80-2.90 (m, 2H), 4.14-4.19 (m, 2H), 4.30-4.36 (m, 2H), 5.66 (s, 2H), 6.37 (d, J=3.3 Hz, 1H), 6.69 (d, J=8.4 Hz, 1H), 7.05 (bs, 1H), 7.25 (d, J=3.3 Hz, 1H), 7.36-7.43 (m, 2H), 7.74 (d, J=8.7 Hz, 1H).

LC/MS (M+1)$^+$: 501.

EXAMPLE 55

Preparation of Compound 55: {4-[3-(7-trifluoromethyl-quinolin-4-yloxy)-propoxy]-indol-1-yl}-acetic acid Compound 55 was prepared in a manner similar to that described in Example 2.

$^1$H NMR (ppm): CDCl$_3$+MeOH-d$_4$ δ 2.46 (m, 2H), 4.34 (t, J=5.7 Hz, 2H), 4.46 (t, J=6.0 Hz, 2H), 4.75 (s, 2H), 6.49 (d, J=7.5 Hz, 1H), 6.56 (d, J=3.3 Hz, 1H), 6.83 (m, 2H), 6.89 (d, J=2.7 Hz, 1H), 7.03 (t, J=8.1 Hz, 1H), 7.60 (dd, J=1.5, 9.0 Hz) 8.19 (s, 1H). 8.27 (d, J=8.7 Hz, 1H) 8.64 (d, J=5.4 Hz, 1H).

LC/MS (M+1)$^+$: 445.

EXAMPLE 56

Preparation of Compound 56: {4-[3-(pyridin-4-ylsulfanyl)-propoxy]-indol-1-yl}-acetic acid Compound 56 was prepared in a manner similar to that described in Example 2.

$^1$H NMR (ppm): CDCl$_3$+MeOH-d$_4$ δ 2.26 (m, 2H), 3.29 (t, J=7.2 Hz, 2H), 4.27 (t, J=5.4 Hz, 2H), 4.84 (s, 2H), 6.50 (d, J=7.5 Hz, 1H) 6.65 (d, J=3.3 Hz, 1H) 6.92, (d, J=8.1 Hz, 1H) 7.07 (m, 2H), 7.16 (m, 2H), 8.12 (d, J=6.0 Hz, 1H).

LC/MS (M+1)$^+$: 343.

EXAMPLE 57

Preparation of Compound 57: {4-[4-(7-propyl-3-trifluoromethyl-benzo[d]isoxazol-6-yloxy)-butoxy]-indol-1-yl}-acetic acid Compound 57 was prepared in a manner similar to that described in Example 2.

$^1$H NMR (ppm): CDCl$_3$+MeOH-d$_4$ δ 0.99 (t, J=7.2 Hz, 3H), 1.60-1.82 (m, 2H), 2.15 (bs, 4H), 2.89-3.00 (m, 2H), 4.23-4.33 (m, 4H), 4.88 (s, 2H), 6.54-6.60 (m, 2H), 6.90-6.98 (m, 1H), 7.03-7.15 (m, 2H), 7.20-7.25 (m, 1H), 7.61 (d, J=8.1 Hz, 1H).

LC/MS (M+1)$^+$: 491.

EXAMPLE 58

Preparation of Compound 58: {4-[5-(7-propyl-3-trifluoromethyl-benzo[d]isoxazol-6-yloxy)-pentyloxy]-indol-1-yl}-acetic acid Compound 58 was prepared in a manner similar to that described in Example 2.

$^1$H NMR (ppm): CDCl$_3$+MeOH-d$_4$ δ 0.94 (t, J=7.2 Hz, 3H), 1.65-1.72 (m, 2H), 1.75-1.86 (m, 2H), 1.92-2.02 (m, 4H), 2.91 (t, J=7.2 Hz, 2H), 4.12-4.22 (m, 4H), 4.86 (s, 2H), 6.50-6.55 (m, 2H), 6.87 (d, J=8.1 Hz, 1H), 7.00-7.10 (m, 2H), 7.20 (d, J=9.0 Hz, 1H), 7.58 (d, J=8.4 Hz, 1H).

LC/MS (M+1)$^+$: 505.

EXAMPLE 59

Preparation of Compound 59: {1-[4-(7-propyl-3-trifluoromethyl-benzo[d]isoxazol-6-yloxy)-butyl]-1H-indol-4-yloxy}-acetic acid Compound 59 was prepared in a manner similar to that described in Example 1.

$^1$H NMR (ppm): CDCl$_3$+MeOH-d$_4$ δ 0.89 (t, J=7.2 Hz, 3H), 1.55-1.70 (m, 2H), 1.80-1.85 (m, 2H), 2.01-2.10 (m, 2H), 2.80-2.90 (m, 2H), 4.06 (t, J=5.7 Hz, 2H), 4.24 (t, J=6.3 Hz, 2H), 4.72 (s, 2H), 6.40 (d, J=6.3 Hz, 1H), 6.58 (d, J=3.0 Hz, 1H), 7.00-7.08 (m, 2H), 7.10-7.16 (m, 2H), 7.55 (d, J=9.0 Hz, 1H).

LC/MS (M+1)$^+$: 491.

EXAMPLE 60

Preparation of Compound 60: {4-[2-(7-propyl-3-trifluoromethyl-benzo[d]isoxazol-6-yloxy)-ethoxy]-indol-1-yl}-acetic acid Compound 60 was prepared in a manner similar to that described in Example 2.

$^1$H NMR (ppm): CDCl$_3$+MeOH-d$_4$ δ 0.90 (t, J=7.2 Hz, 3H), 1.50-1.79 (m, 2H), 2.85-2.95 (m, 2H), 4.47-4.60 (m, 4H), 4.80 (s, 2H), 6.48 (d, J=3.0 Hz, 1H), 6.59 (d, J=7.8 Hz, 1H), 6.93 (d, J=8.1 Hz, 1H), 7.00-7.13 (m, 2H), 7.33 (d, J=9.0 Hz, 1H), 7.63 (d, J=8.7 Hz, 1H).

LC/MS (M+1)$^+$: 463.

EXAMPLE 61

Preparation of Compound 61: {1-[5-(7-propyl-3-trifluoromethyl-benzo[d]isoxazol-6-yloxy)-pentyl]-1H-indol-4-yloxy}-acetic acid Compound 61 was prepared in a manner similar to that described in Example 1.

$^1$H NMR (ppm): CDCl$_3$+MeOH-d$_4$ δ 0.92 (t, J=7.2 Hz, 3H), 1.45-1.70 (m, 4H), 1.78-1.95 (m, 4H), 2.75-2.89 (m, 2H), 3.98-4.20 (m, 4H), 4.58 (s, 2H), 6.44 (bs, 1H), 6.64 (bs, 1H), 6.90-7.07 (m, 4H), 7.45-7.57 (m, 1H).

LC/MS (M+1)$^+$: 505.

EXAMPLE 62

Preparation of Compound 62: {1-[3-(1-phenyl-1H-pyrazolo[3,4-d]pyrimidin-4-yloxy)-propyl]-1H-indol-4-yloxy}-acetic acid Compound 62 was prepared in a manner similar to that described in Example 1.

$^1$H NMR (ppm): CDCl$_3$+MeOH-d$_4$ δ 2.06 (p, 2H), 3.30 (t, J=6.3 Hz, 2H), 4.17 (t, J=6.6 Hz, 2H), 4.74 (s, 2H) 6.42 (d, J=7.5 Hz, 1H), 6.66 (d, J=3.0 Hz, 1H), 6.98-7.10 (m, 3H), 7.37-7.50 (m, 3H), 7.71 (s, 1H), 7.95-7.99 (m, 2H), 8.22 (s, 1H).

LC/MS (M+1)$^+$: 444.

EXAMPLE 63

Preparation of Compound 63: 2-methyl-2-(1-{3-[4-(2H-tetrazol-5-yl)-phenoxy]-propyl}-1H-indol-4-yloxy)-propionic acid Compound 63 was prepared in a manner similar to that described in Example 1.
$^1$H NMR (ppm): CDCl$_3$+MeOH-d$_4$ δ 1.62 (s, 6H), 2.51 (p, 2H), 4.17 (t, J=6.6 Hz, 2H), 4.52 (t, J=6.3 Hz, 2H), 6.46-6.54 (m, 2H), 6.88-7.03 (m, 5H), 7.90 (d, J=8.7 Hz, 2H).
LC/MS (M+1)$^+$: 422.

EXAMPLE 64

Preparation of Compound 64: 2-methyl-2-(1-{3-[4-(2-methyl-2H-tetrazol-5-yl)-phenoxy]-propyl}-1H-indol-4-yloxy)-propionic acid Compound 64 was prepared in a manner similar to that described in Example 1.
$^1$H NMR (ppm): CDCl$_3$+MeOH-d$_4$ δ 1.70 (s, 6H), 2.59 (p, 2H), 3.89 (s, 2H), 4.25 (t, J=6.6 Hz, 2H), 4.60 (t, J=6.6 Hz, 2H), 6.59-6.64 (m, 2H), 7.00-7.16 (m, 5H), 8.00 (d, J=8.7 Hz, 2H).
LC/MS (M+1)$^+$: 437.

EXAMPLE 65

Preparation of Compound 65: 2-(1-{3-[4-(2-benzyl-2H-tetrazol-5-yl)-phenoxy]-propyl}-1H-indol-4-yloxy)-2-methyl-propionic acid Compound 65 was prepared in a manner similar to that described in Example 1.
$^1$H NMR (ppm): CDCl$_3$+MeOH-d$_4$ δ 1.66 (s, 6H), 2.58 (p, 2H), 4.24 (t, J=6.3 Hz, 2H), 4.59 (t, J=6.3 Hz, 2H), 5.15 (s, 2H), 6.58-6.61 (m, 2H), 7.08-7.15 (m, 5H), 7.35-7.48 (m, 5H), 8.09 (d, J=8.7 Hz, 2H).
LC/MS (M+1)$^+$: 512.

EXAMPLE 66

Preparation of Compound 66: 2-methyl-2-(1-{3-[4-(5-methyl-[1,2,4]oxadiazol-3-yl)-phenoxy]-propyl}-1H-indol-4-yloxy)-propionic acid Compound 66 was prepared in a manner similar to that described in Example 1.
$^1$H NMR (ppm): CDCl$_3$+MeOH-d$_4$ δ 1.71 (s, 6H), 2.29 (p, 2H), 2.64 (s, 3H), 3.90 (t, J=5.4 Hz, 2H), 4.34 (t, J=6.3 Hz, 2H), 6.55-6.60 (m, 2H), 6.89 (d, J=8.4 Hz, 2H), 7.00-7.07 (m, 5H), 7.95 (d, J=8.4 Hz, 2H).
LC/MS (M+1)$^+$: 436.

EXAMPLE 67

Preparation of Compound 67: 2-{1-[3-(6-benzoyl-naphthalen-2-yloxy)-propyl]-1H-indol-4-yloxy}-2-methyl-propionic acid Compound 67 was prepared in a manner similar to that described in Example 1.
$^1$H NMR (ppm): CDCl$_3$ δ 1.65 (s, 6H), 2.33-2.37 (t, J=5.7 Hz, 2H), 3.98-4.01 (t, J=5.4 Hz, 2H), 4.36-4.40 (t, J=6.0 Hz, 2H), 6.53 (bs, 2H), 7.00-7.10 (m, 4H), 7.20-7.23 (m, 1H), 7.47-7.52 (t, J1=7.2 Hz, J2=7.5 Hz, 2H), 7.57-7.59 (d, J=6.9 Hz, 2H), 7.70-7.73 (d, J=8.7 Hz, 2H), 7.79-7.83 (m, 3H), 7.79-7.88 (d, J=8.4 Hz, 1H), 8.19 (s, 1H).
LC/MS (M+1)$^+$: 508.

EXAMPLE 68

Preparation of Compound 68: 2-{1-[3-(9H-carbazol-3-yloxy)-propyl]-1H-indol-4-yloxy}-2-methyl-propionic acid Compound 68 was prepared in a manner similar to that described in Example 1.
$^1$H NMR (ppm): CDCl$_3$ δ 1.65 (s, 6H), 2.28-2.32 (t, J=6.0 Hz, 2H), 3.88-3.91 (t, J=5.4 Hz, 2H), 4.35-4.40 (t, J=6.6 Hz, 2H), 6.50-6.51 (d, J=3.0 Hz, 1H), 6.57-6.59 (d, J=7.5 Hz, 1H), 6.72-6.72 (d, J=1.8 Hz, 1H), 6.81-6.84 (m, 2H), 7.03-7.05 (m, 2H), 7.11-7.13 (d, J=8.1 Hz, 1H), 7.13-7.21 (m, 1H), 7.32-7.34 (d, J=6.0 Hz, 2H), 7.89-7.96 (m, 3H).
LC/MS (M+1)$^+$: 443.

EXAMPLE 69

Preparation of Compound 69: {4-[3-(7-chloro-quinolin-4-yloxy)-propoxy]-indol-1-yl}-acetic acid Compound 69 was prepared in a manner similar to that described in Example 1.
$^1$H NMR (ppm): CDCl$_3$+MeOH-d$_4$ δ 2.42 (m, 2H), 4.32 (t, J=5.4 Hz, 2H), 4.52 (t, J=6.9 Hz, 2H), 4.82 (s, 2H), 6.41 (d, J=7.5 Hz, 1H), 6.59 (d, J=3.3 Hz, 1H), 6.63 (d, J=5.7 Hz, 11H), 6.91 (m, 2H), 7.04 (d, J=3.3 Hz, 1H), 7.37 (dd, J=1.8, 8.7 Hz, 1H), 7.82 (d, J=1.8 Hz, 1H), 8.04 (d, J=9.0 Hz, 1H), 8.35 (d, J=5.7 Hz, 1H).
LC/MS (M+1)$^+$: 411.

EXAMPLE 70

Preparation of Compound 70: {4-[3-(8-trifluoromethyl-quinolin-4-yloxy)-propoxy]-indol-1-yl}-acetic acid Compound 70 was prepared in a manner similar to that described in Example 2.
$^1$H NMR (ppm): CDCl$_3$+MeOH-d$_4$ δ 2.44 (m, 2H), 4.10 (m, 2H), 4.32 (m, 2H), 4.75 (s, 2H), 6.49 (d, J=7.2 Hz, 1H), 6.60 (d, J=3.3 Hz, 1H), 6.75 (d, J=5.1 Hz, 1H), 6.84 (m, 1H), 6.96 (m, 1H), 7.03 (m, 1H), 7.46 (m, 1H), 7.99 (d, J=6.96 Hz, 1H), 8.36 (d, J=7.8 Hz, 1H), 8.73 (d, J=5.1 Hz, 1H).
LC/MS (M+1)$^+$: 445.

EXAMPLE 71

Preparation of Compound 71: {4-[3-(2-methyl-quinolin-6-yloxy)-propoxy]-indol-1-yl}-acetic acid Compound 71 was prepared in a manner similar to that described in Example 2.
$^1$H NMR (ppm): CDCl$_3$+MeOH-d$_4$ δ 2.03 (m, 2H), 2.54 (s, 3H), 4.22 (m, 4H), 4.67 (s, 2H), 6.38 (d, J=7.5 Hz, 1H), 6.50 (d, J=3.3 Hz, 1H), 6.89 (m, 2H), 7.06 (d, J=8.1 Hz, 1H), 7.17 (d, J=7.5 Hz, 1H), 7.53 (m, 1H), 7.76 (d, J=7.8 Hz, 2H), 7.88 (d, J=9.3 Hz, 1H).
LC/MS (M+1)$^+$: 391.

EXAMPLE 72

Preparation of Compound 72: 4-{3-[4-(2H-tetrazol-5-yl)-phenoxy]-propoxy}-1-{3-[4-(2H-tetrazol-5-yl)-phenoxy]-propyl}-1H-indole Compound 72 was prepared in a manner similar to that described in Example 2.

$^1$H NMR (ppm): CDCl$_3$+MeOH-d$_4$ δ 2.53-2.64 (m, 4H), 4.20-4.26 (m, 4H), 4.55 (t, J=6.6 Hz, 2H), 4.91 (t, J=7.2 Hz, 2H), 6.50 (d, J=7.5 Hz, 1H), 6.59 (d, J=3.0 Hz, 1H) 6.90-6.96 (m, 5H), 7.07-7.13 (m, 2H), 7.93-7.98 (m, 4H).

LC/MS (M+1)$^+$: 538.

EXAMPLE 73

Preparation of Compound 73: (5-{3-[4-(5-methyl-[1,2,4]oxadiazol-3-yl)-phenoxy]-propoxy}-indol-1-yl)-acetic acid Compound 73 was prepared in a manner similar to that described in Example 2.

$^1$H NMR (ppm): CDCl$_3$+MeOH-d$_4$ δ 2.29 (p, 2H), 2.64 (s, 3H), 4.19-4.26 (m, 4H), 4.79 (s, 2H), 6.45 (d, J=3.0 Hz, 1H), 6.88 (dd, J=2.4, 8.7 Hz, 1H) 6.98 (d, J=9.0 Hz, 2H), 7.06 (d, J=3.3 Hz, 1H), 7.11-7.16 (m, 2H), 7.94 (d, J=9.0 Hz, 2H).

LC/MS (M+1)$^+$: 408.

EXAMPLE 74

Preparation of Compound 74: 5-{1-[3-(7-propyl-3-trifluoromethyl-benzo[d]isoxazol-6-yloxy)-propyl]-1H-indol-5-ylmethylene}-thiazolidine-2,4-dione Compound 74 was prepared in a manner similar to that described in Example 1.

$^1$H NMR (ppm): CDCl$_3$+DMSO-d$_4$ δ 1.03 (t, J=7.5 Hz, 3H), 1.74-1.82 (m, 2H), 2.37 (p, 2H), 2.98 (t, J=7.5 Hz, 2H), 4.02 (t, J=5.7 Hz, 2H), 4.44 (t, J=6.6Hz, 2H), 6.57 (d, J=3.0 Hz, 1H), 6.95 (d, J=8.7 Hz, 1H), 7.14 (d, J=3.0 Hz, 1H), 7.32 (dd, J=1.8, 8.4 Hz, 1H), 7.42 (d, J=8.7 Hz, 1H), 7.53 (d, J=8.7 Hz, 1H), 7.79 (s, 1H), 7.91 (s, 1H).

LC/MS (M+1)$^+$: 530.

EXAMPLE 75

Preparation of Compound 75: 2-methyl-2-(1-{3-[4-(5-phenyl-[1,2,4]oxadiazol-3-yl)-phenoxy]-propyl}-1H-indol-4-yloxy)-propionic acid Compound 75 was prepared in a manner similar to that described in Example 1.

$^1$H NMR (ppm): CDCl$_3$+MeOH-d$_4$ δ 1.67 (s, 6H), 2.30 (p, 2H), 3.91 (t, J=5.4 Hz, 2H), 4.35 (t, J=6.6 Hz, 2H), 6.51 (dd, J=2.4, 6.0 Hz, 1H), 6.56 (d, J=3.0 Hz, 1H), 6.94-7.02 (m, 5H), 7.52-7.60 (m, 3H), 8.07 (d, J=8.7 Hz, 2H), 8.19 (d, J=8.7 Hz, 1H).

LC/MS (M+1)$^+$: 498.

EXAMPLE 76

Preparation of Compound 76: 2-methyl-2-{1-[3-(3-phenyl-7-propyl-benzo[d]isoxazol-6-yloxy)-propyl]-1H-indol-4-yloxy}-propionic acid Compound 76 was prepared in a manner similar to that described in Example 1.

$^1$H NMR (ppm): CDCl$_3$+MeOH-d$_4$ δ 1.04 (t, J=7.2 Hz, 3H), 1.67 (s, 6H), 1.77-1.83 (m, 2H), 2.34 (p, 2H), 3.00 (t, J=7.6 Hz, 2H), 4.01 (t, J=5.4 Hz, 2H), 4.39 (t, J=6.6 Hz, 2H), 6.51-6.61 (m, 2H), 6.85 (d, J=8.7 Hz, 1H), 7.01-7.13 (m, 4H), 7.50-7.62 (m, 3H), 7.90-7.92 (m, 2H).

LC/MS (M+1)$^+$: 513.

EXAMPLE 77

Preparation of Compound 77: 2-[1-(3-carbazol-9-yl-propyl)-1H-indol-4-yloxy]-2-methyl-propionic acid Compound 77 was prepared in a manner similar to that described in Example 1.

$^1$H NMR (ppm): CDCl$_3$ d 1.67 (s, 6H), 2.41-2.45 (t, J=6.9 Hz, 2H), 4.10-4.15 (t, J=7.2 Hz, 2H), 4.25-4.30 (t, J=6.9 Hz, 2H), 6.57-6.58 (d, J=3.0 Hz, 2H), 6.61 (s, 1H), 6.88-6.91 (d, J=8.1 Hz, 1H), 7.01-7.05 (m, 2H), 7.16-7.21 (m, 4H), 7.36-7.41 (t, J1=7.2 Hz, J2=7.5 Hz, 2H), 8.06-8.09 (d, J=7.8 Hz, 2H).

LC/MS (M+1)$^+$: 427.

EXAMPLE 78

Preparation of Compound 78: 2-methyl-2-[1-(3-phenoxazin-10-yl-propyl)-1H-indol-4-yloxy]-propionic acid Compound 78 was prepared in a manner similar to that described in Example 1.

$^1$H NMR (ppm): CDCl$_3$ δ 1.69 (s, 6H), 2.20-2.25 (t, J=7.8 Hz, 2H), 4.28-4.42 (t, J=6.3 Hz, 2H), 6.13-6.15 (d, J=6.6 Hz, 2H), 6.61-6.83 (m, 8H), 7.01-7.04 (m, 4H).

LC/MS (M+1)$^+$: 443.

EXAMPLE 79

Preparation of Compound 79: 2-methyl-2-[1-(3-phenothiazin-10-yl-propyl)-1H-indol-4-yloxy]-propionic acid Compound 79 was prepared in a manner similar to that described in Example 1.

$^1$H NMR (ppm): CDCl$_3$ δ 1.61 (s, 6H), 2.26-2.30 (t, J=6.0 Hz, 2H), 3.74-3.78 (t, J=5.7 Hz, 2H), 4.21-4.25 (t, J=6.6 Hz, 2H), 6.36-6.37 (d, J=2.7 Hz, 1H), 6.55 (s, 1H), 6.72-6.75 (d, J=8.1 Hz, 2H), 6.83-6.84 (d, J=3.0 Hz, 1H), 6.92-6.97 (m, 4H), 7.08-7.16 (m, 4H), 7.20-7.23 (m, 2H).

LC/MS (M+1)$^+$: 459.

EXAMPLE 80

Preparation of Compound 80: 6-{3-[1-(2-methyl-2H-tetrazol-5-ylmethyl)-1H-indol-4-yloxy]-propoxy}-7-propyl-3-trifluoromethyl-benzo[d]isoxazole Compound 80 was prepared in a manner similar to that described in Example 2.

$^1$H NMR (ppm): CDCl$_3$+MeOH-d$_4$ δ 0.85-0.95 (m, 3H), 1.50-1.75 (m, 2H), 2.41 (t, J=6.0 Hz, 2H), 2.89 (t, J=7.5 Hz, 2H), 4.28 (s, 3H), 4.30-4.40 (m, 4H), 5.53 (s, 2H), 6.56 (dd, J=6.0, 3.0 Hz, 1H), 6.60 (d, J=3.3 Hz, 1H), 7.05-7.20 (m, 4H), 7.55 (d, J=9.0 Hz, 1H).

LC/MS (M+1)$^+$: 515.

EXAMPLE 81

Preparation of Compound 81: 6-{3-[1-(1-methyl-1H-tetrazol-5-ylmethyl)-1H-indol-4-yloxy]-propoxy}-7-propyl-3-trifluoromethyl-benzo[d]isoxazole Compound 81 was prepared in a manner similar to that described in Example 2.

$^1$H NMR (ppm): CDCl$_3$+MeOH-d$_4$ δ 0.85-0.92 (m, 3H), 1.65-1.80 (m, 2H), 2.43 (t, J=6.0 Hz, 2H), 2.80-3.00 (m, 2H), 3.71 (s, 3H), 4.30-4.42 (m, 4H), 5.71 (s, 2H), 6.60 (d, J=7.8 Hz, 1H), 6.66 (d, J=3.3 Hz, 1H), 6.94 (d, J=8.4 Hz, 1H), 7.06-7.21 (m, 3H), 7.56 (d, J=8.8 Hz, 1H).

LC/MS (M+1)$^+$: 515.

EXAMPLE 82

Preparation of Compound 82: {4-[3-methyl-5-(7-propyl-3-trifluoromethyl-benzo[d]isoxazol-6-yloxy)-pentyloxy]-indol-1-yl}-acetic acid Compound 82 was prepared in a manner similar to that described in Example 2.

$^1$H NMR (ppm): CDCl$_3$+MeOH-d$_4$ δ 0.95 (t, J=7.2 Hz, 3H), 1.17-1.63 (m, 3H), 1.85-1.63 (m, 4H), 2.00-2.20 (m, 4H), 2.85-2.95 (m, 2H), 4.12-4.25 (m, 4H), 4.72 (s, 2H), 6.40-6.58 (m, 2H), 6.75-6.90 (m, 1H), 6.96 (bs, 1H), 7.02-7.15 (m, 2H), 7.45-7.60 (m, 1H).

LC/MS (M+1)$^+$: 519.

EXAMPLE 83

Preparation of Compound 83: {5-[3-methyl-5-(7-propyl-3-trifluoromethyl-benzo[d]isoxazol-6-yloxy)-pentyloxy]-indol-1-yl}-acetic acid Compound 83 was prepared in a manner similar to that described in Example 2.

$^1$H NMR (ppm): CDCl$_3$+MeOH-d$_4$ δ 0.95-1.02 (m, 3H), 1.05-1.12 (m, 3H), 1.65-1.83 (m, 4H), 1.89-2.10 (m, 4H), 2.85-2.95 (m, 2H), 4.03-4.13 (m, 2H), 4.15-4.25 (m, 2H), 4.74 (s, 2H), 6.39 (d, J=3.0 Hz, 1H), 6.82 (d, J=6.6 Hz, 1H), 7.05-7.20 (m, 4H). 7.55 (d, J=9.0 Hz, 1H).

LC/MS (M+1)$^+$: 519.

EXAMPLE 84

Preparation of Compound 84: {1-[2-(7-propyl-3-trifluoromethyl-benzo[d]isoxazol-6-yloxy)-ethyl]-1H-indol-4-yloxy}-acetic acid Compound 84 was prepared in a manner similar to that described in Example 1.

$^1$H NMR (ppm): CDCl$_3$+MeOH-d$_4$ δ 0.87 (t, J=7.5 Hz, 3H), 1.49-1.58 (m, 2H), 2.74 (t, J=7.5 Hz, 2H), 4.40-4.46 (m, 2H), 4.60-4.65 (m, 2H), 4.74 (s, 2H), 6.46 (d, J=6.0 Hz, 1H), 6.65-6.70 (m, 1H), 7.05-7.12 (m, 3H), 7.18-7.20 (m, 1H), 7.53 (d, J=8.1 Hz, 1H).

LC/MS (M+1)$^+$: 463.

EXAMPLE 85

Preparation of Compound 85: 2-methyl-2-[1-(4-phenoxazin-10-yl-butyl)-1H-indol-4-yloxy]-propionic acid Compound 85 was prepared in a manner similar to that described in Example 1.

HRMS-FAB (M$^+$): 456.20.

EXAMPLE 86

Preparation of Compound 86: 2-{1-[3-(5-chloro-benzooxazol-2-ylamino)-propyl]-1H-indol-4-yloxy}-2-methyl-propionic acid Compound 86 was prepared in a manner similar to that described in Example 1.

LC/MS (M+1)$^+$: 428.

EXAMPLE 87

Preparation of Compound 87: {1-[3-(3-phenyl-7-propyl-benzo[d]isoxazol-6-yloxy)-propyl]-1H-indol-5-yloxy}-acetic acid Compound 87 was prepared in a manner similar to that described in Example 1.

$^1$H NMR (ppm): CDCl$_3$+MeOH-d$_4$ δ 1.05 (t, J=7.5 Hz, 3H), 1.77-1.85 (m, 2H), 2.32 (m, 2H), 3.00 (t, J=7.5 Hz, 2H), 3.97 (t, J=5.4 Hz, 2H), 4.37 (t, J=6.0 Hz, 2H), 4.61 (s, 2H), 6.38 (d, J=2.7 Hz, 1H), 6.85 (d, J=8.7 Hz, 1H), 6.92 (dd, J=2.2, 8.4 Hz, 1H), 7.05 (d, J=3.0 Hz, 1H), 7.08 (d, J=2.1 Hz, 1H), 7.26 (d, J=9.0 Hz, 1H), 7.50-7.55 (m, 3H), 7.61 (d, J=8.7 Hz, 1H), 7.89-7.92 (m, 2H).

LC/MS (M+1)$^+$: 485.

EXAMPLE 88

Preparation of Compound 88: {5-[3-(3-phenyl-7-propyl-benzo[d]isoxazol-6-yloxy)-propoxy]-indol-1-yl}-acetic acid Compound 88 was prepared in a manner similar to that described in Example 2.

$^1$H NMR (ppm): CDCl$_3$ δ 0.95 (t, J=7.5 Hz, 3H), 1.68-1.73 (m, 2H), 2.38 (p, 2H), 2.91 (t, J=7.5 Hz, 2H), 4.31-4.37 (m, 4H), 4.86 (s, 2H), 6.57 (d, J=7.2 Hz, 1H), 6.66 (d, J=4.4 Hz, 1H), 6.86 (d, J=8.4 Hz, 1H), 6.97-7.02 (m, 3H), 7.24-7.64 (m, 4H), 7.90-7.92 (m, 2H).

LC/MS (M+1)$^+$: 485.

EXAMPLE 89

Preparation of Compound 89: 3-{1-[3-(7-propyl-3-trifluoromethyl-benzo[d]isoxazol-6-yloxy)-propyl]-1H-indol-5-yloxy}-propionic acid Compound 89 is prepared in a manner similar to that described in Example 1.

EXAMPLE 90

Preparation of Compound 90: 3-{5-[3-(7-propyl-3-trifluoromethyl-benzo[d]isoxazol-6-yloxy)-propoxy]-indol-1-yl}-propionic acid Compound 90 was prepared in a manner similar to that described in Example 2.
$^1$H NMR (ppm): CDCl$_3$ δ 0.94 (t, J=7.5 Hz, 3H), 1.65-1.72 (m, 2H), 2.34 (p, 2H), 2.83-2.93 (m, 4H), 4.22 (t, J=6.0 Hz, 2H), 4.31 (t, J=6.0 Hz, 2H), 4.39 (t, J=6.9 Hz, 2H), 6.70 (d, J=3 Hz, 1H), 6.87 (dd, J=2.4, 8.7 Hz, 1H), 7.06-7.10 (m, 3H), 7.21 (d, J=9.0 Hz, 1H), 7.53 (d, J=8.7 Hz, 1H).

EXAMPLE 91

Preparation of Compound 91: 4-{1-[3-(7-propyl-3-trifluoromethyl-benzo[d]isoxazol-6-yloxy)-propyl]-1H-indol-5-yloxy}-butyric acid Compound 91 is prepared in a manner similar to that described in Example 1.

EXAMPLE 92

Preparation of Compound 92: 2-{1-[3-(7-propyl-3-trifluoromethyl-benzo[d]isoxazol-6-yloxy)-propyl]-1H-indol-5-yloxy}-propionic acid Compound 92 is prepared in a manner similar to that described in Example 1.

EXAMPLE 93

Preparation of Compound 93: 2-{5-[3-(7-propyl-3-trifluoromethyl-benzo[d]isoxazol-6-yloxy)-propoxy]-indol-1-yl}-propionic acid Compound 93 is prepared in a manner similar to that described in Example 2.

EXAMPLE 94

Preparation of Compound 94: {1-[3-(3-phenyl-7-propyl-1H-indol-6-yloxy)-propyl]-1H-indol-5-yloxy}-acetic acid Compound 94 is prepared in a manner similar to that described in Example 1.

EXAMPLE 95

Preparation of Compound 95: {1-[3-(7-propyl-3-trifluoromethyl-1H-indol-6-yloxy)-propyl]-1H-indol-5-yloxy}-acetic acid Compound 95 is prepared in a manner similar to that described in Example 1.

EXAMPLE 96

Preparation of Compound 96: (1-{3-[7-propyl-3-(2,2,2-trifluoro-acetyl)-1H-indol-6-yloxy]-propyl}-1H-indol-5-yloxy)-acetic acid Compound 96 is prepared in a manner similar to that described in Example 1.

EXAMPLE 97

Preparation of Compound 97: {1-[3-(6-benzoyl-1-propyl-naphthalen-2-yloxy)-propyl]-1H-indol-4-yloxy}-acetic acid Compound 97 was prepared in a manner similar to that described in Example 1.
$^1$H NMR (ppm): CDCl$_3$ δ 1.02 (t, J=7.5 Hz, 3H ), 1.59-1.71 (m, 2H), 2.26 (p, 2H), 3.08 (t, J=7.5 Hz, 2H), 3.94 (t, J=5.4 Hz, 2H), 4.33 (t, J=6.6 Hz, 2H), 4.66 (s, 2H), 6.34-6.37 (m, 1H), 6.55 (d, J=3.0 Hz, 1H), 6.93-6.99 (m, 3H), 7.07 (d, J=9.0 Hz, 1H), 7.39-7.44 (m, 2H), 7.50-7.55 (m, 1H), 7.65 (d, J=9.0 Hz, 1H), 7.74-7.77 (m, 2H), 7.87 (dd, J=1.5, 9.0 Hz, 1H), 7.97 (d, J=9.0 Hz, 1H) 8.12 (d, J=1.5 Hz, 1H).

EXAMPLE 98

Preparation of Compound 98: {1-[2-methyl-3-(7-propyl-3-trifluoromethyl-benzo[d]isoxazol-6-yloxy)-propyl]-1H-indol-5-yloxy}-acetic acid Compound 98 is prepared in a manner similar to that described in Example 1.

EXAMPLE 99

Preparation of Compound 99: {6-methoxy-1-[3-(7-propyl-3-trifluoromethyl-benzo[d]isoxazol-6-yloxy)-propyl]-1H-indol-5-yloxy}-acetic acid Compound 99 is prepared in a manner similar to that described in Example 1.

EXAMPLE 100

Preparation of Compound 100: {6-methoxy-5-[3-(7-propyl-3-trifluoromethyl-benzo[d]isoxazol-6-yloxy)-propoxy]-indol-1-yl}-acetic acid Compound 100 is prepared in a manner similar to that described in Example 2.

EXAMPLE 101

Preparation of Compound 101: C-[1-[3-(7-propyl-3-trifluoromethyl-benzo[d]isoxazol-6-yloxy)-propyl]-4-(1H-tetrazol-5-ylmethoxy)-1H-indol-3-yl]-methylamine Compound 101 is prepared in a manner similar to that described in Example 1.

EXAMPLE 102

Preparation of Compound 102: 6-{3-[3-morpholin-4-ylmethyl-4-(1H-tetrazol-5-ylmethoxy)-indol-1-yl]-propoxy}-7-propyl-3-trifluoromethyl-benzo[d]isoxazole Compound 102 is prepared in a manner similar to that described in Example 1.

EXAMPLE 103

Preparation of Compound 103: 6-{3-[3-piperazin-1-ylmethyl-4-(1H-tetrazol-5-ylmethoxy)-indol-1-yl]-propoxy}-7-propyl-3-trifluoromethyl-benzo[d]isoxazole Compound 103 is prepared in a manner similar to that described in Example 1.

EXAMPLE 104

Preparation of Compound 104: {1-[3-(7-propyl-3-trifluoromethyl-benzo[d]isoxazol-6-yloxy)-propyl]-1H-indol-5-yl}-acetic acid Compound 104 is prepared in a manner similar to that described in Example 1.

EXAMPLE 105

Preparation of Compound 105: {1-[3-(7-propyl-3-trifluoromethyl-benzo[d]isoxazol-6-yloxy)-propyl]-1H-indol-6-yl}-acetic acid Compound 105 is prepared in a manner similar to that described in Example 1.

EXAMPLE 106

Preparation of Compound 106: {1-[3-(7-propyl-3-trifluoromethyl-benzo[d]isoxazol-6-yloxy)-propyl]-1H-indol-4-yl}-acetic acid Compound 106 is prepared in a manner similar to that described in Example 1.

EXAMPLE 107

Preparation of Compound 107: {1-[3-(methyl-pyridin-2-yl-amino)-propyl]-1H-indol-4-yloxy}-acetic acid Compound 107 is prepared in a manner similar to that described in Example 1.

EXAMPLE 108

Preparation of Compound 108: {4-[3-(methyl-pyridin-2-yl-amino)-propoxy]-indol-1-yl}-acetic acid Compound 108 is prepared in a manner similar to that described in Example 2.

EXAMPLE 109

Preparation of Compound 109: 5-[3-(7-propyl-3-trifluoromethyl-benzo[d]isoxazol-6-yloxy)-propoxy]-1H-indole-2-carboxylic acid Compound 109 is prepared in a manner similar to that described in Example 2.

EXAMPLE 110

Preparation of Compound 110: {2-methyl-5-[3-(7-propyl-3-trifluoromethyl-benzo[d]isoxazol-6-yloxy)-propoxy]-1H-indol-3-yl}-acetic acid Compound 110 is prepared in a manner similar to that described in Example 2.

EXAMPLE 111

Preparation of Compound 111: 4-{1-[3-(7-propyl-3-trifluoromethyl-benzo[d]isoxazol-6-yloxy)-propyl]-1H-indol-4-yloxy}-butyric acid Compound 111 was prepared in a manner similar to that described in Example 1.

$^1$H NMR (ppm): CDCl$_3$ δ 1.03 (t, J=7.5 Hz, 3H), 1.72-1.82 (m, 2H), 2.20 (p, 2H), 2.34 (p, 2H), 2.65 (t, J=7.2 Hz, 2H), 2.99 (t, J=7.2, 7.8 Hz, 2H), 3.97 (t, J=5.4 Hz, 2H), 4.17 (t, J=6.0 Hz, 2H), 4.37 (t, J=6.3 Hz, 2H), 6.49 (d, J=7.8 Hz, 1H), 6.157 (d, J=3.0 Hz, 1H), 6.89-6.97 (m, 3H), 7.07 (t, J=7.8 Hz, 1H), 7.50 (d, J=9.0 Hz, 1H).

EXAMPLE 112

Preparation of Compound 112: {5-[3-(6-benzoyl-naphthalen-2-yloxy)-propoxy]-indol-1-yl}-acetic acid Compound 112 was prepared in a manner similar to that described in Example 2.

$^1$H NMR (ppm): CDCl$_3$ δ 2.23-2.32 (m, 2H), 4.16 (t, J=6.0 Hz, 2H), 4.26 (t, J=6.0 Hz, 2H), 4.71 (s, 2H), 6.36 (d, J=3.0 Hz, 1H), 6.81 (dd, J=2.1, 9.0 Hz, 1H), 6.99 (d, J=3.0 Hz, 1H), 7.04-7.14 (m, 4H), 7.40-7.43 (m, 2H), 7.49-7.55 (m, 1H), 7.69-7.74 (m, 4H), 7.81 (dd, J=1.8, 9.0 Hz, 1H), 8.09 (d, J=1.5 Hz, 1H).

HRMS-EI (M$^+$): 479.17.

EXAMPLE 113

Preparation of Compound 113: {4-[3-(6-benzoyl-naphthalen-2-yloxy)-propoxy]-indol-1-yl}-acetic acid Compound 113 was prepared in a manner similar to that described in Example 2.

$^1$H NMR (ppm): CDCl$_3$ δ 2.35-2.45 (m, 2H), 4.30-4.40 (m, 4H), 4.78 (s, 2H), 6.54 (d, J=7.8 Hz, 1H), 6.81 (d, J=8.1 Hz, 1H), 6.98 (s, 1H), 7.05-7.12 (m, 1H), 7.15-7.19 (m, 2H), 7.43-7.50 (m, 2H), 7.53-7.57 (m, 1H), 7.68 (d, J=8.4 Hz, 1H), 7.73-7.81 (m, 4H), 7.85 (dd, J=8.5, 1.7 Hz, 1H), 8.13 (d, J=1.2 Hz, 1H).

HRMS-FAB (M$^+$): 479.17.

EXAMPLE 114

Preparation of Compound 114: (1-{3-[4-(4-fluoro-benzoyl)-phenoxy]-propyl}-1H-indol-5-yloxy)-acetic acid Compound 114 is prepared in a manner similar to that described in Example 1.

EXAMPLE 115

Preparation of Compound 115: (6-{3-[4-(4-fluoro-benzoyl)-phenoxy]-propoxy}-indol-1-yl)-acetic acid Compound 115 was prepared in a manner similar to that described in Example 2.
$^1$H NMR (ppm): CDCl$_3$ δ 2.26-2.34 (m, 2H), 4.19 (t, J=6.0 Hz, 2H), 4.31 (t, J=6.0 Hz, 2H), 4.79 (s, 2H), 6.46-6.49 (m, 1H), 6.66 (d, J=2.1 Hz, 1H), 6.80 (dd, J=2.0, 8.6 Hz, 1H), 6.94-6.99 (m, 3H), 7.08-7.16 (m, 2H), 7.48 (d, J=8.4 Hz, 1H), 7.69-7.81 (m, 4H).
HRMS-EI (M$^+$): 447.15.

EXAMPLE 116

Preparation of Compound 116: [6-(3-phenoxazin-10-yl-propoxy)-indol-1-yl]-acetic acid Compound 116 was prepared in a manner similar to that described in Example 2.
$^1$H NMR (ppm): CDCl$_3$+MeOH-d$_4$ δ 2.10-2.19 (m, 2H), 3.78-3.83 (m, 2H), 4.15 (t, J=5.6 Hz, 2H), 4.75 (s, 2H), 6.40 (d, J=3.0 Hz, 1H), 6.54-6.67 (m, 6H), 6.70-6.82 (m, 4H), 7.03 (d, J=3.3 Hz, 1H), 7.44 (d, J=8.1 Hz, 1H).
HRMS-EI (M$^+$): 414.16.

EXAMPLE 117

Preparation of Compound 117: (5-{3-[4-(4-fluoro-benzoyl)-phenoxy]-propoxy}-indol-1-yl)-acetic acid Compound 117 was prepared in a manner similar to that described in Example 2.
$^1$H NMR (ppm): CDCl$_3$ δ 2.30-2.35 (m, 2H), 4.20-4.30 (m, 4H), 4.84 (s, 2H), 6.48 (d, J=3.0 Hz, 1H), 6.89 (dd, J=2.4, 8.7 Hz, 1H), 6.98 (d, J=8.7 Hz, 2H), 7.04 (d, J=3.0 Hz, 1H), 7.11-7.18 (m, 4H), 7.75-7.82 (m, 4H).
HRMS-EI (M$^+$): 447.15.

EXAMPLE 118

Preparation of Compound 118: [5-(3-phenoxazin-10-yl-propoxy)-indol-1-yl]-acetic acid Compound 118 is prepared in a manner similar to that described in Example 2.

EXAMPLE 119

Preparation of Compound 119: {4-[3-(2-benzoyl-4-chloro-phenoxy)-propoxy]-indol-1-yl}-acetic acid Compound 119 was prepared in a manner similar to that described in Example 2.
$^1$H NMR (ppm): CDCl$_3$ δ 2.35-2.42 (m, 2H), 4.05-4.10 (m, 2H), 4.59 (t, J=6.8 Hz, 2H), 4.82 (s, 2H), 6.38 (d, J=7.8 Hz, 1H), 6.87 (d, J=8.4 Hz, 1H), 7.01-7.07 (m, 3H), 7.13-7.20 (m, 2H), 7.30-7.37 (m, 2H), 7.42-7.50 (m, 2H), 8.05 (d, J=7.8 Hz, 2H).
HRMS-EI (M$^+$): 463.12.

EXAMPLE 120

Preparation of Compound 120: [4-(3-carbazol-9-yl-propoxy)-indol-1-yl]-acetic acid Compound 120 was prepared in a manner similar to that described in Example 2.
$^1$H NMR (ppm): CDCl$_3$ δ 1.97-2.03 (m, 2H), 3.74 (t, J=5.9 Hz, 2H), 4.09 (t, J=6.0 Hz, 2H), 4.80 (s, 2H), 6.24 (d, J=7.8 Hz, 1H), 6.85 (d, J=8.4 Hz, 1H), 6.91 (d, J=8.7 Hz, 1H), 6.96 (s, 1H), 7.03-7.09 (m, 2H), 7.27-7.39 (m, 4H), 7.41-7.45 (m, 1H), 7.68-7.73 (m, 2H).
HRMS-EI (M$^+$): 398.16.

EXAMPLE 121

Preparation of Compound 121: [4-(4-phenoxazin-10-yl-butoxy)-indol-1-yl]-acetic acid Compound 121 was prepared in a manner similar to that described in Example 2.
$^1$H NMR (ppm): CDCl$_3$+MeOH-d$_4$ δ 1.82-1.97 (m, 4H), 3.49-3.60 (m, 2H), 4.11-4.16 (m, 2H), 4.74 (s, 2H), 6.41-6.48 (m, 4H), 6.49-6.58 (m, 4H), 6.61-6.69 (m, 2H), 6.82 (d, J=8.1 Hz, 1H), 6.93 (s, 1H), 7.04 (t, J=8.1 Hz, 1H).
HRMS-EI (M$^+$): 428.17.

EXAMPLE 122

Preparation of Compound 122: 1-[3-(7-propyl-3-trifluoromethyl-benzo[d]isoxazol-6-yloxy)-propyl]-1H-indol-4-ol Compound 122 was prepared in a manner similar to that described in Example 1.
$^1$H NMR (ppm): CDCl$_3$ δ 1.02 (t, J=7.2 Hz, 3H), 1.71-1.84 (m, 2H), 2.33 (p, 2H), 2.98 (t, J=7.2 Hz, 2H), 3.97 (t, J=5.7 Hz, 2H), 4.35 (t, J=6.6 Hz, 2H), 4.93 (s, 1H), 6.34 (d, J=3.3 Hz, 1H), 6.75 (dd, J=2.4 Hz, 8.7 Hz, 1H), 6.90 (d, J=8.7 Hz, 1H), 7.00-7.02 (m, 2H), 7.18 (d, J=8.7 Hz, 1H), 7.50 (d, J=8.7 Hz, 1H).

EXAMPLE 123

Preparation of Compound 123: 2-{1-[3-(3-cyano-7-propyl-1H-indol-6-yloxy)-propyl]-1H-indol-4-yloxy}-2-methyl-propionic acid Compound 123 was prepared in a manner similar to that described in Example 1.
$^1$H NMR (ppm): CDCl$_3$ δ 1.02 (t, J=7.2 Hz, 3H), 1.37 (s, 6H), 1.39-1.70 (m, 2H), 2.30 (p, 2H), 2.88 (t, J=7.2 Hz, 2H), 4.00 (t, J=5.7 Hz, 2H), 4.39 (t, J=6.6 Hz, 2H), 6.52 (d, J=3.3 Hz, 1H), 6.60 (d, J=7.5 Hz, 1H), 6.85 (d, J=8.4 Hz, 1H), 7.03-7.14 (m, 3H), 7.49 (d, J=8.7 Hz, 1H), 7.64 (d, J=2.7 Hz, 1H), 8.63 (bs, 1H).

EXAMPLE 124

Preparation of Compound 124: {1-[3-(3-cyano-7-propyl-1H-indol-6-yloxy)-propyl]-1H-indol-5-yloxy}-acetic acid Compound 124 was prepared in a manner similar to that described in Example 1.

$^1$H NMR (ppm): CDCl$_3$ δ 0.93 (t, J=7.2 Hz, 3H), 1.36-1.63 (m, 2H), 2.20 (p, 2H), 2.82 (t, J=7.2 Hz, 2H), 3.80 (t, J=5.7 Hz, 2H), 4.22 (t, J=6.6 Hz, 2H), 4.40 (s, 2H), 6.43 (d, J=3.3 Hz, 1H), 6.54 (d, J=7.5 Hz, 1H), 6.81 (d, J=8.4 Hz, 1H), 7.00-7.18 (m, 3H), 7.41 (d, J=8.7 Hz, 1H), 7.55 (d, J=2.7 Hz, 1H), 8.23 (bs, 1H).

EXAMPLE 125

Preparation of Compound 125: {4-[3-(3-phenyl-7-propyl-benzo[d]isoxazol-6-yloxy)-propoxy]-indol-1-yl}-acetic acid Compound 125 was prepared in a manner similar to that described in Example 2.

$^1$H NMR (ppm): CDCl$_3$ δ 0.968 (t, J=4.8 Hz, 3H), 1.710-1.771 (m, 2H), 2.415-2.450 (m, 2H), 2.934 (t, J=7.2 Hz, 2H), 4.335 (q, J=4.8 Hz, 4H), 4.880 (s, 2H), 6.595 (d, J=7.6 Hz, 1H), 6.682 (d, J=2.8 Hz, 1H), 6.878 (d, J=8.8 Hz, 1H), 6.986 (d, J=2.8 Hz, 1H), 7.029 (d, J=8.8 Hz, 1H), 7.155 (t, J=8.0 Hz, 2H), 7.508-7.556 (m, 2H), 7.648 (d, J=8.8 Hz, 1H), 7.933 (dd, J=1.2, 7.2 Hz, 2H).

EXAMPLE 126

Preparation of Compound 126: {5-[3-(3-cyano-7-propyl-1H-indol-6-yloxy)-propoxy]-indol-1-yl}-acetic acid Compound 126 was prepared in a manner similar to that described in Example 2.

$^1$H NMR (ppm): CDCl$_3$ δ 0.95 (t, J=7.5 Hz, 3H), 1.36-1.51 (m, 2H), 2.40 (p, 2H), 2.73 (t, J=7.5 Hz, 2H), 4.14-4.18 (m, 4H), 4.89 (s, 2H), 6.37-6.38 (m, 1H), 6.80 (dd, J=2.4, 8.7 Hz, 1H), 6.93 (d, J=8.7 Hz, 1H), 7.04 (d, J=2.4 Hz, 1H), 7.09 (t, J=2.7 Hz, 1H), 7.19 (d, J=8.7 Hz, 1H), 7.29 (s, 1H), 7.43 (d, J=8.7 Hz, 1H), 8.02 (s, 1H).

EXAMPLE 127

Preparation of Compound 127: {4-[2-methyl-3-(7-propyl-3-trifluoromethyl-benzo[d]isoxazol-6-yloxy)-propoxy]-indol-1-yl}-acetic acid Compound 127 was prepared in a manner similar to that described in Example 2.

$^1$H NMR (ppm): CDCl$_3$ δ 0.87 (t, J=7.5 Hz, 3H), 1.28 (d, J=10.2 Hz, 3H), 1.55-1.67 (m, 2H), 2.52-2.58 (m, 1H), 2.83 (t, J=7.5 Hz, 2H), 4.07-4.20 (m, 4H), 4.77 (s, 2H), 6.48 (d, J=7.5 Hz, 1H), 6.57 (d, J=3.0 Hz, 1H), 6.77 (d, J=8.7 Hz, 1H), 6.88 (d, J=3.0 Hz, 1H), 6.99-7.08 (m, 2H), 7.44 (d, J=8.7 Hz, 1H).

EXAMPLE 128

Preparation of Compound 128: 2-{4-[3-(7-propyl-3-trifluoromethyl-benzo[d]isoxazol-6-yloxy)-propoxy]-indol-1-yl}-butyric acid Compound 128 was prepared in a manner similar to that described in Example 2.

$^1$H NMR (ppm): CDCl$_3$ δ 0.81-0.88 (m, 6H), 1.54-1.66 (m, 2H), 2.08-2.26 (m, 2H), 2.33 (p, 2H), 2.82 (t, J=7.5 Hz, 2H), 4.24-4.29 (m, 4H), 4.78 (dd, J=6.0, 9.9 Hz, 1H), 6.47 (d, J=7.5 Hz, 1H), 6.59 (d, J=3.0 Hz, 1H), 6.88 (d, J=6.6 Hz, 1H), 6.99-7.05 (m, 3H), 7.44 (d, J=8.7 Hz, 1H).

EXAMPLE 129

Preparation of Compound 129: {6-[3-(6-benzoyl-naphthalen-2-yloxy)-propoxy]-indol-1-yl}-acetic acid Compound 129 was prepared in a manner similar to that described in Example 2.

$^1$H NMR (ppm): CDCl$_3$+MeOH-d$_4$ δ 2.34-2.42 (m, 2H), 4.23-4.32 (m, 2H), 4.33-4.40 (m, 2H), 4.78 (s, 2H), 6.44 (s, 1H), 6.76-6.83 (m, 2H), 7.01 (s, 1H), 7.18-7.28 (m, 2H), 7.42-7.55 (m, 5H), 7.60-7.70 (m, 1H), 7.81 (d, J=8.1 Hz, 2H), 7.85-7.91 (m, 1H), 8.18 (s, 1H).

HRMS-EI (M$^+$): 479.17.

EXAMPLE 130

Preparation of Compound 130: 3-{4-[3-(7-propyl-3-trifluoromethyl-benzo[d]isoxazol-6-yloxy)-propoxy]-indol-1-yl}-propionic acid Compound 130 was prepared in a manner similar to that described in Example 2.

$^1$H NMR (ppm): CDCl$_3$ δ 0.86 (t, J=7.5 Hz, 3H), 1.54-1.64 (m, 2H), 2.33 (p, 2H), 2.74 (t, J=6.9 Hz, 2H), 2.82 (t, J=7.5 Hz, 2H), 4.25-4.35 (m, 6H), 6.45-6.48 (m, 2H), 6.89 (d, J=8.7 Hz, 1H), 6.96 (t, J=1.5 Hz, 1H), 6.99-7.07 (m, 2H), 7.45 (d, J=8.7 Hz, 1H).

EXAMPLE 131

Preparation of Compound 131: {6-[3-(6-benzoyl-1-propyl-naphthalen-2-yloxy)-propoxy]-indol-1-yl}-acetic acid Compound 131 was prepared in a manner similar to that described in Example 2.

$^1$H NMR (ppm): CDCl$_3$+MeOH-d$_4$ δ 1.01 (t, J=7.4 Hz, 3H), 1.60-1.72 (m, 2H), 2.29-2.37 (m, 2H), 3.03-3.16 (m, 2H), 4.23 (t, J=6.0 Hz, 2H), 4.32 (t, J=6.0 Hz, 2H), 4.65 (s, 2H), 6.41 (d, J=3.0 Hz, 1H), 6.74-6.80 (m, 2H), 6.95 (d, J=3.0 Hz, 1H), 7.40-7.54 (m, 4H), 7.58-7.63 (m, 1H), 7.76 (d, J=9.0 Hz, 1H), 7.80-7.84 (m, 2H), 7.91 (dd, J=1.8, 9.0 Hz, 1H), 8.02 (d, J=9.0 Hz, 1H), 8.19 (d, J=1.5 Hz, 1H).

HRMS-FAB (M$^+$): 521.22.

EXAMPLE 132

Preparation of Compound 132: (6-{3-[4-(4-fluoro-benzoyl)-2-propyl-phenoxy]-propoxy}-indol-1-yl)-acetic acid Compound 132 was prepared in a manner similar to that described in Example 2.

$^1$H NMR (ppm): CDCl$_3$+MeOH-d$_4$ δ 0.93 (t, J=7.4 Hz, 3H), 1.55-1.65 (m, 2H), 2.29-2.35 (m, 2H), 2.58-2.65 (m, 2H), 4.15-4.27 (m, 4H), 4.65 (s, 2H), 6.41 (d, J=3.0 Hz, 1H), 6.72-6.78 (m, 2H), 6.90 (d, J=9.0 Hz, 1H), 6.96 (d, J=3.0 Hz, 1H), 7.14 (t, J=8.7 Hz, 2H), 7.45 (d, J=9.3 Hz, 1H), 7.58-7.62 (m, 2H), 7.73-7.80 (m, 2H).

HRMS-EI (M$^+$): 489.2.

EXAMPLE 133

Preparation of Compound 133: (5-{3-[7-propyl-3-(2,2,2-trifluoro-acetyl)-1H-indol-6-yloxy]-propoxy}-indol-1-yl)-acetic acid Compound 133 was prepared in a manner similar to that described in Example 2.

$^1$H NMR (ppm): CDCl$_3$ δ 1.00 (t, J=7.5 Hz, 3H), 1.56-1.64 (m, 2H), 2.25 (p, 2H), 3.01 (t, J=7.8 Hz, 2H), 3.95 (t, J=5.4 Hz, 2H), 4.52 (t, J=5.4 Hz, 2H), 4.68 (s, 2H), 6.39 (m, 1H), 6.79 (dd, J=2.1, 8.7 Hz, 1H), 6.85 (d, J=8.7 Hz, 1H), 7.00 (m, 1H), 7.13 (m, 1H), 7.23 (d, J=8.7 Hz, 1H), 7.82 (s, 1H), 8.05 (bs, 1H), 8.17 (d, J=8.7 Hz, 1H).

EXAMPLE 134

Preparation of Compound 134: {1-[3-(2-phenyl-7-propyl-benzofuran-6-yloxy)-propyl]-1H-indol-4-yloxy}-acetic acid Compound 134 was prepared in a manner similar to that described in Example 1.

$^1$H NMR (ppm): CDCl$_3$ δ 1.044 (t, J=7.2 Hz, 3H), 1.784-1.839 (m, 2H), 2.284-2.313 (m, 2H), 3.009 (t, J=7.6 Hz, 2H), 3.938 (t, J=5.6 Hz, 2H), 4.389 (t, J=6.8 Hz, 2H), 4.803 (s, 2H), 6.446 (dd, J=2.8, 5.6 Hz, 1H), 6.607 (d, J=3.2 Hz, 1H), 6.727 (d, J=8.4 Hz, 1H), 6.925 (s, 1H), 7.026-7.088 (m, 3H), 7.251-7.323 (m, 2H), 7.422 (t, J=8.0 Hz, 2H), 7.821 (dd, J=1.2, 8.4 Hz, 2H).

EXAMPLE 135

Preparation of Compound 135: 2-methyl-2-{1-[3-(2-phenyl-7-propyl-benzofuran-6-yloxy)-propyl]-1H-indol-4-yloxy}-propionic acid Compound 135 was prepared in a manner similar to that described in Example 1.

$^1$H NMR (ppm): CDCl$_3$ δ 1.100 (t, J=7.2 Hz, 3H), 1.705 (s, 6H), 1.835-1.899 (m, 2H), 2.297-2.343 (m, 2H), 3.064 (t, J=7.2 Hz, 2H), 3.954 (t, J=5.6Hz, 2H), 4.388 (t, J=6.4 Hz, 2H), 6.591-6.619 (m, 2H), 6.755 (d, J=8.8 Hz, 1H), 6.952 (s, 1H), 7.027-7.142 (m, 3H), 7.294-7.356 (m, 2H), 7.455 (t, J=8.0 Hz, 2H), 7.862 (d, J=7.2 Hz, 2H).

EXAMPLE 136

Preparation of Compound 136: 1-[3-(3-phenyl-7-propyl-benzo[d]isoxazol-6-yloxy)-propyl]-1H-indol-4-ol Compound 136 was prepared in a manner similar to that described in Example 1.

$^1$H NMR (ppm): CDCl$_3$ δ 1.053 (t, J=5.2 Hz, 3H), 1.627-1.709 (m, 2H), 2.295 (quintet, J=4.0, 8.0 Hz, 2H), 2.791 (quintet, J=4.0, 4.8 Hz, 2H), 3.913 (t, J=3.6 Hz, 2H), 4.342 (t, J=4.4 Hz, 2H), 6.261 (d, J=6.0 Hz, 1H), 6.503 (d, J=4.8 Hz, 1H), 6.547 (dd, J=0.4, 2.0 Hz, H), 6.934 (d, J=5.6 Hz, 1H), 6.960 (d, J=2.4 Hz, 1H), 7.038 (t, J=5.6 Hz, 1H), 7.384 (d, J=5.6 Hz, 1H), 7.450-7.475 (m, 2H), 7.524-7.537 (m, 1H), 7.606-7.621 (m, 2H).

EXAMPLE 137

Preparation of Compound 137: {4-[3-(6-benzoyl-1-propyl-naphthalen-2-yloxy)-propoxy]-indol-1-yl}-acetic acid Compound 137 was prepared in a manner similar to that described in Example 2.

$^1$H NMR (ppm): CDCl$_3$+MeOH-d$_4$ δ 1.01 (t, J=7.4 Hz, 3H), 1.60-1.71 (m, 2H), 2.38-2.45 (m, 2H), 3.03-3.11 (m, 2H), 4.35-4.41 (m, 4H), 4.74 (s, 2H), 6.55 (d, J=7.8 Hz, 1H), 6.62 (d, J=3.0 Hz, 1H), 6.87 (d, J=8.1 Hz, 1H), 6.97 (d, J=3.3 Hz, 1H), 7.05-7.13 (m, 1H), 7.30-7.36 (m, 1H), 7.46-7.53 (m, 2H), 7.56-7.64 (m, 1H), 7.75 (d, J=9.0 Hz, 1H), 7.79-7.85 (m, 2H), 7.91 (dd, J=1.8, 9.0 Hz, 1H), 8.01 (d, J=9.0 Hz, 1H), 8.19 (d, J=1.5 Hz, 1H).

HRMS-FAB (M$^+$): 521.22.

EXAMPLE 138

Preparation of Compound 138: (4-{3-[4-(4-fluoro-benzoyl)-2-propyl-phenoxy]-propoxy}-indol-1-yl)-acetic acid Compound 138 was prepared in a manner similar to that described in Example 2.

$^1$H NMR (ppm): CDCl$_3$+MeOH-d$_4$ δ 0.92 (t, J=7.4 Hz, 3H), 1.50-1.65 (m, 2H), 2.30-2.38 (m, 2H), 2.57-2.64 (m, 2H), 4.22-4.29 (m, 4H), 4.56 (s, 2H), 6.46 (d, J=7.5 Hz, 1H), 6.55 (d, J=3.0 Hz, 1H), 6.80 (d, J=8.1 Hz, 1H), 6.84-6.90 (m, 2H), 6.98-7.03 (m, 1H), 7.07-7.15 (m, 2H), 7.57-7.61 (m, 2H), 7.71-7.78 (m, 2H).

HRMS-EI (M$^+$): 489.20.

EXAMPLE 139

Preparation of Compound 139: {5-[3-(6-benzoyl-1-propyl-naphthalen-2-yloxy)-propoxy]-indol-1-yl}-acetic acid Compound 139 was prepared in a manner similar to that described in Example 2.

$^1$H NMR (ppm): CDCl$_3$ δ 1.01 (t, J=7.4 Hz, 3H), 1.61-1.70 (m, 2H), 2.32-2.38 (m, 2H), 3.07 (t, J=7.8 Hz, 2H), 4.25 (t, J=6.0 Hz, 2H), 4.33 (t, J=6.0 Hz, 2H), 4.80 (s, 2H), 6.45 (d, J=3.0 Hz, 1H), 6.87 (dd, J=2.1, 9.0 Hz, 1H), 7.01 (d, J=3.0 Hz, 1H), 7.08-7.12 (m, 2H), 7.31 (d, J=9.0 Hz, 1H), 7.45-7.51 (m, 2H), 7.56-7.61 (m, 1H), 7.74 (d, J=9.0 Hz, 1H), 7.81-7.83 (m, 2H), 7.91 (dd, J=1.8, 9.0 Hz, 1H), 8.01 (d, J=9.0 Hz, 1H), 8.19 (d, J=1.5 Hz, 1H).

HRMS-FAB (M$^+$): 521.22.

EXAMPLE 140

Preparation of Compound 140: (5-{3-[4-(4-fluoro-benzoyl)-2-propyl-phenoxy]-propoxy}-indol-1-yl)-acetic acid Compound 140 was prepared in a manner similar to that described in Example 2.
$^1$H NMR (ppm): CDCl$_3$+MeOH-d$_4$ δ 0.92 (t, J=7.2 Hz, 3H), 1.54-1.65 (m, 2H), 2.26-2.34 (m, 2H), 2.60-2.65 (m, 2H), 4.16 (d, J=5.9 Hz, 2H), 4.24 (d, J=5.9 Hz, 2H), 4.60 (s, 2H), 6.36 (d, J=2.4 Hz, 1H), 6.80 (d, J=8.7 Hz, 1H), 6.88 (d, J=9.0 Hz, 1H), 6.96 (d, J=2.1 Hz, 1H), 7.03-7.16 (m, 4H), 7.57-7.63 (m, 2H), 7.72-7.79 (m, 2H)
HRMS-EI (M$^+$): 489.20.

EXAMPLE 141

Preparation of Compound 141: 2-(1-{3-[4-(4-fluoro-benzoyl)-2-propyl-phenoxy]-propyl}-1H-indol-4-yloxy)-2-methyl-propionic acid Compound 141 was prepared in a manner similar to that described in Example 1.
$^1$H NMR (ppm): CDCl$_3$ δ 1.03 (t, J=7.5 Hz, 3H), 1.68 (s, 6H), 1.71-1.76 (m, 2H), 2.34-2.38 (m, 2H), 2.73 (t, J=7.5 Hz, 2H), 3.98 (t, J=5.4 Hz, 2H), 4.39 (t, J=6.6 Hz, 2H), 6.54 (d, J=3 Hz, 1H), 6.61 (dd, J=1.2, 6.9 Hz, 1H), 6.76 (d, J=8.4 Hz, 1H), 7.02 (d, J=3 Hz, 1H), 7.08-718 (m, 5H), 7.59 (dd, J=2.1, 8.7 Hz, 1H), 7.68 (d, J=2.1 Hz, 1H), 7.77-7.82 (m, 2H).
HRMS-EI (M$^+$): 517.23.

EXAMPLE 142

Preparation of Compound 142: 2-(1-{3-[4-(4-fluoro-benzoyl)-2-propyl-phenoxy]-propyl}-1H-indol-5-yloxy)-2-methyl-propionic acid Compound 142 was prepared in a manner similar to that described in Example 1.
$^1$H NMR (ppm): CDCl$_3$ δ 1.03 (t, J=7.5 Hz, 3H), 1.58 (s, 6H), 1.68-1.76 (m, 2H), 2.34-2.37 (m, 2H), 2.73 (t, J=7.8 Hz, 2H), 3.97 (t, J=5.4 Hz, 2H), 4.39 (t, J=6.3 Hz, 2H), 6.44 (d, J=3 Hz, 1H), 6.61 (dd, J=1.2, 6.9 Hz, 1H), 6.74 (d, J=9.3 Hz, 1H), 6.84 (dd, J=2.4, 8.9 Hz, 1H), 7.08 (d, J=3 Hz, 1H), 7.13-7.23 (m, 5H), 7.59 (dd, J=2.4, 8.9 Hz, 1H), 7.67 (d, J=2.4 Hz, 1H), 7.78-7.83 (m, 2H).
HRMS-EI (M$^+$): 517.23.

EXAMPLE 143

Preparation of Compound 143: 2-(1-{3-[4-(4-fluoro-benzoyl)-2-propyl-phenoxy]-propyl}-1H-indol-6-yloxy)-2-methyl-propionic acid Compound 143 was prepared in a manner similar to that described in Example 1.
$^1$H NMR (ppm): CDCl$_3$ δ 1.02 (t, J=7.5 Hz, 3H), 1.56 (s, 6H), 1.67-1.75 (m, 2H), 2.30-2.34 (m, 2H), 2.72 (t, J=7.2 Hz, 2H), 3.95 (t, J=5.4 Hz, 2H), 4.33 (t, J=6.3 Hz, 2H), 6.45 (d, J=3 Hz, 1H), 6.75 (d, J=8.7 Hz, 1H), 6.61 (dd, J=1.8, 8.7 Hz, 1H), 6.97 (s, 1H), 7.03 (d, J=3 Hz, 1H), 7.15 (t, J=8.4 Hz, 2H), 7.5 (d, J=8.4 Hz, 1H), 7.59 (dd, J=2.1, 8.4 Hz, 1H), 7.67 (d, J=2.1 Hz, 1H), 7.77-7.82 (m, 2H).
HRMS-EI (M$^+$): 517.22.

EXAMPLE 144

Preparation of Compound 144: {4-[3-(3-phenyl-7-propyl-benzofuran-6-yloxy)-propoxy]-indol-1-yl}-acetic acid Compound 144 was prepared in a manner similar to that described in Example 2.
$^1$H NMR (ppm): CDCl$_3$ δ 0.952 (t, J=7.2 Hz, 3H), 1.674-1.712 (m, 2H), 2.366-2.395 (m, 2H), 2.885-2.910 (m, 2H), 4.273 (t, J=6.0 Hz, 2H), 4.352 (t, J=6.0 Hz, 2H), 4.830 (s, 2H), 6.581 (d, J=7.8 Hz, 1H), 6.670 (dd, J=0.6, 3.0 Hz, 1H), 6.845 (d, J=8.4 Hz, 1H), 6.941 (d, J=2.4 Hz, 1H), 6.950 (d, J=3.0 Hz, 1H), 7.130 (t, J=8.4 Hz, 1H), 7.320-7.347 (m, 1H), 7.427-7.455 (m, 2H), 7.547 (d, J=8.4 Hz, 1H), 7.608-7.624 (m, 2H), 7.696 (s, 1H).

EXAMPLE 145

Preparation of Compound 145: {4-[3-(2-phenyl-7-propyl-benzofuran-6-yloxy)-propoxy]-indol-1-yl}-acetic acid Compound 145 was prepared in a manner similar to that described in Example 2.
$^1$H NMR (ppm): CDCl$_3$ δ 0.960 (t, J=7.2 Hz, 3H), 1.705-1.793 (m, 2H), 2.372 (t, J=6.4 Hz, 2H), 2.931 (t, J=7.2 Hz, 2H), 4.258 (t, J=6.0 Hz, 2H), 4.354 (t, J=6.0 Hz, 2H), 6.585 (d, J=8.0 Hz, 1H), 6.678 (d, J=3.6 Hz, 1H), 6.863 (dd, J=5.2, 8.0 Hz, 1H), 6.914 (s, 1H), 6.972 (d, J=3.6 Hz, 1H), 7.117-7.332 (m, 4H), 7.408 (t, J=8.0 Hz, 2H), 7.806 (d, J=7.2 Hz, 2H).

EXAMPLE 146

Preparation of Compound 146: 2-methyl-2-{1-[3-(3-phenyl-7-propyl-benzofuran-6-yloxy)-propyl]-1H-indol-4-yloxy}-propionic acid Compound 146 was prepared in a manner similar to that described in Example 1.
$^1$H NMR (ppm): CDCl$_3$ δ 1.050 (t, J=7.2 Hz, 3H), 1.760-1.816 (m, 2H), 2.302-2.332 (m, 2H), 2.986 (t, J=7.6 Hz, 2H), 3.967 (t, J=6.0 Hz, 2H), 4.387 (t, J=6.8 Hz, 2H), 6.543 (d, J=3.2 Hz, 1H), 6.575 (d, J=7.2 Hz, 1H), 6.814 (d, J=8.4 Hz, 1H), 7.029 (d, J=3.2 Hz, 1H), 7.069 (s, 1H), 7.108 (t, J=8.0 Hz, 1H), 7.355 (d, J=7.6 Hz, 1H), 7.452 (t, J=8.0 Hz, 2H), 7.542 (d, J=8.8 Hz, 1H), 7.614-7.635 (m, 2H), 7.727 (s, 1H).

EXAMPLE 147

Preparation of Compound 147: {1-[3-(3-phenyl-7-propyl-benzofuran-6-yloxy)-propyl]-1H-indol-4-yloxy}-acetic acid Compound 147 was prepared in a manner similar to that described in Example 1.
$^1$H NMR (ppm): CDCl$_3$ δ 1.051 (t, J=7.2 Hz, 3H), 1.847-1.872 (m, 2H), 2.294-2.324 (m, 2H), 3.000 (t, J=7.2 Hz, 2H), 3.962 (t, J=5.6 Hz, 2H), 4.389 (t, J=6.8 Hz, 2H), 4.807 (s, 2H), 6.448 (d, J=8.0 Hz, 2H), 6.816 (d, J=8.4 Hz, 1H), 7.016-7.112 (m, 3H), 7.351 (d, J=7.6 Hz, 1H), 7.457 (t, J=8.0 Hz, 2H), 7.545 (d, J=8.0 Hz, 1H), 7.622-7.643 (m, 2H), 7.734 (s, 1H).

EXAMPLE 148

Preparation of Compound 148: {1-[3-(3-phenyl-7-propyl-benzo[d]isoxazol-6-yloxy)-propyl]-1H-indol-4-yloxy}-acetic acid Compound 148 was prepared in a manner similar to that described in Example 1.

$^1$H NMR (ppm): CDCl$_3$ δ 1.024 (t, J=7.2 Hz, 3H), 1.776-1.811 (m, 2H), 2.155 (brm 2H), 2.992 (t, J=7.2 Hz, 2H), 3.955 (t, J=6.0 Hz, 2H), 4.365 (t, J=6.4 Hz, 2H), 4.899 (s, 2H), 6.418 (d, J=7.2 Hz 2H), 6.611 (d, J=3.2 Hz, 1H), 6.815 (d, J=8.8 Hz, 1H), 6.989-7.037 (m, 3H), 7.493-7.526 (m, 3H), 7.594 (d, J=6.6 Hz, 1H), 7.906 (d, J=6.6 Hz, 1H).

EXAMPLE 149

Preparation of Compound 149: 2-{1-[3-(6-benzoyl-1-propyl-naphthalen-2-yloxy)-propyl]-1H-indol-4-yloxy}-2-methyl-propionic acid Compound 149 was prepared in a manner similar to that described in Example 1.

$^1$H NMR (ppm): CDCl$_3$ δ 1.12 (t, J=7.5 Hz, 3H), 1.67 (s, 6H), 1.71-1.80 (m, 2H), 2.36-2.40 (m, 2H), 3.18 (t, J=7.5 Hz, 2H), 4.07 (t, J=5.4 Hz, 2H), 4.44 (t, J=6.6 Hz, 2H), 6.54 (d, J=3 Hz, 1H), 6.61 (dd, J=0.6, 7.5 Hz, 1H), 7.05 (d, J=3 Hz, 1H), 7.07-7.20 (m, 4H), 7.49-7.62 (m, 4H), 7.61 (d, J=8.7 Hz, 1H), 7.88-7.84 (m, 2H), 7.97 (dd, J=1.8, 9 Hz, 1H), 8.07 (d, J=9 Hz, 1H), 8.22 (d, J=1.8 Hz, 1H).

HRMS-EI (M$^+$): 549.25.

EXAMPLE 150

Preparation of Compound 150: 2-{1-[3-(6-benzoyl-1-propyl-naphthalen-2-yloxy)-propyl]-1H-indol-5-yloxy}-2-methyl-propionic acid Compound 150 was prepared in a manner similar to that described in Example 1.

$^1$H NMR (ppm): CDCl$_3$ δ 1.12 (t, J=7.2 Hz, 3H), 1.57 (s, 6H), 1.73-1.81 (m, 2H), 2.18-2.40 (m, 2H), 3.16-3.21 (m, 2H), 4.08 (t, J=5.7 Hz, 2H), 4.44 (t, J=6.6 Hz, 2H), 2H), 6.44 (d, J=2.7 Hz, 1H), 6.86 (dd, J=2.4, 8.4 Hz, 1H), 7.12 (d, J=2.7 Hz, 1H), 7.17-7.28 (m, 5H), 749-7.54 (m, 2H), 7.59-7.62 (m, 1H), 7.76 (d, J=9.0 Hz, 1H), 7.86 (d, J=9.0 Hz, 2H), 7.97 (dd, J=1.8, 8.7 nHz, 1H), 8.07 (d, J=9 Hz, 1H), 8.21 (d, J=1.8 Hz, 1H).

HRMS-EI (M$^+$): 549.25.

EXAMPLE 151

Preparation of Compound 151: 2-{1-[3-(6-benzoyl-1-propyl-naphthalen-2-yloxy)-propyl]-1H-indol-6-yloxy}-2-methyl-propionic acid Compound 151 was prepared in a manner similar to that described in Example 1.

$^1$H NMR (ppm): CDCl$_3$ δ 1.11 (t, J=7.5 Hz, 3H), 1.53 (s, 6H), 1.53-1.77 (m, 2H), 2.33-2.37 (m, 2H), 3.18 (t, J=7.5 Hz, 2H), 4.05 (t, J=5.7 Hz, 2H), 4.39 (t, J=6.3 Hz, 2H), 6.46 (d, J=2.4 Hz, 1H), 6.79 (dd, J=2.1, 8.4 Hz, 1H), 6.99 (d, J=2.4 Hz, 1H), 7.08 (d, J=3.0 Hz, 1H), 7.17 (d, J=8.7 Hz, 1H), 7.54-7.49 (m, 3H), 7.62-7.59 (m, 1H), 7.75 (d, J=9 Hz, 1H), 7.85 (dd, J=1.2, 8.3 Hz, 2H), 7.97 (dd, J=1.8, 8.7 Hz, 1H), 8.07 (d, J=9 Hz, 1H), 8.21 (d, J=1.8 Hz, 1H).

HRMS-EI (M$^+$): 549.25.

EXAMPLE 152

Preparation of Compound 152: {5-[3-(7-propyl-1H-indol-6-yloxy)-propoxy]-indol-1-yl}-acetic acid Compound 152 was prepared in a manner similar to that described in Example 2.

$^1$H NMR (ppm): CDCl$_3$ δ 0.89 (t, J=7.5 Hz, 3H), 1.55-1.62 (m, 2H), 2.21 (p, 2H), 2.73 (t, J=7.5 Hz, 2H), 4.08-4.19 (m, 4H), 4.76 (s, 2H), 6.39 (d, J=3.0 Hz, 1H), 6.78 (d, J=8.7 Hz, 1H), 6.82 (dd, J=2.4, 9.0 Hz, 1H), 6.95 (d, J=3.0 Hz, 1H), 7.03-7.05 (m, 3H), 7.32 (d, J=8.7 Hz, 1H), 7.87 (bs, 1H).

EXAMPLE 153

Preparation of Compound 153: 2-(1-{3-[2-(4-fluoro-benzoyl)-7-propyl-1H-indol-6-yloxy]-propyl}-1H-indol-4-yloxy)-2-methyl-propionic acid Compound 153 was prepared in a manner similar to that described in Example 1.

$^1$H NMR (ppm): CDCl$_3$ δ 1.09 (t, J=7.5 Hz, 3H), 1.69 (s, 6H), 1.72-1.82 (m, 2H), 2.35 (p, 2H), 2.94 (t, J=7.5 Hz, 2H), 4.02 (t, J=5.7 Hz, 2H), 4.42 (t, J=6.6 Hz, 2H), 6.55 (dd, J=0.6, 3.3 Hz, 1H), 6.63 (dd, J=0.6, 7.5 Hz, 1H), 6.80 (d, J=8.7 Hz, 1H), 7.06-7.25 (m, 6H), 7.49 (d, J=8.7 Hz, 1H), 7.98-8.03 (m, 2H), 9.18 (bs, 1H).

EXAMPLE 154

Preparation of Compound 154: 2-(1-{3-[3-(4-fluoro-benzoyl)-1,7-dipropyl-1H-indol-6-yloxy]-propyl}-1H-indol-4-yloxy)-2-methyl-propionic acid Compound 154 was prepared in a manner similar to that described in Example 1.

$^1$H NMR (ppm): CDCl$_3$ δ 1.01 (t, J=7.5 Hz, 3H), 1.12 (t, J=7.5Hz, 3H), 1.69 (s, 6H), 1.60-1.75 (m, 2H), 1.83-1.95 (m, 2H), 2.36 (p, 2H), 3.00 (t, J=7.5 Hz, 2H), 4.04 (t, J=5.7 Hz, 2H), 4.21 (t, J=6.9 Hz, 2H), 4.42 (t, J=6.6 Hz, 2H), 6.55 (d, J=2.7 Hz, 1H), 6.63 (d, J=7.5 Hz, 1H), 6.89 (d, J=8.7 Hz, 1H), 7.07-7.27 (m, 5H), 7.41 (s, 1H), 7.81-7.86 (m, 2H), 8.22 (d, J=8.7 Hz, 1H).

EXAMPLE 155

Preparation of Compound 155: 2-(1-{3-[3-(4-fluoro-benzoyl)-6-propoxy-indol-1-yl]-propyl}-1H-indol-4-yloxy)-2-methyl-propionic acid Compound 155 was prepared in a manner similar to that described in Example 1.

$^1$H NMR (ppm): CDCl$_3$ δ 0.97 (t, J=7.5 Hz, 3H), 1.67 (s, 6H), 1.85-1.92 (m, 2H), 2.35 (p, 2H), 3.96 (t, J=5.7 Hz, 2H), 4.05 (t, J=7.2 Hz, 2H), 4.42 (t, J=6.6 Hz, 2H), 6.52 (dd, J=0.6, 3.0 Hz, 1H), 6.61 (dd, J=0.6, 7.5 Hz, 1H), 6.77 (d, J=2.1 Hz, 1H), 6.95-7.20 (m, 6H), 7.45 (s, 1H), 7.82-7.87 (m, 2H), 7.27 (d, J=8.7 Hz, 1H).

EXAMPLE 156

Preparation of Compound 156: 2-(1-{ 3-[3-(4-fluoro-benzoyl)-7-propyl-1H-indol-6-yloxy]-propyl}-1H-indol-4-yloxy)-2-methyl-propionic acid Compound 156 was prepared in a manner similar to that described in Example 1.

$^1$H NMR (ppm): CDCl$_3$ δ 1.06 (t, J=7.5 Hz, 3H), 1.68 (s, 6H), 1.63-1.78 (m, 2H), 1.83-1.95 (m, 2H), 2.34 (p, 2H), 2.92 (t, J=7.5 Hz, 2H), 4.00 (t, J=5.7 Hz, 2H), 4.41 (t, J=6.6 Hz, 2H), 6.54 (d, J=3.0 Hz, 1H), 6.62 (d, J=7.2 Hz, 1H), 6.88 (d, J=9.0 Hz, 1H), 7.06-7.20 (m, 5H), 7.60 (d, J=3.0 Hz, 1H), 7.82-7.89 (m, 2H), 8.13 (d, J=8.7 Hz, 1H), 8.57 (bs, 1H).

EXAMPLE 157

Preparation of Compound 157: 2-methyl-2-{1-[3-(1-phenyl-4-propyl-1H-benzoimidazol-5-yloxy)-propyl]-1H-indol-4-yloxy}-propionic acid Compound 157 was prepared in a manner similar to that described in Example 1.

$^1$H NMR (ppm): CDCl$_3$ δ 1.04 (t, J=7.2 Hz, 3H), 1.73 (s, 6H), 1.73-1.84 (m, 2H), 2.33 (p, 2H), 3.13 (t, J=7.5 Hz, 2H), 3.97 (t, J=5.7 Hz, 2H), 4.41 (t, J=6.6 Hz, 2H), 6.58 (d, J=3.0 Hz, 1H), 6.64 (d, J=7.2 Hz, 1H), 6.89 (d, J=9.0 Hz, 1H), 7.03-7.12 (m, 3H), 7.28 (d, J=8.7 Hz, 1H), 7.46-7.59 (m, 5H), 8.27 (s, 1H).

EXAMPLE 158

Preparation of Compound 158: {1-[3-(6-benzoyl-1-propyl-naphthalen-2-yloxy)-propyl]-1H-indol-5-yloxy}-acetic acid Compound 158 was prepared in a manner similar to that described in Example 1.

$^1$H NMR (ppm): CDCl$_3$ δ 1.03 (t, J=7.5 Hz, 3H), 1.63-1.71 (m, 2H), 2.27 (p, 2H), 3.09 (t, J=7.5 Hz, 2H), 3.96 (t, J=5.4 Hz, 2H), 4.33 (t, J=6.6 Hz, 2H), 4.62 (s, 2H), 6.39 (dd, J=0.9, 3.0 Hz, 1H), 6.83 (dd, J=2.7, 9.0 Hz, 1H), 7.00-7.02 (m, 2H), 7.08 (d, J=9.0 Hz, 1H), 7.20 (d, J=9.0 Hz, 1H), 7.39-7.45 (m, 2H), 7.49-7.55 (m, 1H), 7.66 (d, J=9.0 Hz, 1H), 7.75-7.78 (m, 2H), 7.88 (dd, J=1.8, 9.0 Hz, 1H), 7.98 (d, J=9.0 Hz, 1H) 8.12 (d, J=1.8 Hz, 1H).

EXAMPLE 159

Preparation of Compound 159: (1-{3-[4-(4-fluoro-benzoyl)-2-propyl-phenoxy]-propyl}-1H-indol-5-yloxy)-acetic acid Compound 159 was prepared in a manner similar to that described in Example 1.

$^1$H NMR (ppm): CDCl$_3$ δ 0.94 (t, J=7.2 Hz, 3H), 1.56-1.66 (m, 2H), 2.25 (p, 2H), 2.63 (t, J=7.5 Hz, 2H), 3.85 (t, J=5.4 Hz, 2H), 4.28 (t, J=6.6 Hz, 2H), 4.62 (s, 2H), 6.33 (d, J=3.0 Hz, 1H), 6.64 (dd, J=4.2, 9.0 Hz, 1H), 6.79-6.84 (m, 1H), 6.87 (d, J=9.0 Hz, 1H), 6.96-7.09 (m, 3H), 7.16 (d, J=9.0 Hz, 1H), 7.50 ( (dd, J=2.1, 9.0 Hz, 1H), 7.57 (dd, J=2.1, 5.1 Hz, 1H), 7.68-7.73 (m, 2H).

EXAMPLE 160

Preparation of Compound 160: (1-{3-[4-(4-fluoro-benzoyl)-2-propyl-phenoxy]-propyl}-1H-indol-4-yloxy)-acetic acid Compound 160 was prepared in a manner similar to that described in Example 1.

$^1$H NMR (ppm): CDCl$_3$ δ 0.94 (t, J=7.2 Hz, 3H), 1.59-1.67 (m, 2H), 2.26 (p, 2H), 2.64 (t, J=7.5 Hz, 2H), 3.88 (t, J=5.4 Hz, 2H), 4.31 (t, J=6.6 Hz, 2H), 4.75 (s, 2H), 6.37 (d, J=9.0 Hz, 1H), 6.55 (d, J=3.0 Hz, 1H), 6.66 (d, J=8.4 Hz, 1H), 6.92-7.09 (m, 5H), 7.50 (dd, J=2.1, 8.4 Hz, 1H), 7.59 (d, J=2.1 Hz, 1H), 7.69-7.73 (m, 2H).

EXAMPLE 161

Preparation of Compound 161: 2-{1-[3-(8-cyclopropylmethyl-4-trifluoromethyl-2H-benzo[e][1,3]oxazin-7-yloxy)-propyl]-1H-indol-4-yloxy}-2-methyl-propionic acid Compound 161 was prepared in a manner similar to that described in Example 1.

$^1$H NMR (ppm): CDCl$_3$ δ 0.20-0.25 (m, 2H), 0.34-0.39 (m, 2H), 0.75-0.82 (m, 1H), 1.59 (s, 6H), 2.29 (p, 2H), 2.62 (d, J=6.6 Hz, 2H), 3.94 (t, J=5.4 Hz, 2H), 4.30 (t, J=6.6 Hz, 2H), 6.36 (d, J=9.0 Hz, 1H), 6.46 (d, J=3.0 Hz, 1H), 6.54 (dd, J=5.4, 6.0 Hz, 1H), 6.92 (d, J=3.0 Hz, 1H), 7.00-7.02 (m, 2H), 7.57-7.61 (m, 1H), 11.49 (s, 1H).

EXAMPLE 162

Preparation of Compound 162: (1-{3-[4-(4-fluoro-benzoyl)-2-propyl-phenoxy]-propyl}-1H-indol-6-yloxy)-acetic acid Compound 162 was prepared in a manner similar to that described in Example 1.

$^1$H NMR (ppm): CDCl$_3$ δ 0.96 (t, J=7.2 Hz, 3H), 1.63-1.70 (m, 2H), 2.18 (p, 2H), 2.66 (t, J=7.5 Hz, 2H), 3.76 (t, J=5.4 Hz, 2H), 4.18 (t, J=6.6 Hz, 2H), 4.42 (s, 2H), 6.40 (d, J=3 Hz, 1H), 6.70 (d, J=8.7 Hz, 1H), 6.65 (dd, J=1.8, 8.7 Hz, 1H), 6.97 (s, 1H), 7.08 (d, J=3 Hz, 1H), 7.12 (t, J=8.4 Hz, 2H), 7.53 (d, J=8.4 Hz, 1H), 7.61 (dd, J=2.1, 8.4 Hz, 1H), 7.67 (d, J=2.1 Hz, 1H), 7.75-7.82 (m, 2H).

EXAMPLE 163

Preparation of Compound 163: {1-[3-(6-benzoyl-1-propyl-naphthalen-2-yloxy)-propyl]-1H-indol-6-yloxy}-acetic acid Compound 163 was prepared in a manner similar to that described in Example 1.

$^1$H NMR (ppm): CDCl$_3$ δ 1.06 (t, J=7.5 Hz, 3H), 1.65-1.74 (m, 2H), 2.22 (p, 2H), 3.12 (t, J=7.5 Hz, 2H), 3.87 (t, J=5.7 Hz, 2H), 4.26 (t, J=6.3 Hz, 2H), 4.39 (s, 2H), 6.36 (d, J=2.4 Hz, 1H), 6.78 (dd, J=2.1, 8.4 Hz, 1H), 6.96 (d, J=2.4 Hz, 1H), 7.10 (d, J=3.0 Hz, 1H), 7.19 (d, J=8.7 Hz, 1H), 7.26-7.49 (m, 3H), 7.56-7.63 (m, 1H), 7.81 (d, J=9 Hz, 1H), 7.96 (dd, J=1.2, 8.3 Hz, 2H), 7.97 (dd, J=1.8, 8.7 Hz, 1H), 8.07 (d, J=9 Hz, 1H), 8.14 (s 1H).

EXAMPLE 164

Preparation of Compound 164: 2-methyl-2-{1-[3-(2-phenyl-7-propyl-1H-indol-6-yloxy)-propyl]-1H-indol-4-yloxy}-propionic acid Compound 164 was prepared in a manner similar to that described in Example 1.

$^1$H NMR (ppm): CDCl$_3$ δ 1.033 (t, J=7.2 Hz, 3H), 1.641 (s, 6H), 1.729-1.804 (m, 2H), 2.275-2.334 (m, 2H), 2.914 (t, J=8.0 Hz, 2H), 3.980 (t, J=6.0 Hz, 2H), 4.385 (t, J=6.8 Hz, 2H), 6.511 (d, J=3.2 Hz, 1H), 6.613 (d, J=8.0Hz, 1H), 6.707-6.738 (m, 2H), 7.055-7.093 (m, 2H), 7.145 (s, 1H), 7.171 (d, J=5.2 Hz, 1H), 7.361 (d, J=8.8 Hz, 1H), 7.427 (t, J=8.0 Hz, 2H), 7.647 (d, J=8.4 Hz, 2H), 8.070 (br s, 1H).

EXAMPLE 165

Preparation of Compound 165: {1-[3-(2-phenyl-7-propyl-1H-indol-6-yloxy)-propyl]-1H-indol-4-yloxy}-acetic acid Compound 165 was prepared in a manner similar to that described in Example 1.

$^1$H NMR (ppm): CDCl$_3$ δ 1.033 (t, J=7.2 Hz, 3H), 1.748-1.803 (m, 2H), 2.264-2.325 (m, 2H), 2.911 (t, J=7.6 Hz, 2H), 3.971 (t, J=6.0 Hz, 2H), 4.389 (t, J=6.8 Hz, 2H), 4.808 (s, 2H), 6.452 (t, J=4.0 Hz, 1H), 6.615 (d, J=3.6 Hz, 1H), 6.705 (s, 1H), 6.727-6.740 (m, 1H), 7.045 (d, J=6.4 Hz, 1H), 7.083 (d, J=8.4 Hz, 2H), 7.293 (t, J=6.4 Hz, 1H), 7.358 (d, J=8.0 Hz, 1H), 7.427 (t, J=8.0 Hz, 2H), 7.643 (d, J=7.2 Hz, 2H), 8.057 (br s, 1H).

EXAMPLE 166

Preparation of Compound 166: {4-[3-(2-phenyl-7-propyl-1H-indol-6-yloxy)-propoxy]-indol-1-yl}-acetic acid Compound 166 was prepared in a manner similar to that described in Example 2.

$^1$H NMR (ppm): CDCl$_3$ δ 0.923 (t, J=7.2 Hz, 3H), 1.645-1.713 (m, 2H), 2.334-2.392 (m, 2H), 2.810-2.856 (m, 2H), 4.266 (q, J=6.0, 12.8 Hz, 2H), 4.361 (q, J=6.0, 12.4 Hz, 2H), 4.828 (s, 2H), 6.572 (t, J=7.2 Hz, 1H), 6.665 (d, J=3.2 Hz, 1H), 6.727 (s, 1H), 6.830-6.861 (m, 2H), 7.013-7.145 (m, 2H), 7.277 (t, J=8.0 Hz, 1H), 7.359-7.430 (m, 3H), 7.627 (d, J=7.2 Hz, 2H), 8.017 (br s, 1H).

EXAMPLE 167

Preparation of Compound 167: {4-[3-(2-phenyl-5-propyl-benzofuran-6-yloxy)-propoxy]-indol-1-yl}-acetic acid Compound 167 was prepared in a manner similar to that described in Example 2.

$^1$H NMR (ppm): CDCl$_3$ δ 0.861 (t, J=7.2 Hz, 3H), 1.512-1.579 (m, 2H), 2.304-2.345 (m, 2H), 2.581 (t, J=7.2 Hz, 2H), 4.172 (t, J=6.0 Hz, 2H), 4.280 (t, J=6.0 Hz, 2H), 4.711 (s, 2H), 6.497 (d, J=8.0 Hz, 1H), 6.586 (d, J=2.8 Hz, 1H), 6.822 (s, 2H), 6.920 (d, J=3.6 Hz, 1H), 6.954-7.059 (m, 2H), 7.191-7.222 (m, 2H), 7.324 (t, J=8.0 Hz, 2H), 7.707 (d, J=7.2 Hz, 2H).

HRMS-EI (M$^+$): 483.20.

EXAMPLE 168

Preparation of Compound 168: {1-[3-(2-phenyl-5-propyl-benzofuran-6-yloxy)-propyl]-1H-indol-4-yloxy}-acetic acid Compound 168 was prepared in a manner similar to that described in Example 1.

$^1$H NMR (ppm): CDCl$_3$ δ 0.923 (t, J=7.2 Hz, 3H), 1.601-1.657 (m, 2H), 2.213-2.244 (m, 2H), 2.656 (t, J=7.2 Hz, 2H), 3.867 (t, J=5.6 Hz, 2H), 4.326 (t, J=7.2 Hz, 2H), 4.657 (s, 2H), 6.346 (d, J=7.6 Hz, 1H), 6.523 (d, J=2.8 Hz, 1H), 6.900-7.024 (m, 5H), 7.178-7.231 (m, 2H), 7.316 (t, J=8.0 Hz, 2H), 7.709 (d, J=7.6 Hz, 2H.

EXAMPLE 169

Preparation of Compound 169: 2-methyl-2-{1-[3-(2-phenyl-5-propyl-benzofuran-6-yloxy)-propyl]-1H-indol-4-yloxy}-propionic acid Compound 169 was prepared in a manner similar to that described in Example 1.

$^1$H NMR (ppm): CDCl$_3$ δ 0.908 (t, J=7.2 Hz, 3H), 1.503 (s, 6H), 1.561-1.636 (m, 2H), 2.156-2.201 (m, 2H), 2.632 (t, J=8.0 Hz, 2H), 3.809 (t, J=6.0 Hz, 2H), 4.275 (t, J=6.8 Hz, 2H), 6.401 (d, J=7.6 Hz, 1H), 6.854-6.905 (m, 3H), 6.964-6.983 (m, 2H), 7.163-7.198 (m, 2H), 7.300 (t, J=8.0 Hz, 2H), 7.691 (d, J=7.2 Hz, 2H).

EXAMPLE 170

Preparation of Compound 170: {5-[3-(2-oxo-8-propyl-4-trifluoromethyl-2H-chromen-7-yloxy)-propoxy]-indol-1-yl}-acetic acid Compound 170 was prepared in a manner similar to that described in Example 2.

$^1$H NMR (ppm): CDCl$_3$+MeOH-d$_4$ δ 0.94 (t, J=7.2 Hz, 3H), 1.53-1.61 (m, 2H), 2.34 (p, 2H), 2.83 (t, J=7.5 Hz, 2H), 4.21 (t, J=6.0 Hz, 2H), 4.30 (t, J=6.0 Hz, 2H), 4.78 (s, 2H), 6.44 (d, J=2.7 Hz, 1H), 6.59 (s, 1H), 6.85 (dd, J=2.4, 9.0 Hz, 1H), 6.93 (d, J=9.0 Hz, 1H), 7.06 (d, J=3.3 Hz, 1H), 7.09 (d, J=2.1 Hz, 1H), 7.14 (d, J=8.7Hz, 1H), 7.52-7.55 (m, 1H).

EXAMPLE 171

Preparation of Compound 171: {5-[3-(1-phenyl-4-propyl-1H-benzoimidazol-5-yloxy)-propoxy]-indol-1-yl}-acetic acid Compound 171 was prepared in a manner similar to that described in Example 2.

$^1$H NMR (ppm): CDCl$_3$+MeOH-d$_4$ δ 0.98 (t, J=7.5 Hz, 3H), 1.67-1.75 (m, 2H), 2.27 (p, 2H), 3.02 (t, J=7.5 Hz, 2H), 4.19 (t, J=5.7 Hz, 4H), 4.58 (s, 2H), 6.34 (d, J=3.0 Hz, 1H), 6.79 (dd, J=2.1, 8.7 Hz, 1H), 6.93-7.08 (m, 4H), 7.25 (d, J=8.7 Hz, 1H), 7.38-7.54 (m, 5H), 8.05 (s,1H).

EXAMPLE 172

Preparation of Compound 172: 2-{5-[3-(7-propyl-3-trifluoromethyl-benzo[d]isoxazol-6-yloxy)-propoxy]-indol-1-yl}-butyric acid Compound 172 was prepared in a manner similar to that described in Example 2.

$^1$H NMR (ppm): CDCl$_3$ δ 0.88-0.96 (m, 6H), 1.62-1.72 (m, 2H), 2.12-2.38 (m, 4H), 2.90 (t, J=7.5 Hz, 2H), 4.22 (t, J=6.0 Hz, 2H), 4.31 (t, J=6.0 Hz, 2H), 4.82 (dd, J=6.0, 9.6 Hz, 1H), 6.47 (d, J=3 Hz, 1H), 6.85 (dd, J=2.4, 9.0 Hz, 1H), 7.06-7.10 (m, 2H), 7.18-7.21 (m, 2H), 7.53 (d, J=8.7 Hz, 1H).

EXAMPLE 173

Preparation of Compound 173: {5-[5-(7-propyl-3-trifluoromethyl-benzo[d]isoxazol-6-yloxy)-pentyloxy]-indol-1-yl}-acetic acid Compound 173 was prepared in a manner similar to that described in Example 2.

$^1$H NMR (ppm): CDCl$_3$ δ 0.97 (t, J=7.5 Hz, 3H), 1.65-1.76 (m, 4H), 1.86-1.99 (m, 4H), 2.92 (t, J=7.5 Hz, 2H), 4.05 (t, J=6.3 Hz, 2H), 4.14 (t, J=6.3 Hz, 2H), 4.81 (s, 2H), 6.45 (d, J=3.0 Hz, 1H), 6.87 (dd, J=2.4, 8.7 Hz, 1H), 7.07-7.11 (m, 3H), 7.16 (d, J=9.0 Hz, 1H), 7.55 (d, J=8.7 Hz, 1H).

EXAMPLE 174

Preparation of Compound 174: {5-[4-(7-propyl-3-trifluoromethyl-benzo[d]isoxazol-6-yloxy)-butoxy]-indol-1-yl}-acetic acid Compound 174 was prepared in a manner similar to that described in Example 2.

$^1$H NMR (ppm): CDCl$_3$ δ 0.94 (t, J=7.5 Hz, 3H), 1.62-1.75 (m, 2H), 1.94-2.10 (m, 4H), 2.89 (t, J=7.5 Hz, 2H), 4.05 (t, J=5.4 Hz, 2H), 4.14 (t, J=6.0 Hz, 2H), 4.63 (s, 2H), 6.38 (d, J=3.0 Hz, 1H), 6.83 (dd, J=2.4, 8.7 Hz, 1H), 6.90 (d, J=2.1 Hz, 1H), 7.00-7.05 (m, 3H), 7.52 (d, J=8.7 Hz, 1H).

EXAMPLE 175

Preparation of Compound 175: [4-(3-phenoxazin-10-yl-propoxy)-indol-1-yl]-acetic acid Compound 175 was prepared in a manner similar to that described in Example 2.

$^1$H NMR (ppm): CDCl$_3$+MeOH-d$_4$ δ 2.12-2.22 (m, 2H), 3.73-3.83 (m, 2H), 4.15-4.25 (m, 2H), 4.79 (s, 2H), 6.49 (d, J=7.8 Hz, 1H), 6.52-6.65 (m, 5H), 6.66-6.73 (m, 4H), 6.86 (d, J=8.1 Hz, 1H), 7.00 (s, 1H), 7.08 (t, J=8.0 Hz, 1H).

HRMS-EI (M$^+$): 414.16.

EXAMPLE 176

Scintillation Proximity Assay

Scintillation proximity assay (SPA) was conducted on 96-well microtiter plates (catalog number 6005290, Packard Instrument, Meriden, Conn.) with a 100 µL well volume. The assay buffer contained 10 mM Tris-Cl, pH 7.2, 1 mM EDTA, 10% (w/v) glycerol, 10 mM sodium molybdate, 1 mM dithiothreitol, 0.5 mM phenylmethylsulfonyl fluoride, 2 µg/mL benzamidine, and 0.1% dry milk powder. Protein A-yttrium silicate SPA beads (catalog number RPN143, Amersham Biosciences, Piscataway, N.J.) was suspended in 50 mL of the above assay buffer except that dry milk powder was replaced with 0.01% sodium azide. The recombinant GST-hPPAR-γ$^{LBD}$ preparations were first diluted 400-fold and the diluted solution was used to produce a solution with a final concentration of approximately 5 nM. Goat anti-GST antibodies (catalog number 27-4577-01, Amersham Biosciences, Piscataway, N.J.) were diluted 400-fold and then the diluted solution was used to obtain a final 2000-fold diluted solution. A test compound was dissolved in DMSO to obtain a solution with a final concentration of 10 µM. 60 Ci/mmol [$^3$H] BRL-49653 (a PPARγ ligand solution, American Radiolabeled Chemicals, St. Louis, Mo.) was diluted 425-fold in ethanol and then the diluted solution was used to obtain a final concentration of 7.8 nM. 20 µL of diluted solutions containing GST-PPARγ$^{LBD}$, goat anti-GST antibodies, well-suspended protein A-yttrium silicate SPA beads, and a test compound were sequentially added to each well of a microtiter plate. Finally, 20 µL of a diluted hot BRL49653 solution was added to each well. The plate was incubated at 4° C. for 24 hours with gentle shaking. Radioactivity was quantified using a Packard Topcount scintillation counter.

SPA binding assays for PPARα and PPARδ were conducted in a manner similar to the procedures described above.

118 of the 175 exemplary compounds described above were tested for their efficacy in binding to PPARs. Specifically, in the PPARα binding assay, 16 compounds showed IC$_{50}$ values (the concentration of a test compound at which 50% [$^3$H] BRL-49653 on PPAR is displaced) lower than 1 µM and 13 compounds showed IC$_{50}$ values between 1 µM and 10 µM. In the PPARγ binding assay, 55 compounds showed IC$_{50}$ values lower than 1 µM and 49 compounds showed IC$_{50}$ values between 1 µM and 10 µM. In the PPARδ binding assay, 14 compounds showed IC$_{50}$ values lower than 1 µM and 36 compounds showed IC$_{50}$ values between 1 µM and 10 µM.

EXAMPLE 177

PPAR Transactivation

Huh-7 cells were seeded at a 6×10$^4$ cells/well concentration in 24-well cell culture plates in high glucose Dulbecco's modified Eagle's medium containing 10% fetal calf serum, 100 units/mL penicillin G, and 100 mg/mL streptomycin sulfate at 37° C. in a humidified 10% CO$_2$ atmosphere. After 24 hours, transfections were performed using Fugene 6 transfection reagent (Roche, Penzberg, Germany) according to the instructions of the manufacturer. Specifically, a transfection mixture was prepared by adding to each well 0.5 µl of Fugene 6, 0.05 µg of pGAL4-PPARγ(LBD) plasmid, 0.14 µg of pG5-TK-Luc reporter, and 0.25 ng of a pRL-SV40 Renilla luciferase plasmid as transfection internal control. Cells were incubated in the transfection mixture overnight at 37° C. in a 10% CO$_2$ atmosphere. Then the cells were incubated for one day in fresh high glucose Dulbecco's modified Eagle's medium with increasing concentrations of a test compound. Since the test compounds were dissolved in DMSO, control cells were incubated with a DMSO solution of equivalent concentrations. The highest DMSO concentration was 0.1%, which was shown not to affect transactivation activity. After one day treatment, cells were harvested and cell lysates were produced using Reporter Lysis Buffer (Promega, Madison, Wis.) according to the manufacturer's instructions. Luciferase activity in cell extracts was determined by using the Luciferase Assay kit (Promega, Madison, Wis.) and counted in a SIRIUS-0 luminometer (Berthold detection systems, Pforzheim, Germany). Briefly, 50 µL of Luciferase Assay Reagent II (LARII) was added into a vial containing 5 µL of cell lysate and then the Firefly Luciferase activity of the mixture was measured. 50 µL of Stop & Glo Reagent was then added into the vial and the Renilla Luciferase activity of the mixture was measured. The transactivation result was expressed with the ratio of Firefly Luciferase counting over Renilla Luciferase counting.

118 of the 175 exemplary compounds described above were tested for their efficacy in PPAR transactivation activities. Specifically, in the PPARα transactivation assay, 43 compounds showed $EC_{50}$ values (the concentration at which a test compound shows 50% of its maximal PPAR reporter activity) lower than 1 µM and 12 compounds showed $EC_{50}$ values between 1 µM and 10 µM. In the PPARγ transactivation assay, 15 compounds showed $EC_{50}$ values lower than 1 µM and 33 compounds showed $EC_{50}$ values between 1 µM and 10 µM. In the PPARδ transactivation assay, 9 compounds showed $EC_{50}$ values lower than 1 µM and 13 compounds showed $EC_{50}$ values between 1 µM and 10 µM.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A compound of formula (I):

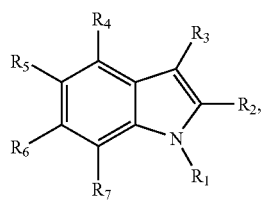
(I)

wherein
$R_1$ is $(CR_cR_d)_m$—X—$R_a$ or $(CR_cR_d)_n$—X—$R_b$, in which m is 3-5; n is 2-5; X is $N(R_e)$, O, or S, or X and $R_a$ or X and $R_b$, taken together, is heteroaryl; $R_a$ is H, $C_1$-$C_6$ alkyl, $C_3$-$C_{15}$ cycloalkyl, $C_3$-$C_{15}$ heterocycloalkyl, heteroaryl, or aryl optionally substituted with OH, halogen, $C_3$-$C_6$ alkyl, $C_3$-$C_{15}$ cycloalkyl, $C_3$-$C_{15}$ heterocycloalkyl, $C_1$-$C_6$ alkoxy, aryloxy, heteroaryloxy, heteroaryl, aryl, $NO_2$, CN, $COOR_f$, or $C(O)R_f$, or $R_a$ and X, taken together, is heteroaryl; $R_b$ is H, $C_1$-$C_6$ alkyl, $C_3$-$C_{15}$ cycloalkyl, $C_3$-$C_{15}$ heterocycloalkyl, heteroaryl, or aryl optionally substituted with OH, halogen, $C_3$-$C_6$ alkyl, $C_3$-$C_{15}$ cycloalkyl, $C_3$-$C_{15}$ heterocycloalkyl, aryloxy, heteroaryloxy, heteroaryl, aryl, $NO_2$, CN, $COOR_f$, or $C(O)R_f$, or $R_b$ and X, taken together, is heteroaryl; each $R_c$, independently, is H, $C_1$-$C_6$ alkyl, aryl, or heteroaryl; and each $R_d$, independently, is H, $C_1$-$C_6$ alkyl, aryl, or heteroaryl; each of $R_e$ and $R_f$ independently, being H, $C_1$-$C_6$ alkyl, aryl, or heteroaryl; each of $R_2$ and $R_3$ is H; and one of $R_4$, $R_5$, $R_6$, and $R_7$ is OH, $C_1$-$C_6$ alkyl, $C_3$-$C_{15}$ cycloalkyl, $C_3$—$C_{15}$ heterocycloalkyl, aryl, heteroaryl, $C_1$-$C_6$ alkoxy, aryloxy, heteroaryloxy, $C_1$-$C_6$ alkylthio, arylthio, $NH_2$, $C_1$-$C_6$ alkylamino, $C_1$-$C_{12}$ dialkylamino, arylamino, diarylamino, $NO_2$, CN, $SO_3H$, $SO_2N(R_gR_h)$, $SO_2R_g$, $COOR_g$, or $C(O)R_g$; and each of the others, independently, is H, $C_1$-$C_6$ alkyl, $C_3$-$C_{15}$ cycloalkyl, $C_3$-$C_{15}$ heterocycloalkyl, aryl, heteroaryl, $C_1$-$C_6$ alkoxy, aryloxy, heteroaryloxy, $C_1$-$C_6$ alkylthio, arylthio, $NH_2$, $C_1$-$C_6$ alkylamino, $C_1$-$C_{12}$ dialkylamino, arylamino, diarylamino, $NO_2$, CN, $SO_3H$, $SO_2N(R_gR_h)$, $SO_2R_g$, $COOR_g$, or $C(O)R_g$; each $R_g$, independently, is H, $C_1$-$C_6$ alkyl, aryl, or heteroaryl; and each $R_h$, independently, is H or $C_1$-$C_6$ alkyl.

2. The compound of claim 1, wherein $R_a$ is heteroaryl or aryl substituted with $C_3$-$C_6$ alkyl, $C_1$-$C_6$ alkoxy, heteroaryl, $C(O)R_f$, or $NO_2$, or $R_a$ and X, taken together, is heteroaryl; $R_b$ is heteroaryl; n is 2; each of $R_2$ and $R_3$ is H; and one of $R_4$, $R_5$, $R_6$, and $R_7$ is OH, $C_1$-$C_6$ alkyl, $C_1$-$C_6$ alkoxy, or $COOR_e$; and each of the others, independently, is H, $C_1$-$C_6$ alkyl, $C_1$-$C_6$ alkoxy, or $C(O)R_e$.

3. The compound of claim 2, wherein $R_a$ is heteroaryl or aryl substituted with $C_3$-$C_6$ alkyl or $C(O)R_f$.

4. The compound of claim 3, wherein each $R_a$, independently, is

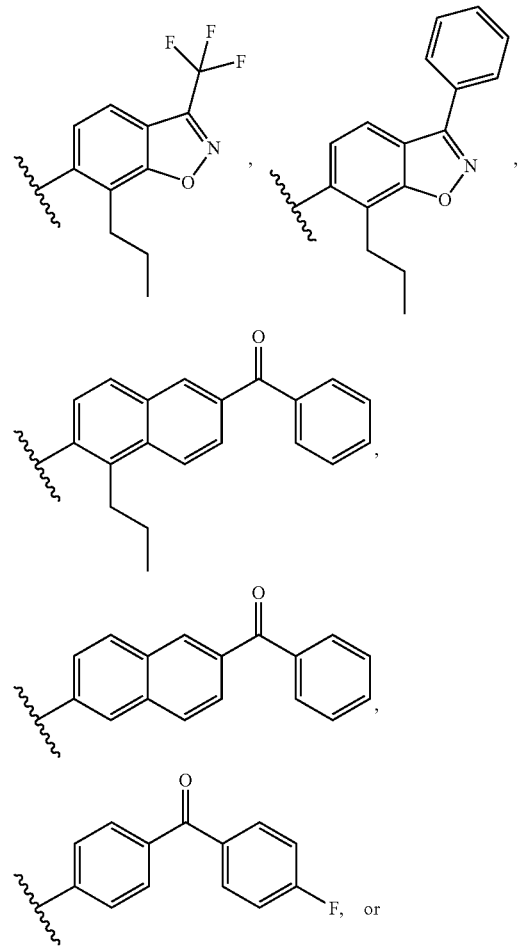

-continued

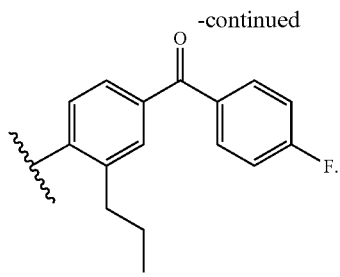

5. The compound of claim 3, wherein each of $R_2$ and $R_3$ is H; and one of $R_4$, $R_5$, $R_6$, and $R_7$ is OH, OCH$_2$COOR, OC(CH$_3$)$_2$COOR, OCH(CH$_3$)COOR, O(CH$_2$)$_2$COOR, O(CH2)$_3$COOR, CH$_2$COOR, COOR,

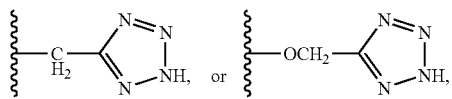

in which R is H, $C_1$-$C_6$ alkyl, aryl, or heteroaryl

6. The compound of claim 4, wherein each of $R_2$ and $R_3$ are H; and
one of $R_4$, $R_5$, $R_6$, and $R_7$ is OH, OCH$_2$COOR, OC(CH$_3$)$_2$COOR, OCH(CH$_3$)COOR, O(CH$_2$)$_2$COOR, O(CH$_2$)$_3$COOR, CH$_2$COOR, COOR,

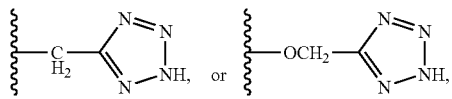

in which R is H, $C_1$-$C_6$ alkyl, aryl, or heteroaryl.

7. A pharmaceutical composition comprising a compound of claim 1 and a pharmaceutically acceptable carrier.

8. A pharmaceutical composition comprising a compound of claim 1 and tetraethylthiuram disulfide.

9. A compound of formula (I):

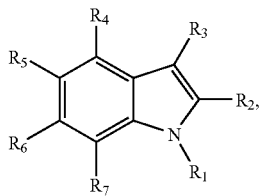

wherein
$R_1$ is H, $C_1$-$C_6$ alkyl, $C_3$-$C_{15}$ cycloalkyl, $C_3$-$C_{15}$ heterocycloalkyl, aryl, heteroaryl, C(O)$R_a$, or SO$_2$$R_a$, in which $R_a$ is $C_1$-$C_6$ alkyl, heteroaryl, or aryl optionally substituted with CF$_3$, OH, halogen, $C_1$-$C_6$ alkoxy, aryloxy, heteroaryloxy, $C_3$-$C_{15}$ cycloalkyl, $C_3$-$C_{15}$ heterocycloalkyl, aryl, heteroaryl, NO$_2$, CN, COOR$_b$, or C(O)R$_b$; $R_b$ being H, $C_1$-$C_6$ alkyl, aryl, or heteroaryl;
each of $R_2$ and $R_3$ is H; and one of $R_4$, $R_5$, $R_6$, $R_7$ is O—(CR$_e$R$_f$)$_m$—X—$R_c$, or O—C(R$_e$R$_f$)R$_d$; and
each of the others, independently, is H, OH, halogen, $C_1$-$C_6$ alkyl, $C_3$-$C_{15}$ cycloalkyl, $C_3$—$C_{15}$ heterocycloalkyl, aryl, heteroaryl, $C_1$-$C_6$ alkoxy, aryloxy, heteroaryloxy, $C_1$-$C_6$ alkylthio, arylthio, NH$_2$, $C_1$-$C_6$ alkylamino, $C_1$-$C_{12}$ dialkylamino, arylamino, diarylamino, NO$_2$, CN, SO$_3$H, SO$_2$N(R$_g$R$_h$), SO$_2$R$_g$, COOR$_g$, or C(O)R$_g$; or one $R_4$, $R_5$, $R_6$, and $R_7$ is, O —(CR$_e$R$_f$)$_n$—X —$R_c$, or O —C(R$_e$R$_f$)R$_d$; and each of the others, independently, is H, OH, halogen, $C_3$-$C_6$ alkyl, $C_3$-$C_{15}$ cycloalkyl, $C_3$—$C_{15}$ heterocycloalkyl, aryl, heteroaryl, $C_3$-$C_6$ alkoxy, aryloxy, heteroaryloxy, $C_1$-$C_6$ alkylthio, arylthio, NH$_2$, $C_1$-$C_6$ alkylamino, $C_1$-$C_{12}$ dialkylamino, arylamino, diarylamino, NO$_2$, CN, SO$_3$H, SO$_2$N(R$_g$R$_h$), SO$_2$R$_g$, COOR$_g$, or C(O)R$_g$; in which m is 3-5; n is 2-5; X is O; each $R_c$, independently, is $C_1$-$C_6$ alkyl, COOR$_j$, heteroaryl containing at least two aromatic rings fused together, or aryl optionally substituted with OH, halogen, $C_3$-$C_6$ alkyl, $C_3$-$C_{15}$ cycloalkyl, $C_3$—$C_{15}$ heterocycloalkyl, $C_1$-$C_6$ alkoxy, aryloxy, heteroaryloxy, heteroaryl, aryl, NO$_2$, CN, COOR$_j$, or C(O)R$_j$; each R$_d$, independently, is H, OH, halogen, NH$_2$, $C_1$-$C_6$ alkylamino, $C_1$-$C_{12}$ dialkylamino, $C_1$-$C_6$ alkyl COOR$_j$; each $R_e$, independently, is H, $C_1$-$C_6$ alkyl, aryl, or heteroaryl; each R$_f$, independently, is H, or $C_1$-$C_6$ alkyl; and each of R$_g$ and R$_h$, independently, is H, $C_1$-$C_6$ alkyl, aryl, or heteroaryl; each of R$_i$ and R$_j$, independently, is H, $C_1$-$C_6$ alkyl, aryl, or heteroaryl.

10. The compound of claim 9, wherein $R_1$ is H, $C_1$-$C_6$ alkyl, or SO$_2$R$_a$; each $R_2$ and $R_3$ is H; one of $R_4$, $R_5$, $R_6$, and $R_7$ is O—(CR$_e$CR$_f$)$_m$—X —$R_c$, or O —C(R$_e$R$_f$)R$_d$, and each of the others, independently, is H, $C_1$-$C_6$ alkyl, $C_1$-$C_6$ alkoxy, or COOR$_g$; or each of $R_2$ and $R_3$ is H and one of $R_4$, $R_5$, $R_6$, and $R_7$ is O —(CR$_e$R$_f$)$_n$—X —$R_c$, and each of the others, independently, is H; n is 2; $R_c$ is heteroaryl containing at least two aromatic rings fused together or aryl substituted with $C_3$-$C_6$ alkyl, heteroaryl, or C(O)R$_j$; and R$_d$ is COOR$_j$.

11. The compound of claim 10, wherein $R_c$ is heteroaryl containing at least two aromatic rings fused together or aryl substituted with $C_3$-$C_6$ alkyl or C(O)R$_j$.

12. The compound of claim 11, wherein $R_c$ is

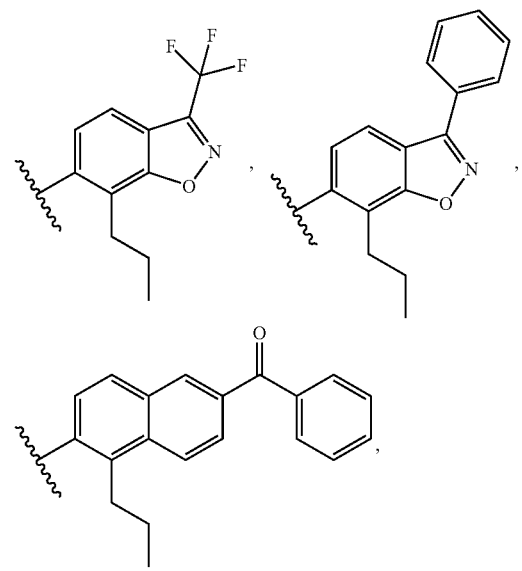

-continued

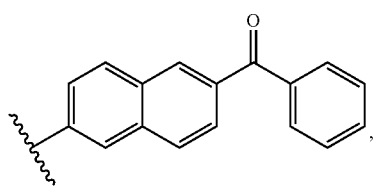

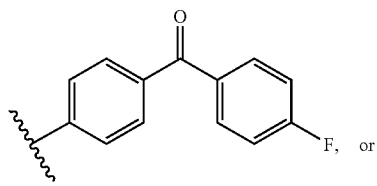, or

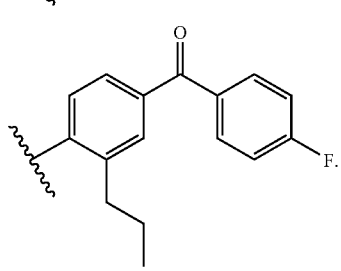

13. The compound of claim 11, wherein $R_1$ is H, $CH_2COOR$, $CH(CH_3)COOR$, $CH(CH_2CH_3)COOR$, $CH_2CH_2COOR$, $CH_2(CH_2)_2COOR$, or

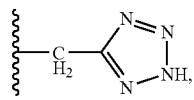

,in which R is H, $C_1C_6$ alkyl, aryl, or heteroaryl.

14. The compound of claim 12, wherein $R_1$ is H, $CH_2COOR$, $CH(CH_3)COOR$, $CH(CH_2CH_3)COOR$, $CH_2CH_2COOR$, $CH_2(CH_2)_2COOR$, or

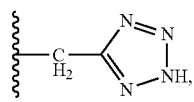

,in which R is H, $C_1$-$C_6$ alkyl, aryl, or heteroaryl.

15. The compound of claim 9, wherein the compound is one of compounds 2, 17, 26-29, 32, 35, 42, 53-55, 57, 58, 60, 69-73, 80-83, 88, 90, 93, 100, 112, 113, 115, 117, 119, 125-129, 131-133, 137-140, 144, 145, 152, 166, 167, and 170-174, or a salt thereof.

16. A pharmaceutical composition comprising a compound of claim 9 and a pharmaceutically acceptable carrier.

17. A pharmaceutical composition comprising a compound of claim 9 and tetraethylthiuram disulfide.

18. A compound of formula (I):

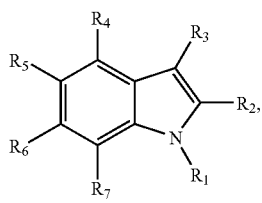

(I)

wherein
$R_1$ is $C_1$-$C_6$ alkyl, $C_3$-$C_{15}$ cycloalkyl, $C_3$-$C_{15}$ heterocycloalkyl, heteroaryl, $C(O)R_a$, $SO_2R_a$, or aryl optionally substituted with OH, $C_1$-$C_6$ alkyl, $C_3$-$C_{15}$ cycloalkyl, $C_3$-$C_{15}$ heterocycloalkyl, $C_1$-$C_6$ alkoxy, aryloxy, heteroaryloxy, heteroaryl, aryl, $NO_2$, CN, $COOR_a$, or $C(O)R_a$; in which $R_a$ is $C_1$-$C_6$ alkyl, heteroaryl, or aryl optionally substituted with $CF_3$, OH, halogen, $C_1$-$C_6$ alkoxy, aryloxy, heteroaryloxy, $C_3$-$C_{15}$ cycloalkyl, $C_3$-$C_{15}$ heterocycloalkyl, aryl, heteroaryl, $NO_2$, CN, $COOR_b$, or $C(O)R_b$; $R_b$ being H, $C_1$-$C_6$ alkyl, aryl, or heteroaryl;
Each of $R_2$ and $R_3$ is H; and
one of $R_4$, $R_5$, $R_6$, $R_7$ is O —$(CR_eCR_f)_m$—X —$R_c$, or O —$C(R_eR_f)R_d$; and each of the others, independently, is H, OH, halogen, $C_1$-$C_6$ alkyl, $C_3$-$C_{15}$ cycloalkyl, $C_3$-$C_{15}$ heterocycloalkyl, aryl, heteroaryl, $C1$-$C_6$ alkoxy, aryloxy, heteroaryloxy, $C_1$-$C_6$ alkylthio, arylthio, $NH_2$, $C_1$-$C_6$ alkylamino, $C_1$-$C_{12}$ dialkylamino, arylamino, diarylamino, $NO_2$, CN, $SO_3H$, $SO_2N(R_gR_h)$, $SO_2R_g$, $COOR_g$, or $C(O)R_g$; or one $R_4$, $R_5$, $R_6$, and $R_7$ is O —$(CR_eR_f)_n$—X —$R_c$, or O —$C(R_eR_f)R_d$; and each of the others, independently, is H, OH, halogen, $C_3$-$C_6$ alkyl, $C_3$-$C_{15}$ cycloalkyl, $C_3$-$C_{15}$ heterocycloalkyl, aryl, heteroaryl, $C_3$-$C_6$ alkoxy, aryloxy, heteroaryloxy, $C_1$-$C_6$ alkylthio, arylthio, $NH_2$, $C_1$-$C_6$ alkylamino, $C_1$-$C_{12}$ dialkylamino, arylamino, diarylamino, $NO_2$, CN, $SO_3H$, $SO_2N(R_gR_h)$, $SO_2R_g$, $COOR_g$, or $C(O)R_g$; in which m is 3-5; n is 2-5; X is O; $R_c$ is $C_1$-$C_6$ alkyl, $COOR_j$, heteroaryl, or aryl optionally substituted with OH, halogen, $C_3$-$C_6$ alkyl, $C_3$-$C_{15}$ cycloalkyl, $C_3$-$C_{15}$ heterocycloalkyl, $C_1$-$C_6$ alkoxy, aryloxy, heteroaryloxy, heteroaryl, aryl, $NO_2$, CN, $COOR_j$, or $C(O)R_j$; $R_d$ is H, OH, halogen, $NH_2$, $C_1$-$C_6$ alkylamino, $C_1$-$C_{12}$ dialkylamino, arylamino, diarylamino, $C_1$-$C_6$ alkyl, $COOR_i$; each $R_e$, independently, is H, $C_1$-$C_6$ alkyl, aryl, or heteroaryl; each $R_f$, independently, is H, $C_1$-$C_6$ alkyl, and each $R_g$ is H, $C_1$-$C_6$ alkyl, aryl, or heteroaryl; and each $R_h$ is H, $C_1C_6$ alkyl, each $R_i$ is $C_1$-$C_6$ alkyl, aryl, or heteroaryl; each $R_j$ is H, $C_1$-$C_6$ alkyl, aryl, or heteroaryl.

19. The compound of claim 18, wherein $R_1$ is $C_1$-$C_6$ alkyl or $SO_2R_a$; each of $R_2$, and $R_3$ is H; and one of $R_4$, $R_5$, $R_6$, $R_7$ is $(CR_eR_f)_n$—X —$R_c$ or O —$(CR_eR_f)_n$—X —$R_c$, and each of the others, independently, is H, $C_1$-$C_6$ alkyl, $C_1$-$C_6$ alkoxy, or $COOR_j$; and $R_c$ is heteroaryl or aryl substituted with heteroaryl or $C(O)R_i$.

20. The compound of claim 19, wherein $R_c$ is heteroaryl.

21. The compound of claim 20, wherein $R_c$ is pyridinyl.

22. A pharmaceutical composition comprising a compound of claim 18 and a pharmaceutically acceptable carrier.

23. A pharmaceutical composition comprising a compound of claim 18 and tetraethylthiuram disulfide.

* * * * *